United States Patent
Guillemont et al.

(10) Patent No.: US 9,315,522 B2
(45) Date of Patent: Apr. 19, 2016

(54) ANTIBACTERIAL COMPOUNDS

(71) Applicant: JANSSEN SCIENCES IRELAND UC, Little Island, Co Cork (IE)

(72) Inventors: Jerôme Emile Georges Guillemont, Andé (FR); David Francis Alain Lançois, Louviers (FR); Magali Madeleine Simone Motte, Louviers (FR); Wendy Mia Albert Balemans, Kalmthout (BE); Steffen Friedrich Walter Weidner, Illkirch-Graffenstaden (FR); David Craig McGowan, Brussels (BE); Anil Koul, Edegem (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 14/417,511

(22) PCT Filed: Aug. 9, 2013

(86) PCT No.: PCT/EP2013/066679
§ 371 (c)(1),
(2) Date: Jan. 26, 2015

(87) PCT Pub. No.: WO2014/023814
PCT Pub. Date: Feb. 13, 2014

(65) Prior Publication Data
US 2015/0210719 A1 Jul. 30, 2015

(30) Foreign Application Priority Data
Aug. 10, 2012 (EP) .................... 12180100

(51) Int. Cl.
| | | |
|---|---|---|
| *C07D 401/06* | (2006.01) | |
| *C07D 401/12* | (2006.01) | |
| *C07D 401/14* | (2006.01) | |
| *C07D 405/12* | (2006.01) | |
| *C07D 409/14* | (2006.01) | |
| *C07D 417/14* | (2006.01) | |
| *C07D 417/04* | (2006.01) | |
| *C07D 498/14* | (2006.01) | |
| *C07D 519/00* | (2006.01) | |
| *C07D 471/04* | (2006.01) | |
| *C07D 471/14* | (2006.01) | |
| *C07D 498/04* | (2006.01) | |
| *C07D 405/14* | (2006.01) | |
| *C07D 513/14* | (2006.01) | |

(52) U.S. Cl.
CPC ............ *C07D 519/00* (2013.01); *C07D 401/06* (2013.01); *C07D 401/12* (2013.01); *C07D 401/14* (2013.01); *C07D 405/12* (2013.01); *C07D 405/14* (2013.01); *C07D 409/14* (2013.01); *C07D 417/14* (2013.01); *C07D 471/04* (2013.01); *C07D 471/14* (2013.01); *C07D 498/04* (2013.01); *C07D 498/14* (2013.01); *C07D 513/14* (2013.01)

(58) Field of Classification Search
CPC .. C07D 401/06; C07D 401/12; C07D 401/14; C07D 405/12; C07D 409/14; C07D 417/14; C07D 471/04; C07D 498/14
See application file for complete search history.

(56) References Cited

U.S. PATENT DOCUMENTS 8,906,923 B2 * 12/2014 Guillemont et al. .......... 514/250

FOREIGN PATENT DOCUMENTS

| WO | WO 01/26652 A1 | 4/2001 |
|---|---|---|
| WO | WO 01/26654 A1 | 4/2001 |
| WO | WO 01/27103 A1 | 4/2001 |
| WO | WO 03/088897 A2 | 10/2003 |
| WO | WO 2007/043835 A1 | 4/2007 |
| WO | WO 2007/053131 A2 | 5/2007 |
| WO | WO 2008/098374 A1 | 8/2008 |
| WO | WO 2011/061214 A1 | 5/2011 |

OTHER PUBLICATIONS

Bergler, H., et al., "The Enoyl-[acyl-carrier-protein] Reductase (FabI) of *Escherichia Coli*, which Catalyzes a Key Regulatory Step in Fatty Acid Biosynthesis, Accepts NADH and NADPH as Cofactors and is Inhibited by Palmitoyl-CoA", European Journal of Biochemistry, vol. 242, pp. 689-694 (1996).
Bundgaard, H., "Design of Prodrugs: Bioreversible Derivatives for Various Functional Groups and Chemical Entities", Design of Prodrugs, pp. 1-92, Elsevier, New York, Oxford (1985).
Heath, R., et al., "Enoyl-Acyl Carrier Protein Reductdase (fabI) Plays a Determinant Role in Completing Cycles of Fatty Acid Elongation *in Escherichia coli*", The Journal of Biological Chemistry, vol. 270, No. 44, pp. 26538-26542 (1995).
Miller, W., et al., "Discovery of Aminopyridine-Based Inhibitors of Bacterial Enoyl-ACP Reductase (FabI)", Journal of Medicinal Chemistry, vol. 45, pp. 3246-3256 (2002).
European Search Report dated Oct. 29, 2012 for Application No. EP 12180100.
International Search Report dated Sep. 5, 2013 for Application No. PCT/EP2013/06679.

\* cited by examiner

*Primary Examiner* — Bruck Kifle

(57) ABSTRACT

The present invention is related to novel compounds of formula (I) that may inhibit the activity of the FabI enzyme, and which are useful in the treatment of bacterial infections. It further relates to pharmaceutical compositions comprising these compounds, and chemical processes for preparing these compounds.

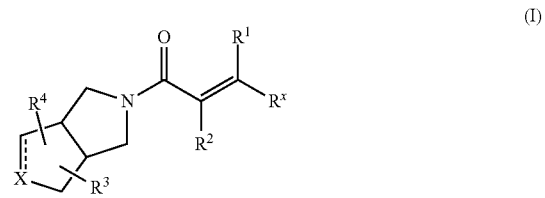

(I)

12 Claims, No Drawings

ANTIBACTERIAL COMPOUNDS

This application is a 35 U.S.C. §371 nationalization of PCT application PCT/EP2013/066679, filed Aug. 9, 2013, which claims priority to application EP No. 12180100.5, filed Aug. 10, 2012.

The present invention is related to novel compounds of formula (I) that inhibit the activity of the FabI enzyme which are therefore useful in the treatment of bacterial infections. It further relates to pharmaceutical compositions comprising these compounds, and chemical processes for preparing these compounds.

The compounds of the present invention are antibacterial compounds that inhibit the FabI protein, a NADH-dependent enoyl-acyl carrier protein (ACP) reductase enzyme in the fatty acid biosynthesis pathway. Fatty acid synthase (FAS) is involved in the overall biosynthetic pathway of saturated fatty acids in all organisms, but the structural organization of FAS varies considerably among them. The distinctive characteristics of FAS of vertebrates and yeasts are that all enzymatic activities are encoded on one or two polypeptide chains, and that the acyl carrier protein (ACP) exists in the form of a complex. In contrast, in bacterial FAS, each of synthetic steps is catalyzed by a distinct, mono-functional enzyme and the ACP is a discrete protein. Therefore, it is possible to selectively inhibit bacterial FAS by blocking one of the synthetic steps using an inhibitory agent. NADH-dependent enoyl-ACP reductase (Fab I) is involved in the last step of the four reaction steps involved in each cycle of bacterial fatty acid biosynthesis. Thus, the FabI enzyme is the biosynthetic enzyme in the overall synthetic pathway of bacterial fatty acid biosynthesis.

The FabI enzyme has been shown to constitute an essential target in major pathogens such as *E. Coli* (Heath et al. *J. Biol. Chem.* 1995, 270, 26538; Bergler et al. *Eur. J. Biochem.* 1996, 242, 689-694). Hence, compounds that inhibit FabI may be useful as antibacterials.

Compounds having FabI enzyme inhibitory activity have been disclosed in WO-01/26652, WO-01/26654, and WO-01/27103. Substituted naphthyridinone compounds having FabI inhibitory activity have been disclosed in WO-03/088897, WO-2007/043835 and WO-2008/098374. International patent application WO 2007/053131 discloses various compounds for potential use as FabI inhibitors. International patent application WO 2011/061214 also discloses various compounds for potential use as FabI inhibitors. However, none of these documents disclose a fused-bicyclic moiety that is directly attached to a carbonyl moiety that is α to an alkene.

The present invention relates to a compound of formula (I)

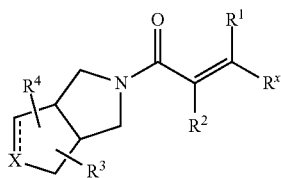

(I)

wherein the ≈≈≈ bond (adjacent X) represents a single bond or a double bond, when ≈≈≈ represents a double bond, then X represents C(R⁴);

when ≈≈≈ represents a single bond, then X represents N(R⁴) or C(R³)(R⁴);

R¹ is hydrogen, $C_{1-4}$alkyl or halo;
R² is hydrogen, $C_{1-4}$alkyl or halo;
R$^x$ represents:

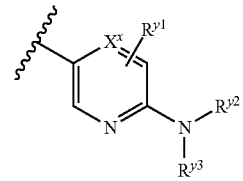

(i)

wherein

X$^x$ represents C(H), C(R$^{y1}$) or N;

R$^{y1}$ represents one to three optional substituents each independently selected from hydrogen, halo, —CN, —O—$C_{1-6}$ alkyl or $C_{1-6}$ alkyl (which latter two alkyl moieties are optionally substituted by one or more fluoro atoms);

each R$^{y2}$ and R$^{y3}$ independently represent hydrogen or -Q¹-R⁵;

each Q¹ independently represents a direct bond or —C(O)—;

R⁵ represents hydrogen, $C_{1-6}$ alkyl, heterocycloalkyl (which latter two groups are each optionally substituted by one or more substituents independently selected from =O and Q²), aryl or heteroaryl (which latter two groups are optionally substituted by one or more substituents selected from Q³);

Q² represents halo, —CN, —O$C_{1-6}$ alkyl (optionally substituted by one or more fluoro atoms), aryl or heteroaryl (which latter two groups are optionally substituted by one or more substituents selected from halo, —CN, $C_{1-3}$ alkyl or —O$C_{1-3}$ alkyl, the latter two alkyl moieties being themselves optionally substituted by fluoro);

Q³ represents halo, —CN, —O—$C_{1-6}$ alkyl or $C_{1-6}$ alkyl (which latter two alkyl moieties are optionally substituted by one or more fluoro substituents);

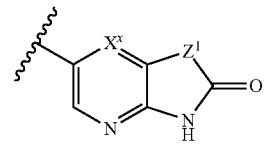

(ii)

wherein

X$^x$ represents C(H) or N;

Z¹ represents —X¹—O—X$^{1a}$—, —X²—N(R$^{z3}$)—X$^{2a}$— or —X³—S—X$^{3a}$—;

X¹, X² and X³ independently represent a direct bond, —C(O)— or —C(R$^{z4}$)(R$^{z5}$)—;

X$^{1a}$, X$^{2a}$ and X$^{3a}$ independently represent a direct bond or —V¹—C(R$^{z1}$)(R$^{z2}$)—;

V¹ represents a direct bond or —C(O)—;

R$^{z1}$, R$^{z2}$, R$^{z3}$, R$^{z4}$ and R$^{z5}$ independently represent hydrogen, $C_{1-6}$ alkyl (optionally substituted by one or more substituents selected from =O and halo) or heterocycloalkyl (optionally substituted by one or more substituents selected from =O, halo and $C_{1-3}$alkyl);

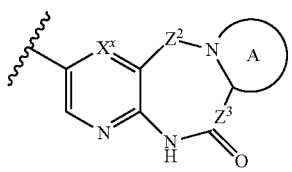

(iii)

wherein $X^x$ represents C(H) or N;

$Z^2$ represents —C($R^{z6}$)($R^{z7}$)— or —C(O)—;

$Z^3$ represents a direct bond (thereby forming a 7-membered ring) or —CH$_2$— (thereby forming an 8-membered ring);

ring A represents a 5- or 6-membered ring optionally containing one, two or three double bonds (and therefore being aromatic or non-aromatic) and optionally containing a further (in addition to the requisite N) one to three (e.g. one or two) heteroatoms (e.g. selected from N and O), and which ring is optionally substituted by one or more substituents each independently selected from =O and $R^{z8}$; each $R^{z6}$, $R^{z7}$ and $R^{z8}$ independently represents hydrogen or $C_{1-6}$ alkyl optionally substituted by one or more substituents selected from =O, —O$C_{1-4}$ alkyl and halo;

each $R^3$ independently represents hydrogen, halo, —O$R^{10}$ or $C_{1-6}$ alkyl (optionally substituted by one or more halo (e.g. fluoro) atoms);

each $R^4$ independently represents hydrogen, halo or -$T^1$-$R^{20}$;

each $T^1$ independently represents a direct bond, —O—, —C(O)—, —C(O)—O—, —O—C(O)—, —C(O)—N($R^{21}$)— or —S(O)$_{n1}$—;

n1 represents 0, 1 or 2;

each $R^{10}$ and each $R^{20}$ independently represents $C_{1-6}$ alkyl (optionally substituted by one or more substituents independently selected from =O and $Y^1$), aryl or heteroaryl (which latter two groups are optionally substituted by one or more substituents independently selected from $Y^2$);

$R^{21}$ represents hydrogen or $C_{1-6}$ alkyl;

each $Y^1$ independently represents halo, —O—$R^{30}$, —CN, aryl or heteroaryl (which latter two groups are optionally substituted by one or more substituents selected from halo, —O—$C_{1-3}$alkyl and $C_{1-3}$ alkyl);

each $Y^2$ independently represents halo, —O$C_{1-6}$alkyl or $C_{1-6}$ alkyl (which latter two alkyl moieties are optionally substituted by one or more fluoro atoms);

each $R^{30}$ independently represents hydrogen, $C_{1-6}$ alkyl (optionally substituted by one or more fluoro atoms), aryl or heteroaryl (which latter two groups are optionally substituted by one or more substituents selected from optionally substituted by one or more substituents selected from halo, —O—$C_{1-3}$alkyl and $C_{1-3}$ alkyl), or a pharmaceutically acceptable salt (e.g. acid addition salt) thereof The above-mentioned compounds of formula (I) (or salts thereof) may be referred to herein as "compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

For the purposes of this invention solvates, prodrugs, N-oxides and stereoisomers of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$O, $^{17}$O, $^{18}$O, $^{32}$P, $^{33}$P, $^{35}$S, $^{18}$F, $^{36}$Cl, $^{123}$I, and $^{125}$I. Certain isotopically-labeled compounds of the present invention (e.g., those labeled with $^3$H and $^{14}$C) are useful in compound and for substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g. between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, non-aromatic pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system.

For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring. Most preferred aryl groups that may be mentioned herein are "phenyl".

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group. Most preferred heteroaryl groups that may be mentioned herein are 5- or 6-membered aromatic groups containing 1, 2 or 3 heteroatoms (e.g. preferably selected from nitrogen, oxygen and sulfur).

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group (e.g. a $C_{1-6}$ alkyl group) may be substituted by one or more substituents (e.g. selected from $Y^1$), then those substituents (e.g. defined by $Y^1$) are independent of one another. That is, such groups may be substituted with the same substituent (e.g. defined by $Y^1$) or different substituents (defined by $Y^1$).

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria.

For the avoidance of doubt, the following compounds of formula (I) (given sub-definitions (Ia), (Ib) and (Ic)) are within the scope of the invention:

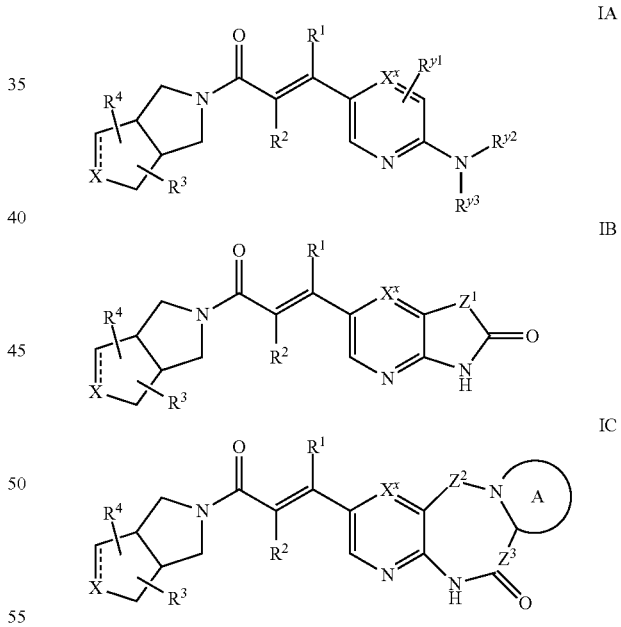

in which the integers are as hereinbefore defined. For the avoidance of doubt that $R^3$ and $R^4$ substituents are optional (given that they are depicted as "floating" and that each can represent hydrogen). When the $R^3$ and $R^4$ group represent a substituent other than hydrogen, then each may be placed at any position on the X-containing ring, including on X itself Preferred compounds of the invention include those in which:
when $R^1$ or $R^2$ represent halo, then they are preferably F or Cl;
more preferably, $R^1$ represents hydrogen or $C_{1-4}$alkyl;
more preferably, $R^2$ represents hydrogen or $C_{1-4}$alkyl.

Compounds of the invention that may be mentioned include those in which, when $R^x$ represents either ring (i), (ii) or (iii), then those rings represent:

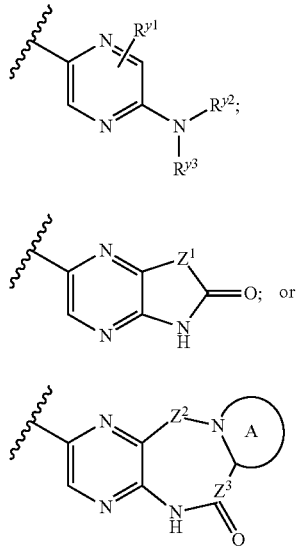

i.e. all are rings in which the monocycle or the first (aromatic) ring of the bicycle or tricycle (which is attached to the remainder of the compound of formula I) contains two nitrogen atoms (in a 1,4-relationship) and wherein the remainder of the integers are as defined herein. However, in an embodiment of the invention (for instance a preferred embodiment), compounds of the invention that may be mentioned include those in which:

when $R^x$ represents either ring (i), (ii) or (iii), then those rings represent

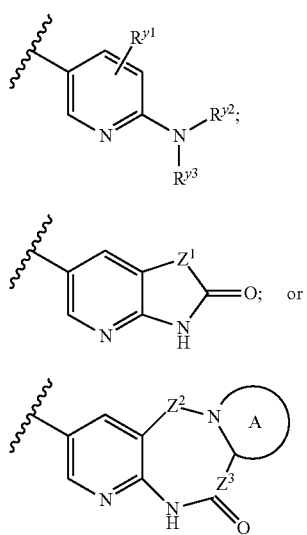

wherein (in each case), the integers are as herein defined. Hence, it is preferred that the rings are those in which $X^x$ represents C.

Preferred compounds of the invention include those in which:
$R^3$ represents hydrogen (or is not present);
the ≡ bond represents a double bond and X represents $C(R^4)$;
the ≡ bond represents a single bond and X represents $N(R^4)$.

Hence, the preferred X-containing rings are:

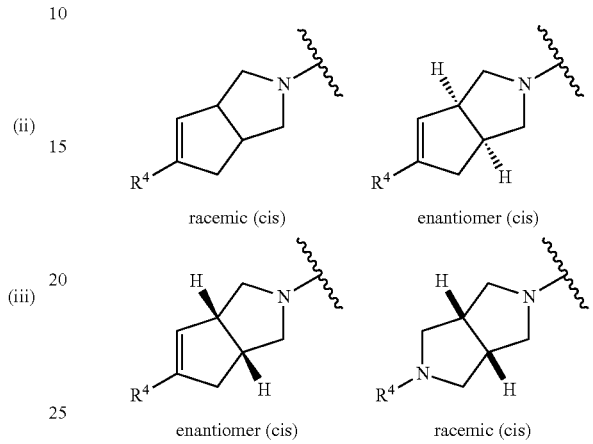

wherein two of the foregoing moieties are racemic and the other two are enantiomers (but in which there is always a cis-relationship at the ring junction), and, in particular, the following are preferred:

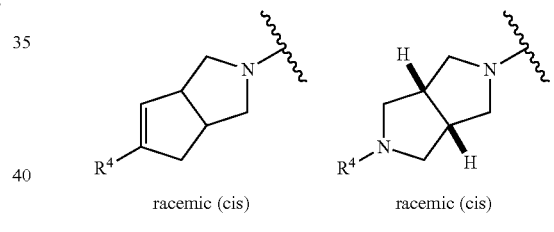

Furthermore, in a separate embodiment of the invention, the following enantiomers of the relevant racemic (cis) X-containing ring are preferred:

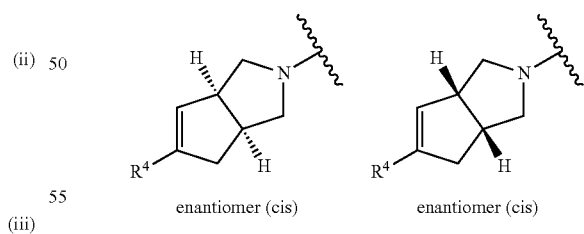

Preferred compounds of the invention hence include those in which:
when X represents $C(R^3)(R^4)$, then $R^3$ represents hydrogen; more preferably, X represents $C(R^4)$ or $N(R^4)$ (and X especially represents $C(R^4)$);
the "floating" $R^3$ represents a substituent on any position of the X-containing ring, e.g. at either position adjacent X;
$R^3$ represents hydrogen, halo, —O—$C_{1-3}$alkyl or $C_{1-3}$ alkyl, or, more preferably $R^3$ represents hydrogen (i.e. is not present);

each $R^{10}$ represents $C_{1-6}$ alkyl (e.g. $C_{1-3}$ alkyl), which may be substituted by one or more halo atoms, but which is preferably unsubstituted;

the "floating" $R^4$ represents a substituent on any position of the X-containing ring, e.g. at either position adjacent X;

when $R^4$ represents a substituent at either position adjacent X, then is it preferably hydrogen, halo, —O—$C_{1-3}$alkyl or $C_{1-3}$ alkyl, however, in this context $R^4$ is preferably hydrogen (i.e. there is no $R^4$ substituent present adjacent X);

when X represents $C(R^3)(R^4)$, $C(R^4)$ or $N(R^4)$ (e.g. when X represents $C(R^4)$ or $N(R^4)$, especially $C(R^4)$), then $R^4$ preferably represents a substituent other than hydrogen (i.e. halo or -$T^1$-$R^{20}$), for example, in this context $R^4$ preferably represents -$T^1$-$R^4$;

it is preferred that there is at least one $R^4$ substituent present that represents -$T^1$-$R^4$ (e.g. it is preferred that X represents $C(R^3)(R^4)$, $C(R^4)$ or $N(R^4)$ (especially $C(R^4)$ or $N(R^4)$)) in which $R^4$ represents -$T^1$-$R^4$.

Preferred compounds of the invention include those in which X represents $C(R^4)$ or $N(R^4)$ (especially $C(R^4)$) and, in this context, $R^4$ represents -$T^1$-$R^{20}$. In this context, it is preferred that:

each $Y^1$ independently represents halo or —O—$C_{1-3}$alkyl (optionally substituted by fluoro);

each $Y^2$ independently represents halo, —O—$C_{1-3}$alkyl or $C_{1-3}$ alkyl (which latter two groups are optionally substituted by fluoro);

each $R^{30}$ independently represents hydrogen or $C_{1-4}$ (e.g. $C_{1-3}$) alkyl;

when $Y^1$ represents aryl or heteroaryl, then these groups preferably represent those hereinbefore defined (e.g. phenyl or a 5- or 6-membered aromatic group containing 1, 2 or 3 heteroatoms), which aryl or heteroaryl groups are optionally substituted by one or more substituents selected from halo, —OCH$_3$ and CH$_3$ (but which are preferably unsubstituted);

$T^1$ represents —O—, —C(O)— or, preferably, a direct bond;

$R^{20}$ may represent (e.g. when X represents $N(R^4)$ and $R^4$ is -$T^1$-$R^{20}$ in which $T^1$ is a direct bond) $C_{1-6}$ alkyl (e.g. containing a double bond, preferably forming e.g. —CH$_2$—CH=CH$_2$);

$R^{20}$ most preferably represents aryl or heteroaryl, both of which are optionally substituted by one or more substituents selected from $Y^2$;

when $R^{20}$ represents aryl, it preferably represents optionally substituted phenyl;

when $R^{20}$ represents heteroaryl, it preferably represents an optionally substituted 5- or 6-membered monocyclic aromatic group containing 1, 2 or 3 heteroatoms.

Preferred $R^{20}$ groups include phenyl and 5- or 6-membered monocyclic heteroaryl groups containing one to four heteroatoms (and preferably containing one or two heteroatoms), so forming for example thienyl, pyridyl, thiazolyl, oxazolyl, isoxazolyl, pyrazolyl or the like. Particularly preferred $R^{20}$ groups include phenyl (e.g. unsubstituted phenyl or methoxyphenyl such as 2-methoxyphenyl), thienyl (e.g. 3-thienyl or 2-thienyl), thiazolyl (e.g. 2-thiazolyl), pyridyl (e.g. 4-pyridyl or 3-pyridyl) and pyrazolyl (e.g. 5-pyrazolyl, such as 1-methyl-5-pyrazolyl).

$R^4$ (when present on $N(R^4)$ may represent $C_{1-6}$ alkyl (e.g. —CH$_2$—CH=CH$_2$), however, most preferred $R^4$ groups (e.g. present on X when X represents $C(R^4)$ or $N(R^4)$) are represented by the following:

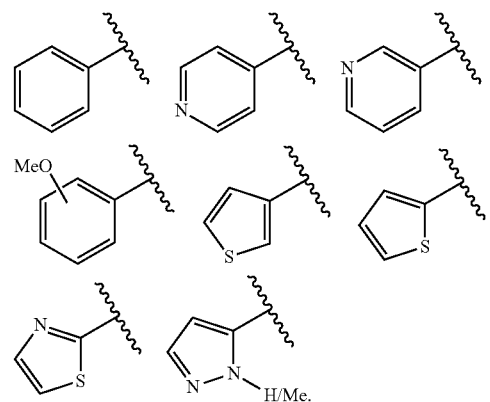

Further preferred compounds of the invention include those in which, for compounds of the invention in which $R^x$ represents option (i):

there are no $R^{y1}$ groups present (i.e. there is one $R^{y1}$ group present that represents hydrogen) or there is one $R^{y1}$ substituent present that represents —CN, —O—$C_{1-6}$ alkyl (e.g. —O—$C_{1-3}$ alkyl such as —OCH$_3$) or $C_{1-6}$ alkyl (e.g. $C_{1-3}$ alkyl such as methyl);

one of $R^{y2}$ and $R^{y3}$ represents hydrogen and the other represents -$Q^1$-$R^5$;

$Q^1$ represents a direct bond or preferably —C(O)—;

$R^5$ represents hydrogen, $C_{1-6}$ alkyl (optionally substituted by one or two (e.g. one) substituent(s) selected from =O and $Q^2$) or aryl or heteroaryl (which latter two groups are optionally substituted by one or two (e.g. one) substituent(s) selected from $Q^3$);

when $R^5$ represents $C_{1-6}$ alkyl, it is preferably unsubstituted (e.g. —CH$_3$) or substituted by one $Q^2$ substituent (and one optional =O substituent, so forming e.g. —(CH$_2$)$_2$—C(O)-$Q^2$);

when $R^5$ represents optionally substituted aryl, then it is preferably phenyl, more preferably unsubstituted phenyl;

when $R^5$ represents optionally substituted heteroaryl, then it is preferably a 5- or 6-membered aromatic group containing 1, 2 or 3 (e.g. one) heteroatom(s) (preferably selected from oxygen, nitrogen and sulfur), so forming for example pyridyl (such as 3-pyridyl, 4-pyridyl or 2-pyridyl) or furanyl (e.g. 3-furanyl);

$Q^2$ represents —O$C_{1-3}$ alkyl or optionally substituted aryl or optionally substituted heteroaryl (e.g. pyridyl, such as 4-pyridyl);

$Q^3$ represents halo (e.g. chloro, fluoro, bromo or iodo), $C_{1-6}$ (e.g. $C_{1-3}$) alkyl (e.g. methyl) or —O$C_{1-6}$ alkyl (e.g. —O$C_{1-3}$ alkyl such as —OCH$_3$).

In a particularly preferred aspect of the invention one of $R^{y2}$ and $R^{y3}$ represents hydrogen and the other represents -$Q^1$-$R^5$, in which:

(i) $R^5$ may represent $C_{1-6}$ alkyl as defined herein. In this aspect of the invention it is particularly preferred that the $C_{1-6}$ alkyl group is substituted with a $Q^2$ group, in which $Q^2$ represents optionally substituted aryl or heteroaryl, as defined herein;

(ii) $R^5$ represents optionally substituted aryl or heteroaryl, as defined herein.

The -$Q^1$-$R^5$ moiety may represent hydrogen (and hence the —N($R^{y2}$)($R^{y3}$) may represent —NH$_2$). However, preferred -$Q^1$- moieties include —C(O)—, and preferred $R^5$ groups include —CH$_3$ and the following groups:

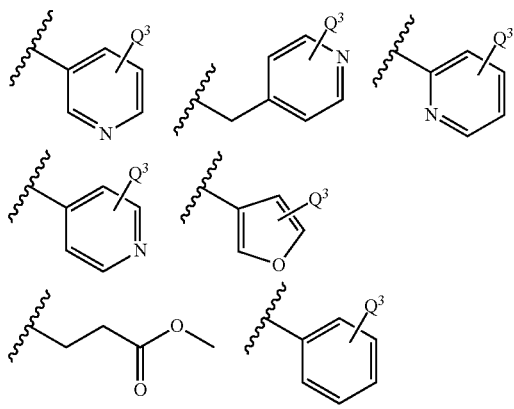

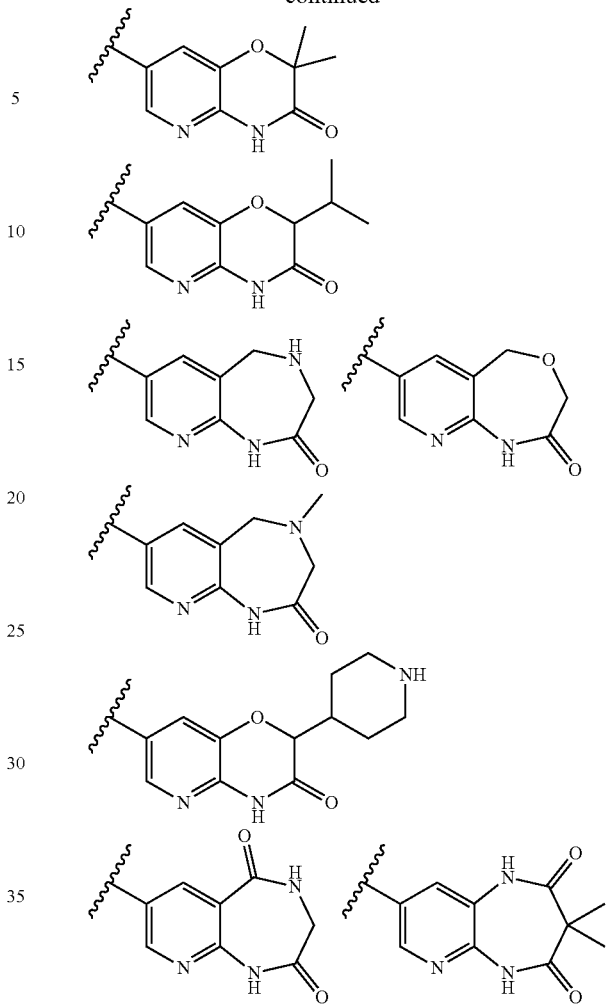

in which the "floating" $Q^3$ substituent represents one or more substituents on the ring, as defined herein by $Q^3$.

In particular, the preferred -$Q^1$-$R^5$ groups are those that contain an aromatic ring.

Further preferred compounds of the invention include those in which, for compounds of the invention in which $R^x$ represents option (ii):

$Z^1$ represents —$X^3$—S—$X^{3a}$— or, more preferably, —$X^1$—O—$X^{1a}$— or —$X^2$—N($R^{z3}$)—$X^{2a}$—;

$X^1$ represents —C($R^{z4}$)($R^{z5}$)— or a direct bond;

$X^{1a}$ represents a direct bond or —C($R^{z1}$)($R^{z2}$)—

$X^2$ represents a direct bond, —C(O) or —C($R^{z4}$)($R^{z5}$)—;

$X^{2a}$ represents —C($R^{z1}$)($R^{z2}$)— or —C(O)—C($R^{z1}$)($R^{z2}$)—;

$Z^1$ represents:
  (i) —$X^1$—O—$X^{1a}$—, in which one of $X^1$ represents —C($R^{z4}$)($R^{z5}$)— and $X^{1a}$ represents a direct bond, or, $X^1$ represents a direct bond and $X^{1a}$ represents —C($R^{z1}$)($R^{z2}$)—;
  (ii) —$X^1$—O—$X^{1a}$— or —$X^2$—N($R^{z3}$)—$X^{2a}$—, in which each of $X^1$ and $X^2$ represents —C($R^{z4}$)($R^{z5}$)— and each of $X^{1a}$ and $X^{2a}$ represents —C($R^{z1}$)($R^{z2}$)—;
  (iii) —$X^2$—N($R^{z3}$)—$X^{2a}$—, in which $X^2$ represents —C(O)— and $X^{2a}$ represents —C($R^{z1}$)($R^{z2}$)—; or
  (iv) —$X^2$—N($R^{z3}$)—$X^{2a}$—, in which $X^2$ represents a direct bond and $X^{2a}$ represents —C(O)—C($R^{z1}$)($R^{z2}$)—;

$R^{z3}$ represents hydrogen or $C_{1-4}$ alkyl (e.g. methyl);

each $R^{z1}$, $R^{z2}$, $R^{z4}$ and $R^{z5}$ independently represents hydrogen, $C_{1-4}$ alkyl (e.g. methyl or isopropyl) or heterocycloalkyl (e.g. a 5- or 6-membered heterocycloalkyl group containing one or two (e.g. one) heteroatoms (preferably selected from nitrogen, oxygen and sulfur), and which is preferably attached via a carbon atom, e.g. unsubstituted 4-piperidinyl);

$Z^1$ preferably represents —CH$_2$—O—, —O—CH$_2$—, —O—C(CH$_3$)$_2$—, —CH$_2$—N(H)—CH$_2$, —CH$_2$—O—CH$_2$—, —CH$_2$—N(CH$_3$)—CH$_2$, —O—C(H)(isopropyl)-, —C(O)—N(H)—CH$_2$, —N(H)—C(O)—C(CH$_3$)$_2$— or —O—C(H)(4-piperidinyl).

When $R^x$ represents option (ii), the preferred groups are

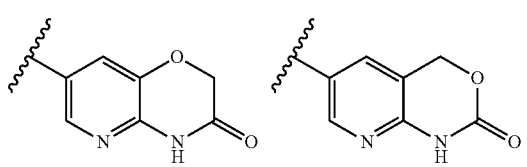

in which the bicycles may be optionally substituted as defined herein. In some structures, optional substituents are depicted (e.g. methyl, isopropyl, piperidinyl), and hence the $R^x$ groups depicted above are preferably of that exact structure (i.e. unsubstituted if depicted as such or substituted with the specific substituents as indicated).

Further preferred compounds of the invention include those in which, for compounds of the invention in which $R^x$ represents option (iii):

$Z^2$ represents —C($R^{z6}$)($R^{z7}$)— or —C(O)—;

$Z^3$ represents a direct bond or —CH$_2$—;

the $Z^2$ and $Z^3$-containing ring is one in which:
  (i) $Z^2$ represents —C($R^{z6}$)($R^{z7}$)— and $Z^3$ represents a direct bond;
  (ii) $Z^2$ represents —C($R^{z6}$)($R^{z7}$)— and $Z^3$ represents —CH$_2$—;
  (iii) $Z^2$ represents —C(O)— and $Z^3$ represents a direct bond;

$R^{z6}$ and $R^{z7}$ independently represent hydrogen;

$R^{z8}$ represents hydrogen (i.e. the A ring is further unsubstituted) or $C_{1-6}$ (e.g. $C_{1-4}$) alkyl (e.g. ethyl) optionally substituted by =O and —O—$C_{1-4}$ alkyl, so forming e.g. a —C(O)—CH$_3$ group, —C(O)—OCH$_2$CH$_3$ group or a —C(O)O-tert-butyl group; the "A" ring is one which preferably represents:
  (i) a 5- or 6-membered heterocycloalkyl group optionally containing one further heteroatom (e.g. nitrogen, oxygen or sulphur), so forming e.g. morpholinyl, thiomorpholinyl, piperidinyl or piperazinyl;

(ii) a 5- or 6-membered heteroaryl ring optionally containing one or two further heteroatoms (e.g. selected from nitrogen, oxygen and sulfur), so forming e.g. imidazolyl, triazolyl (e.g. 1,2,4-triazolyl) or pyrazolyl.

When $R^x$ represents option (iii), the preferred groups are:

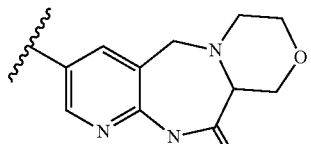

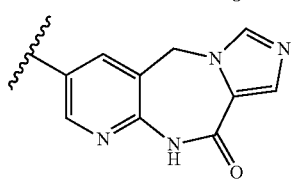

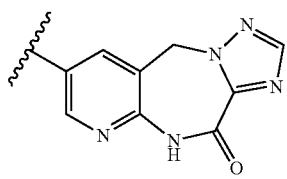 [SMILES: *c1cnc2c(c1)Cn1nccc1C(=O)N2]

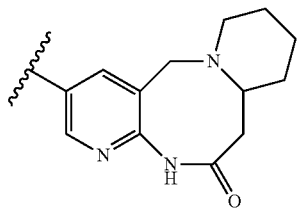

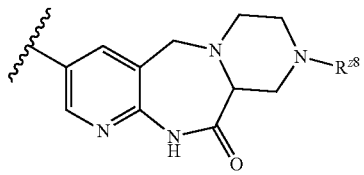

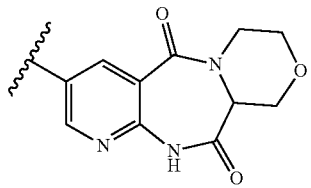

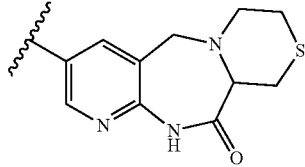

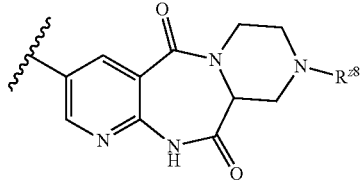

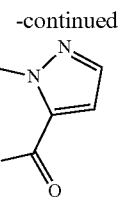

in which the tricycles may be optionally substituted as defined herein. However, preferably the $R^x$ groups are exactly as those depicted above, i.e. further unsubstituted or containing specific substituents as depicted (e.g. by $R^{z8}$).

Compounds of formula (I) may be prepared by:
(i) reaction of a compound of formula (II),

(II)

wherein the dotted line, X, $R^3$ and $R^4$ are as hereinbefore defined, with a compound of formula (III),

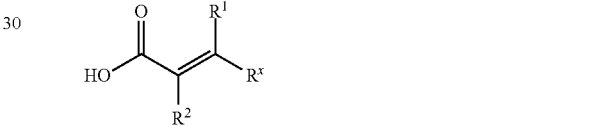

(III)

wherein $R^1$, $R^2$ and $R^x$ are as hereinbefore defined, for example under coupling reaction conditions, for example in the presence of a suitable coupling reagent (e.g. 1,1'-carbonyldiimidazole, N,N'-dicyclohexylcarbodiimide, 1-(3-dimethylaminopropyl)-3-ethylcarbodiimide (or hydrochloride thereof), N,N'-disuccinimidyl carbonate, benzotriazol-1-yl-oxytris(dimethylamino)phosphonium hexafluorophosphate, 2-(1H-benzotriazol-1-yl)-1,1,3,3-tetramethyluronium hexa-fluorophosphate (i.e. O-(1H-benzotriazol-1-yl)-N,N,N',N'-tetramethyluronium hexafluorophosphate), benzotriazol-1-yloxytris-pyrrolidinophosphonium hexa-fluorophosphate, bromo-tris-pyrrolidinophosponium hexafluorophosphate, 2-(1H-benzotriazol-1-yl)-1,1,3,3-tetramethyluronium tetra-fluorocarbonate, 1-cyclohexylcarbodiimide-3-propyloxymethyl polystyrene, O-(7-azabenzotriazol-1-yl)-N,N,N',N'-tetramethyluronium hexafluorophosphate, O-benzotriazol-1-yl-N,N,N',N'-tetramethyluronium tetrafluoroborate), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide and/or lithium diisopropylamide (or variants thereof) and an appropriate solvent (e.g. tetrahydrofuran, pyridine, toluene, dichloromethane, chloroform, acetonitrile, dimethylformamide, trifluoromethylbenzene, dioxane or triethylamine). Such reactions may be performed in the presence of a further additive such as 1-hydroxybenzotriazole hydrate. Alternatively, a carboxylic acid group may be converted under standard conditions to the corresponding acyl chloride (e.g. in the presence of SOCl$_2$ or oxalyl chloride), which acyl chloride is then reacted with a compound of formula (II), for example under similar conditions to those mentioned above. Alternatively still, when a carboxylic acid ester group is converted to a carboxylic acid amide, the reaction may be performed in the presence of a suitable reagent such as trimethylaluminium (and the relevant compound of formula (II));

(ii) reaction of a compound of formula (IV),

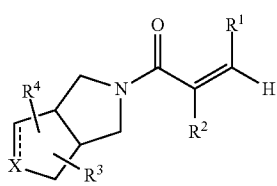

wherein the dotted line, X, R$^3$, R$^4$, R$^1$ and R$^2$ are as hereinbefore defined, with a compound of formula (V),

wherein X$^{a1}$ represents a suitable leaving group, such as a suitable halo group (e.g. chloro, iodo and, especially, bromo), under reaction suitable reaction conditions, for example under metal catalyst coupling reaction conditions (e.g. precious metal coupling reaction conditions, wherein the precious metal is e.g. palladium-based), in particular under Heck reaction conditions using preferably a palladium-based catalyst such as palladium acetate, tetrakis(triphenylphosphione)palladium(0), bis(triphenylphosphine)-palladium(II) dichloride, [1,1'-bis(diphenylphosphino)ferrocene]-palladium(II) dichloride or the like (preferably, the catalyst is palladium acetate), for instance optionally in the presence of a suitable solvent (e.g. acetonitrile or the like), base (e.g. an amine base such as N,N-diispropyl-amine or the like), and a ligand (e.g. triphenylphosphine, tri-O-tolylphosphine or the like). The reaction may be performed in a sealed tube and/or in a microwave;

(iii) modification of existing compounds of formula (I), for example by conversions of/to standard function groups (e.g. conversion of a —N(H)— moiety to a —N(—C(O)-alkyl)-moiety by acylation, etc).

Compounds of formula (II) in which the bond adjacent X is a double bond, X represents C(R$^4$) and R$^4$ is an aromatic group may be prepared by reaction of a compound of formula (VI),

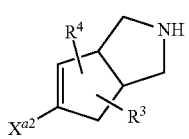

or a protected derivative thereof (e.g. an amino-protected derivative, e.g. —N-Boc derivative), wherein X$^{a2}$ represents a suitable leaving group, such as such as iodo, bromo, chloro or a sulfonate group (e.g. —OS(O)$_2$CF$_3$, a nonaflate or the like), and R$^3$ and R$^4$ are as hereinbefore defined, with a compound of formula (VII),

Ar—X$^{a3}$                 (VII)

wherein Ar represents an aromatic group (aryl or heteroaryl) that R$^4$ may represent, and X$^{a3}$ represents a suitable group, such as —B(OH)$_2$, —B(OR$^{wx}$)$_2$ or —Sn(R$^{wx}$)$_3$, in which each R$^{wx}$ independently represents a C$_{1-6}$ alkyl group, or, in the case of —B(OR$^{wx}$)$_2$, the respective R$^{wx}$ groups may be linked together to form a 4- to 6-membered cyclic group (such as a 4,4,5,5-tetramethyl-1,3,2-dioxaborolan-2-yl group), thereby forming e.g. a pinacolato boronate ester group. The reaction may be performed in the presence of a suitable catalyst system, e.g. a metal (or a salt or complex thereof) such as Pd, CuI, Pd/C, PdCl$_2$, Pd(OAc)$_2$, Pd(Ph$_3$P)$_2$Cl$_2$, Pd(Ph$_3$P)$_4$ (i.e. palladium tetrakistriphenylphosphine), Pd$_2$(dba)$_3$ and/or NiCl$_2$ (preferred catalysts include palladium) and optionally a ligand such as PdCl$_2$(dppf).DCM, t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof, together with a suitable base such as, Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK (or mixtures thereof; preferred bases include Na$_2$CO$_3$ and K$_2$CO$_3$) in a suitable solvent such as dioxane, toluene, ethanol, dimethylformamide, dimethoxyethane, ethylene glycol dimethyl ether, water, dimethylsulfoxide, acetonitrile, dimethylacetamide, N-methylpyrrolidinone, tetrahydrofuran or mixtures thereof (preferred solvents include dimethylformamide and dimethoxyethane). The reaction may be carried out for example at room temperature or above (e.g. at a high temperature such as at about the reflux temperature of the solvent system). The reaction may be carried out at elevated temperature in a closed reactor or microwave.

Compounds of formula (III) may be prepared by reaction of a compound of formula (VIII),

or a derivative thereof (e.g. an ester thereof such as —C(O)O-tert-butyl), wherein R$^1$ and R$^2$ are as hereinbefore defined, with a compound of formula (V) as hereinbefore defined, for example under reaction conditions such as those hereinbefore described above (preparation of compounds of formula (I), process step (ii)), e.g. DIPEA, Pd(OAc)$_2$, tri-O-tolylphosphine.

Compounds of formula (IV) may be prepared by reaction of a compound of formula (II) as hereinbefore defined, with a compound of formula (IX),

wherein $X^{a4}$ represents a suitable leaving group, e.g. a sulfonate, chloro, iodo or bromo (especially chloro), under standard reaction conditions, such as an in presence of a suitable base (e.g. amine base such as triethylamine) and a suitable solvent (e.g. dichloromethane).

Compounds of formula V in which $R^x$ represents ring (i) and $X^x$ represents N may be prepared by reaction of a compound of formula (IXA),

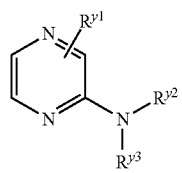
(IXA)

wherein $R^{y2}$ and $R^{y3}$ are as hereinbefore defined (e.g. both represent hydrogen), and $R^{y1}$ is as hereinbefore defined (e.g. there is one $R^{y1}$ substituent α to the —N($R^{y2}$)($R^{y3}$) group, for instance in which $R^{y1}$ represents —COO-ethyl), by halogenation, for instance by reaction in the presence of a suitable halide source, e.g. a source of bromide ions includes N-bromosuccinimide (NBS) and bromine, a source of iodide ions includes iodine, diiodoethane, diiodotetrachloroethane or, preferably, N-iodosuccinimide, and a source of chloride ions includes N-chlorosuccinimide, chlorine and iodine monochloride, for instance in the presence of a suitable solvent such as acetonitrile (e.g. NBS in the presence of a suitable solvent such as acetonitrile).

Compounds of formula (V) in which $R^x$ represents option (ii), i.e. the bicycle as hereinbefore defined, may be prepared by intramolecular cyclisation of a compound of formula (X),

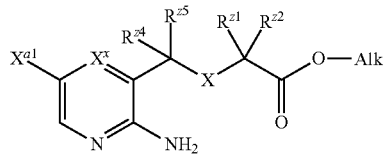
(X)

wherein "Alk" represents a alkyl group (e.g. $C_{1-6}$ alkyl such as ethyl), X represents —O— or —N($R^{z3}$)—, and the remaining integers ($X^x$, $X^{a1}$, $R^{z1}$, $R^{z2}$, $R^{z3}$, $R^{z4}$ and $R^{z5}$ are as hereinbefore defined), for example under reaction conditions for instance in the presence of a suitable base (e.g. NaH) and suitable solvent (e.g. DMF).

Compounds of formula (V) in which $R^x$ represents option (ii), i.e. a bicycle, in which $X^1$ and $X^2$ represent a direct bond, may be prepared by reaction of a compound of formula (XI),

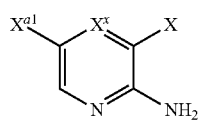
(XI)

wherein the integers are as hereinbefore defined, with a compound of formula (XII),

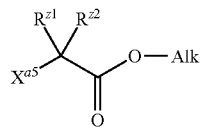
(XII)

wherein $X^{a5}$ represents a suitable leaving group such as chloro, iodo or bromo (especially bromo) and the other integers ($R^{z1}$, $R^{z2}$ and Alk) are as hereinbefore defined, for example under reaction conditions for instance in the presence of a suitable base (e.g. NaH) and suitable solvent (e.g. DMF). Corresponding compounds of formula (V) in which $X^{a1}$ is not present (i.e. represents hydrogen) may also be prepared accordingly (from corresponding compounds of formula (XI) in which $X^{a1}$ is not present, i.e. represents hydrogen).

Compounds of formula (V) in which $X^{a1}$ represents halo (e.g. bromo) may be prepared by reaction of a compound corresponding to a compound of formula (V) but in which $X^{a1}$ represents hydrogen, under appropriate reaction conditions, e.g. those that contain a source of halide (e.g. bromide) ions, for instance an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride, for instance in the presence of a suitable solvent.

Compounds of formula (V) in which $R^x$ is option (iii), i.e. a tricycle (e.g. in which $Z^3$ is a direct bond), may be prepared by intramolecular cyclisation of a compound of formula (XII),

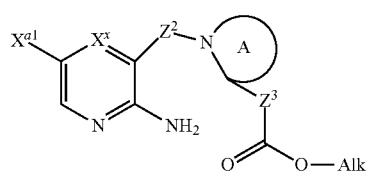
(XII)

wherein the integers are as hereinbefore defined, for example under reaction conditions for instance in the presence of a suitable base (e.g. NaH) and suitable solvent (e.g. DMF).

Compounds of formula (VI) in which $X^{a2}$ represents —O—S(O)$_2$CF$_3$ may be prepared by reaction of by reaction of a compound of formula (XIII),

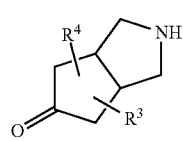
(XIII)

or a protected derivative thereof, for instance by reaction in the presence of a suitable base (e.g. an amine base, such as LDA, or the like), which may be prepared first and the compound of formula (XIII) may be added to it, in e.g. the presence of an inert solvent (e.g. a dry polar aprotic solvent, such as dry THF) at low temperature (e.g. at about −78° C.), followed by addition of N-phenyl-trifluoromethane sulfonimide or the like.

Compounds of formula (X) may be prepared by reaction of a compound of formula (XIV),

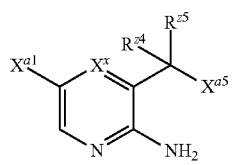

wherein $X^{a5}$ represents a suitable leaving group, such as bromo, chloro or iodo (especially bromo), and the other integers are as hereinbefore defined, with a compound of formula (XV),

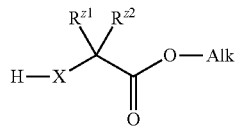

wherein the integers are as hereinbefore defined, under conditions for instance the presence of a suitable base (e.g. an amine base, such as triethylamine) and a suitable solvent (e.g. DMF), which reaction may be performed at elevated temperature e.g. in a sealed tube and/or in a microwave.

Compounds of formula (XII) may be prepared for example under similar conditions to those described in respect of preparation of compounds of formula (X) (i.e. reaction of a compound of formula (XIV) with a compound of formula (XV)), but wherein the "—X—H" moiety (e.g. amino moiety) of the compound of formula (XV) corresponds to the —N(H)— moiety of the "A" ring for the preparation of compounds of formula (XII).

Compounds of formula (XIII) may be prepared by reduction of the double bond of the corresponding enone.

Certain intermediate compounds may be commercially available, may be known in the literature, or may be obtained either by analogy with the processes described herein, or by conventional synthetic procedures, in accordance with standard techniques, from available starting materials using appropriate reagents and reaction conditions.

Certain substituents on/in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations.

Compounds of the invention may be isolated from their reaction mixtures using conventional techniques (e.g. recrystallisations, where possible under standard conditions).

It will be appreciated by those skilled in the art that, in the processes described above and hereinafter, the functional groups of intermediate compounds may need to be protected by protecting groups.

The need for such protection will vary depending on the nature of the remote functionality and the conditions of the preparation methods (and the need can be readily determined by one skilled in the art). Suitable amino-protecting groups include acetyl, trifluoroacetyl, t-butoxycarbonyl (BOC), benzyloxycarbonyl (CBz), 9-fluorenyl-methyleneoxycarbonyl (Fmoc) and 2,4,4-trimethylpentan-2-yl (which may be deprotected by reaction in the presence of an acid, e.g. HCl in water/alcohol (e.g. MeOH)) or the like. The need for such protection is readily determined by one skilled in the art. For example the a —C(O)O-tert-butyl ester moiety may serve as a protecting group for a —C(O)OH moiety, and hence the former may be converted to the latter for instance by reaction in the presence of a mild acid (e.g. TFA, or the like).

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", $3^{rd}$ edition, T. W. Greene & P. G. M. Wutz, Wiley-Interscience (1999).

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds described herein are inhibitors of the FabI enzyme, as demonstrated in by the examples herein. In view of these FabI enzyme inhibiting properties the compounds described herein may therefore be useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Additionally, the compounds may be useful in combination with known antibiotics.

Therefore the present invention also relates to compounds of the invention for use as a medicine especially for use in treating bacterial infections, in particular bacterial infections caused by a bacterium that expresses a FabI enzyme. Subsequently the present compounds may be used for the manufacture of a medicine for treatment of bacterial infections, in particular bacterial infections caused by a bacterium that expresses a FabI enzyme.

Further, the present invention provides a method of treating bacterial infections which comprises administering to a subject in need thereof a FabI enzyme inhibiting compound of the invention.

A subject in need of treatment has a bacterial infection or has been exposed to an infectious bacterium, the symptoms of which may be alleviated by administering a therapeutically effective amount of the compounds of the present invention. For example, a subject in need of treatment can have an infection for which the compounds of the invention can be administered as a treatment. In another example, a subject in need of treatment can have an open wound or burn injury, for which the compounds of the invention can be administered as a prophylactic. Typically a subject will be treated for an existing bacterial infection.

A subject can have a bacterial infection caused by *Bacillus anthracis, Citrobacter* sp., *Escherichia coli, Francisella tularensis, Haemophilus* influenza, *Listeria* mono-cytogenes, *Moraxella catarrhalis, Mycobacterium tuberculosis, Neisseria meningitidis, Proteus mirabilis, Proteus vulgaris, Salmonella* sp., *Serratia* sp., *Shigella* sp., *Stenotrophomonas maltophilia, Staphylococcus aureus*, or *Staphylococcus epidermidis*. Preferably, the subject is treated (prophylactically or therapeutically) for a bacterial infection caused by a bacterium that expresses a FabI enzyme.

The term "treating" and 'treatment', as used herein, refers to curative, palliative and prophylactic treatment, including reversing, alleviating, inhibiting the progress of, or preventing the disease, disorder or condition to which such term applies, or one or more symptoms of such disease, disorder or condition.

A "therapeutically effective amount" of a compound of the present invention is the quantity which, when administered to a subject in need of treatment, improves the prognosis of the subject, e.g. delays the onset of and/or reduces the severity of one or more of the subject's symptoms associated with a bacterial infection. The amount of the disclosed compound to be administered to a subject will depend on the particular disease, the mode of administration, and the characteristics of the subject, such as general health, other diseases, age, sex, genotype, body weight and tolerance to drugs.

The skilled person will be able to determine appropriate dosages depending on these and other factors.

The compounds may be tested in one of several biological assays to determine the concentration of compound which is required to have a given pharmacological effect.

Additionally the present invention provides pharmaceutical compositions comprising at least one pharmaceutically acceptable carrier and a therapeutically effective amount of a compound of the invention.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or *acacia*), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of the invention may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of the invention may also be formulated in rectal compositions such as suppositories or retention enemas, e.g. containing conventional suppository bases such as cocoa butter and/or other glycerides.

Those of skill in the treatment of antibacterial diseases linked to the inhibition of the FabI enzyme will easily determine the therapeutically effective amount of a compound of the invention from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular compound of the invention used, the particular condition being treated, the severity of the condition being treated, the age, weight and general physical condition of the particular patient as well as the other medication, the patient may be taking, as is well known to those skilled in the art.

Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Compounds of the invention/formula (I) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

For instance, compounds of the invention/formula (I) may have the advantage that they have a good or an improved thermodynamic solubility (e.g. compared to compounds known in the prior art; and for instance as determined by a known method and/or a method described herein). Compounds of the invention/formula (I) may also have the advantage that they have a broad spectrum of activity against antibacterials (e.g. a broader spectrum of antibacterial activity compared to compounds known in the prior art; and for instance as determined by known tests and/or tests described herein). Compounds of the invention/formula (I) may also have the advantage that they have good or improved in vivo pharmacokinetics and oral bioavailability. They may also have the advantage that they have good or improved in vivo efficacy. For instance, the compounds of the invention may adaptable for intravenous formulation/dosing and hence may exhibit an improved in vivo efficacy when administered intravenously.

Experimental Part

Abbreviations

"DMF" is defined as N,N-dimethylformamide, "DCM" or "CH$_2$Cl$_2$" is defined as dichloromethane, "MeOH" is defined as methanol, "EtOH" is defined as ethanol, "MgSO$_4$" is defined as magnesium sulfate, and "THF" is defined as tetrahydrofuran, "AcOEt" or "EtOAc" is defined as ethyl acetate, "DIPEA" is defined as diisopropylethylamine, "EDCI" is defined as N'-(ethylcarbonimidoyl)-N,N-dimethyl-1,3-propanediamine monohydrochloride, "HOBT" is defined as 1-hydroxy-1H-benzotriazole, "DIPA" is defined as diisopropylamine, "K$_2$CO$_3$" is defined as potassium carbonate, "TFA" is defined as trifluoroacetic acid, "NH$_4$OH" is defined as ammonium hydroxide, "NaHCO$_3$" is defined as carbonic acid monosodium salt, "Et$_2$O" is defined as diethyl ether, "Na$_2$SO$_4$" is defined as sulfuric acid disodium salt, "CH$_3$CN" is defined as acetonitrile, "NaOH" is defined as sodium hydroxide, "n-BuLi" is defined as n-Butyllithium, "i-PrOH" is defined as isopropanol, "Pd(OAc)$_2$" is defined as palladium acetate, "DMA" is defined as dimethylacetamide, "Et$_3$N" is defined as triethylamine, SFC is defined as Supercritical Fluid Chromatography.

Stereochemical Representation

The compounds of formula (I) have at least two asymmetric carbon atoms as illustrated below wherein the asymmetric carbon atoms are identified by a *:

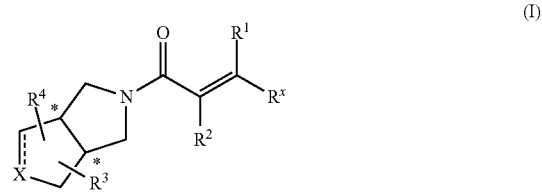

(I)

Due to ring tension in the system of two annulated five membered rings, only the 'cis' forms can be prepared and not the 'trans' forms.

Compounds of formula (I) wherein the system of two annulated five membered rings has the 'cis'-configuration.

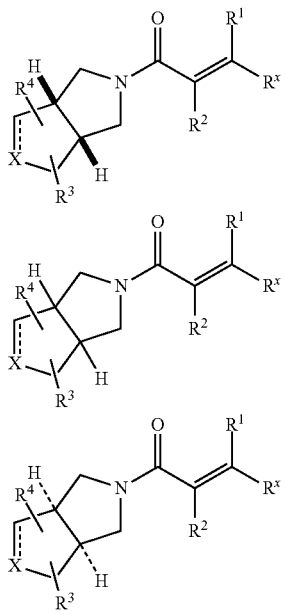

Each of the above depicted "cis" compounds consists of a racemic mixture of two enantiomers and bold bonds or hashed bonds have been used to indicate this relative stereochemical configuration.

In case such a "cis" compound was separated into its two individual enantiomers, the stereochemical configuration of the single enantiomer was than designated as R* or S* indicating a relative stereochemistry. Accordingly a single enantiomer designated as (R*,S*) can either have the absolute (R,S) configuration or the (S,R) configuration. If the absolute stereochemistry of a specific chiral carbon atom in a single enantiomer was known the bold and hashed bonds were replaced by wedged bonds to indicate the compound is a single enantiomer having a known absolute stereochemistry.

The same principles apply to fused rings of that $R^x$ may represent.

SYNTHESIS OF EXAMPLES

Synthesis of Final Compounds in which $R^x$ Represents Ring (i):
Synthesis of Final Compounds C

Example A

Preparation of Intermediate A

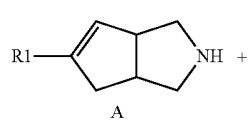

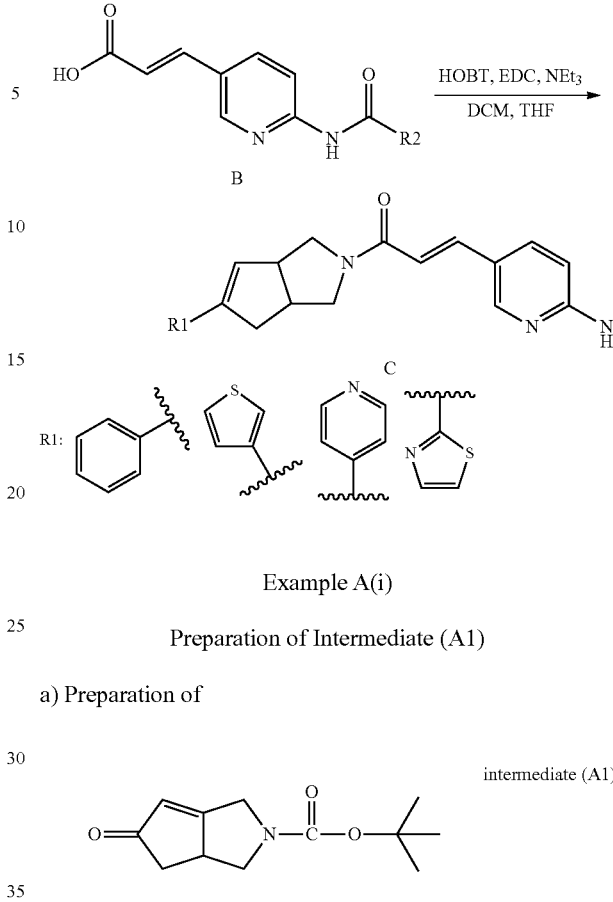

Example A(i)

Preparation of Intermediate (A1)

a) Preparation of intermediate (A1)

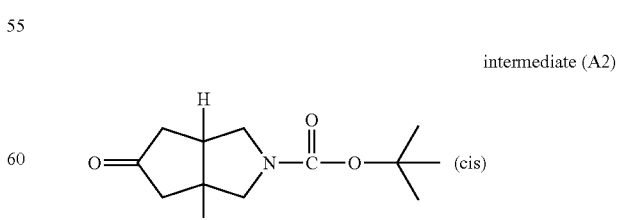

A solution of allyl-prop-2-ynyl-carbamic acid tert-butyl ester (CAS 147528-20-9, 45 g, 0.23 mol), cobalt carbonyl (17.5 g, 46.1 mmol) and 1,1,3,3-tetramethyl-2-thiourea (36.6 g, 0.277 mol) in toluene (1.8 L) was stirred and heated at 70° C. for 5 hours in an autoclave under CO pressure (2-3 bar). The resulting mixture was filtered through a short pad of celite and evaporated till dryness. The residue was taken up in DCM and filtered through a short pad of celite in order to obtain a clear solution. It was evaporated till dryness to give 85.7 g of crude residue. It was purified by preparative liquid chromatography on (silicagel 20-45 μm, 1000 g, mobile phase (gradient DCM/AcOEt from 95/5 to 80/20). Pure fractions were collected and the solvent was evaporated to give 36.5 g of intermediate (A1).

Preparation of Intermediate (A2)

b) Preparation of intermediate (A2)

A mixture of intermediate (A1) (37.6 g, 0.168 mol) and palladium 10% on charcoal (7.5 g) in ethyl acetate (750 ml) was hydrogenated at room temperature for 30 minutes at 3 bars in a closed vessel reactor. The resulting mixture was filtered through a short pad of celite and evaporated till dryness to give 38.2 g of intermediate (A2).

Preparation of Intermediate (A3)

c) Preparation of

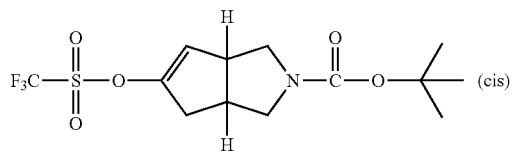

intermediate (A3)

n-BuLi 1.6M in hexane (64 ml, 0.102 mol) was added drop wise at −20° C., under a $N_2$ atmosphere, to a solution of diisopropylamine (14.3 ml, 0.102 mol) in dry THF (140 mL) then the mixture was stirred at −20° C. for 20 minutes. A solution of intermediate (A2) (19.1 g, 84.8 mmol) in dry THF (190 mL) was then added at −78° C. and the resulting mixture was stirred for 1 hour at −78° C. A solution of N-phenyltrifluoromethane sulfonimide (36.4 g, 0.102 mol) in dry THF (110 mL) was added at −78° C. then the mixture was allowed to reach room temperature and stirred overnight. The mixture was evaporated till dryness. The residue was taken in DCM, washed with an aqueous $NaHCO_3$ solution, dried ($MgSO_4$) and evaporated till dryness to give 27.7 g of intermediate (A3).

Preparation of Intermediate (A4)

d) Preparation of

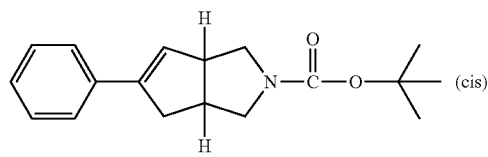

intermediate (A4)

A solution of intermediate (A3) (9.3 g, 26.0 mmol) and phenyl boronic acid (3.81 g, 31.2 mmol) in a solution of potassium carbonate 2 M (26 ml) and ethylene glycol dimethyl ether (93 ml) was purged with $N_2$ for 10 minutes then tetrakistriphenyl-phosphine-palladium (3.0 g, 2.6 mmol) was added. The closed reactor was heated at 80° C. using one multimode cavity microwave CEM Mars system with a power output ranging from 0 to 400 W for 30 minutes. The resulting solution was cooled down to room temperature, water and EtOAc were added, the organic layer was separated, washed with water then brine, dried ($MgSO_4$) and evaporated till dryness. Purification of the residue was carried out by flash chromatography over silica gel (330 g, 15-40 µm, heptane/EtOAc from 100/0 to 80/20). The pure fractions were collected and evaporated to dryness to afford 4.3 g of intermediate (A4).

Preparation of Intermediate (A5)

e) Preparation of

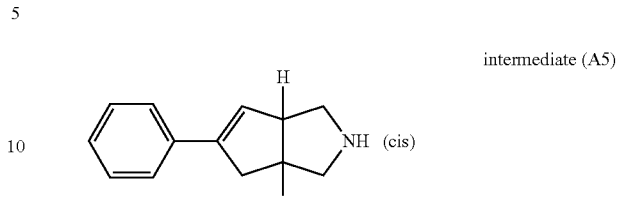

intermediate (A5)

Trifluoroacetic acid (44 ml) was added drop wise to a solution of intermediate (A4) (14.5 g, 50.8 mmol) in $CH_2Cl_2$ (44 ml). The resulting solution was stirred at room temperature for 30 min then the mixture was cooled to 5° C. NaOH 3N was added slowly until the mixture was basic, it was extracted twice with $CH_2Cl_2$. The combined organic layer were washed with NaOH 3N then water, dried over $MgSO_4$ and evaporated to give 8.8 g of racemic compound of intermediate (A5).

Preparation of Intermediate (A6) and (A7)

f) Preparation of

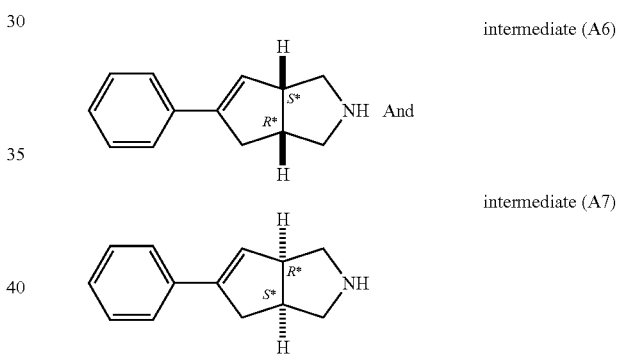

Intermediate (A5) was purified and resolved by chiral SFC on (CHIRALPAK AD-H 5 µm 250×20 mm) Mobile phase (0.3% isopropylamine, 73% $CO_2$, 27% iPrOH). Pure fractions were collected and the solvent was removed to give 3.9 g of intermediate (A7) (R*,S*) ($[\alpha]_D^{20}$=−53.19° (589 nm, c 0.3365 w/v %, DMF, 20° C.)) and 4 g of intermediate (A6) (S*,R*) ($[\alpha]_D^{20}$=+38.6° (589 nm, c 0.285 w/v %, DMF, 20° C.)).

Intermediate (A6)

$^1$H NMR (400 MHz, DMSO-$d_6$) δ (ppm) 7.43 (d, J=7.6 Hz, 2H), 7.32 (t, J=7.6 Hz, 2H), 7.20-7.26 (m, 1H), 6.07 (d, J=2.0 Hz, 1H), 3.30-3.39 (m, 1H), 2.77-2.94 (m, 4H), 2.66 (dd, J=3.0, 11.1 Hz, 1H), 2.58 (dd, J=3.0, 11.1 Hz, 1H), 2.46 (d, J=15.7 Hz, 1H).

Intermediate (A7)

$^1$H-NMR (400 MHz, DMSO-$d_6$) δ (ppm) 7.43 (d, J=7.6 Hz, 2H), 7.32 (t, J=7.6 Hz, 2H), 7.20-7.26 (m, 1H), 6.07 (d, J=2.0 Hz, 1H), 3.30-3.39 (m, 1H), 2.77-2.94 (m, 4H), 2.66 (dd, J=3.0, 11.1 Hz, 1H), 2.58 (dd, J=3.0, 11.1 Hz, 1H), 2.46 (d, J=15.7 Hz, 1H).

Example A(ii)

Preparation of Intermediate (A8)

a) Preparation of

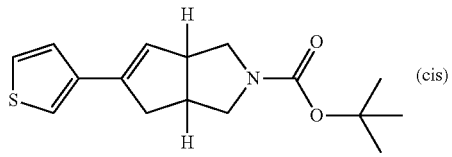
intermediate (A8)

A solution of intermediate (A3) (44.4 g, 111.82 mmol) and 3-thiopheneboronic acid (17.17 g, 134.19 mmol) in potassium carbonate 2M (112 ml) and ethylene glycol dimethyl ether (444 ml), in an open vessel, was purged with $N_2$ for 10 minutes then tetrakistriphenylphosphinepalladium (12.92 g, 223.65 mmol) was added. The solution was heated at 78° C. using one multimode cavity microwave CEM MARS system with a power output ranging from 0 to 400 W for 1 hour. The solution was cooled to room temperature, water and EtOAc were added. The mixture was filtered through a pad of celite. The organic layer was separated, washed with water then brine, dried over $MgSO_4$ and evaporated till dryness. The residue was purified by preparative liquid chromatography on (silicagel 20-45 μm, 1000 g, mobile phase (80% heptane, 20% AcOEt)). The pure fractions were collected and concentrated to give 16 g of intermediate (A8).

b) Preparation of

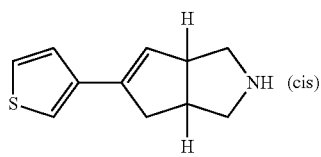
intermediate (A9)

Trifluoroacetic acid (14.37 ml, 186.47 mmol) was added to a solution of intermediate (A8) (5.72 g, 18.65 mmol) in $CH_2Cl_2$ (57 ml). The reaction mixture was stirred at room temperature for 3 hours. $K_2CO_3$ (10% aqueous solution, 50 ml) and then $K_2CO_3$ solid were added at 0° C. to basify the solution. The organic layer was separated, washed with water, dried ($MgSO_4$) and evaporated till dryness. The residue was purified by preparative liquid chromatography on (silicagel 20-45 μm, 1000 g, mobile phase (1% $NH_4OH$, 93% DCM, 7% MeOH)). The pure fractions were collected and concentrated to give 12 g of intermediate (A9).

c) Preparation of

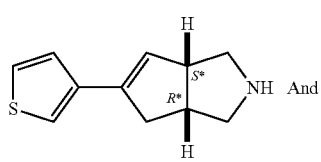
intermediate (A10)

And

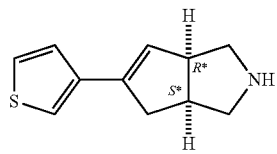
intermediate (A11)

Intermediate (A9) was purified and resolved by chiral SFC on (CHIRALPAK AD-H 5 μm 250×20 mm) Mobile phase (0.3% isopropylamine, 80% $CO_2$, 20% methanol). Pure fractions were collected and the solvent was removed to give 5.8 g of intermediate (A11) (R*,S*) ($[\alpha]_D^{20}$=−12.4° (589 μm, c 0.5 w/v %, DCM, 20° C.)) and 5.6 g of intermediate (A10) (S*,R*) ($[\alpha]_D^{20}$+9.43° (589 μm, c 0.35 w/v %, DCM, 20° C.)).

Intermediate (A10)

$^1$H NMR (500 MHz, DMSO-$d_6$) δ (ppm) 7.49 (dd, J=2.5, 5.0 Hz, 1H), 7.31 (d, J=5.0 Hz, 1H), 7.29 (d, J=2.5 Hz, 1H), 5.88 (d, J=1.9 Hz, 1H), 3.28-3.33 (br.s., 1H), 2.75-2.87 (m, 4H), 2.61 (dd, J=2.8, 10.7 Hz, 1H), 2.54 (dd, J=3.3, 10.9 Hz, 1H), 2.40-2.15 (m, 2H).

Intermediate (A11)

$^1$H NMR (500 MHz, DMSO-$d_6$) δ (ppm) 7.49 (dd, J=2.5, 5.0 Hz, 1H), 7.31 (d, J=5.0 Hz, 1H), 7.29 (d, J=2.5 Hz, 1H), 5.88 (d, J=1.9 Hz, 1H), 3.28-3.33 (br.s., 1H), 2.75-2.87 (m, 4H), 2.61 (dd, J=2.8, 10.7 Hz, 1H), 2.54 (dd, J=3.3, 10.9 Hz, 1H), 2.40-2.15 (m, 2H).

Example A(iii)

Preparation of Intermediate (A12)

a) Preparation of

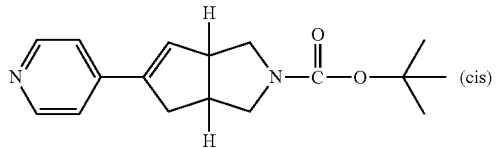
intermediate (A12)

A solution of intermediate (A3) (108 g, 0.302 mol) and pyridine-4-boronic acid (49.5 g, 0.363 mol) in aqueous potassium carbonate 2M (302 ml, 0.604 mol) and ethylene glycol dimethyl ether (1.1 L) was purged with $N_2$ for 5 minutes then tetrakistriphenylphosphinepalladium (34.9 g, 0.030 mol) was added, the mixture was heated at 78° C. using a multimode microwave (CEM Mars 5) with a power output ranging from 0 to 800 W for 1 hour, cooled to room temperature, water and EtOAc were added, the organic layer was separated, washed with water then brine, dried over $MgSO_4$ and evaporated till dryness. The residue was purified by preparative liquid chromatography on (silicagel 15-40 μm, 300 g, mobile phase (0.1% $NH_4OH$, 97% DCM, 3% iPrOH). Pure fractions were collected and the solvent was removed to obtain 47.6 g of intermediate (A12).

b) Preparation of

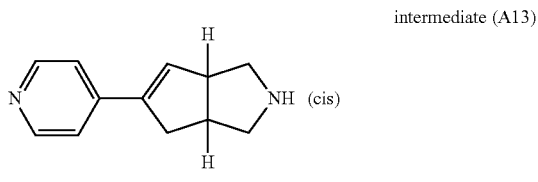 [SMILES: C1=C(c2ccncc2)CC2CNCC12]

intermediate (A13)

Intermediate (A12) was deprotected in accordance with the techniques described herein, in order to obtain Intermediate (A13).

c) Preparation of

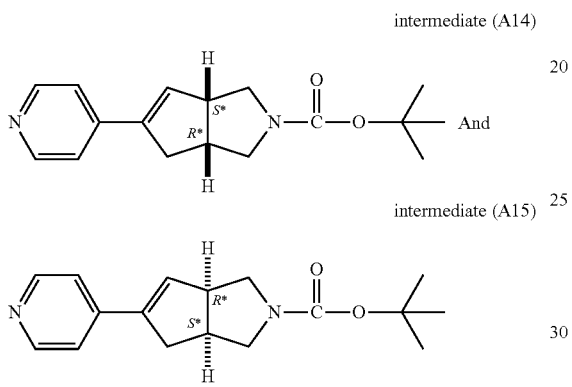

intermediate (A14)

And intermediate (A15)

Intermediate (A13) was purified and resolved by chromatography on Chiralpak AD (20 μm, 2000 g, 110 mm) with a flow rate of 750 ml/min. The mobile phase was methanol 100%. The pure fractions were collected and evaporated to dryness to give 18.7 g of intermediate (A15) (R*,S*) (([α]$_D^{20}$=+55.75° (589 μm, c 0.339 w/v %, DMF, 20° C.)) and 20.7 g of intermediate (A14) (S*,R*) (([α]$_D^{20}$=−68.38° (589 μm, c 0.253 w/v %, DMF, 20° C.)).

Intermediate (A14)

$^1$H NMR (500 MHz, DMSO-d$_6$) δ (ppm) 8.52 (d, J=6.0 Hz, 2H), 7.41 (d, J=6.0 Hz, 2H), 6.50 (s, 1H), 3.36-3.61 (m, 4H), 2.81-3.02 (m, 3H), 2.61-2.53 (m, 1H), 1.36 (s, 9H)

Intermediate (A15)

$^1$H NMR (500 MHz, DMSO-d$_6$) δ (ppm) 8.52 (d, J=6.0 Hz, 2H), 7.41 (d, J=6.0 Hz, 2H), 6.50 (s, 1H), 3.36-3.61 (m, 4H), 2.81-3.02 (m, 3H), 2.61-2.53 (m, 1H), 1.36 (s, 9H)

(c) Preparation of

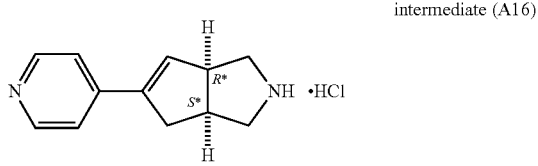 [SMILES: C1=C(c2ccncc2)C[C@@H]2CNC[C@H]12 ; Cl]

intermediate (A16)

Intermediate (A15) (24.8 g, 86.6 mmol) was added to HCl in dioxane (4 M, 108 ml) at 5° C. then the mixture was stirred at room temperature for 90 minutes. The precipitate was filtered off, washed with Et$_2$O and dried under vacuum at 70° C. 21.1 g of intermediate (A16).

(d) Preparation of

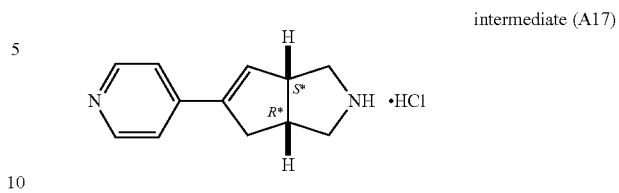

intermediate (A17)

Intermediate (A17) was prepared analogously starting from intermediate (A14).

Example A(iv)

Preparation of Intermediate A19

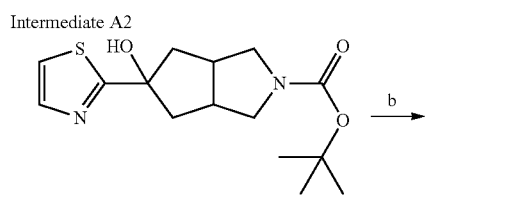

Intermediate A2

Intermediate A18

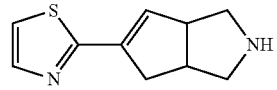

Intermediate A19 a) n-BuLi, Et$_2$O, thiazole, -78° C. to RT, 18 h; b) HCl, 140° C., 1 h, μw

Preparation of Compound 1 (Intermediate A18)

Under N$_2$ flow, n-BuLi (1.6M in hexanes) (40 mL, 63.92 mmol) was added dropwise at −78° C. to a solution of thiazole (4.16 mL, 58.59 mmol) in Et$_2$O (50 mL) then the mixture was stirred for 30 minutes. A solution of Intermediate (A2) (12 g, 56.27 mmol, described in the other patent) in Et$_2$O (50 mL) was added then the mixture stirred and allowed to reach room temperature for 18 hours. Water and EtOAc were added, the organic layer was separated, washed with water, brine, dried (MgSO$_4$) and evaporated till dryness. The residue (17 g) was purified by chromatography over silica gel (50 g, 15-40 μm, mobile phase gradient from Heptane/EtOAc from 80/20 to 50/50). The pure fractions were collected and evaporated to dryness to afford 10 g (61%) of Intermediate A18.

Preparation of Intermediate A19

A mixture of Intermediate A18 (1.05 g, 3.38 mmol) in an aqueous solution of 37% HCl in water (7 mL) in a sealed tube was heated at 140° C. using a single mode microwave (Biotage Initiator EXP 60) with a power output ranging from 0 to 400 W for 1 hour. The reaction mixture was poured into K$_2$CO$_3$ 10% aq, the organic layer was separated, dried (MgSO$_4$) and evaporated till dryness. Yielding: 0.23 g, (35%).

The aqueous layer was evaporated till dryness, the solid was suspended in CH$_2$Cl$_2$ and stirred for 10 minutes. The suspension was filtered and the filtrate was evaporated till dryness. Yielding: 0.29 g, (45%)

The two crops were gathered for purification, it was carried out by flash chromatography over silica gel (15-40 μm, 30 g, mobile phase gradient from 100% CH$_2$Cl$_2$ to 90% CH$_2$Cl$_2$, 10% CH$_3$OH, 1% NH$_4$OH). The pure fractions were collected and evaporated to dryness to afford 0.42 g (65%) of Intermediate A19.

Preparation of Intermediate A20

The following Intermediate A20:

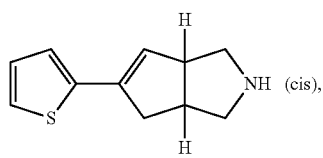 [SMILES: C1=C(c2cccs2)CC2CNCC12]

was prepared in accordance with the procedures described herein, for example in accordance with the procedures to prepare intermediate A9.

Example B

Preparation of Intermediate B

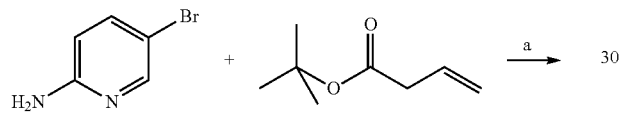

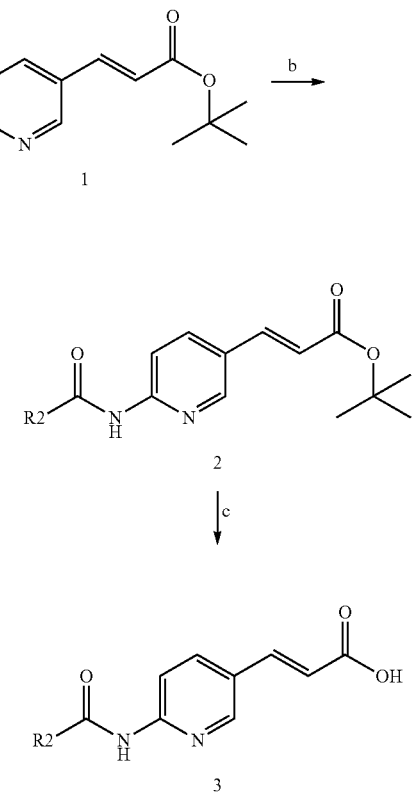

a) DIPEA, Pd(OAc)$_2$, tri-O-tolylphosphine, DMF, ACN, μW; b) HATU, DIPEA, DMF, 70° C.; c) TFA, HCl in dioxane, DCM, RT Preparation of Intermediate (B3)

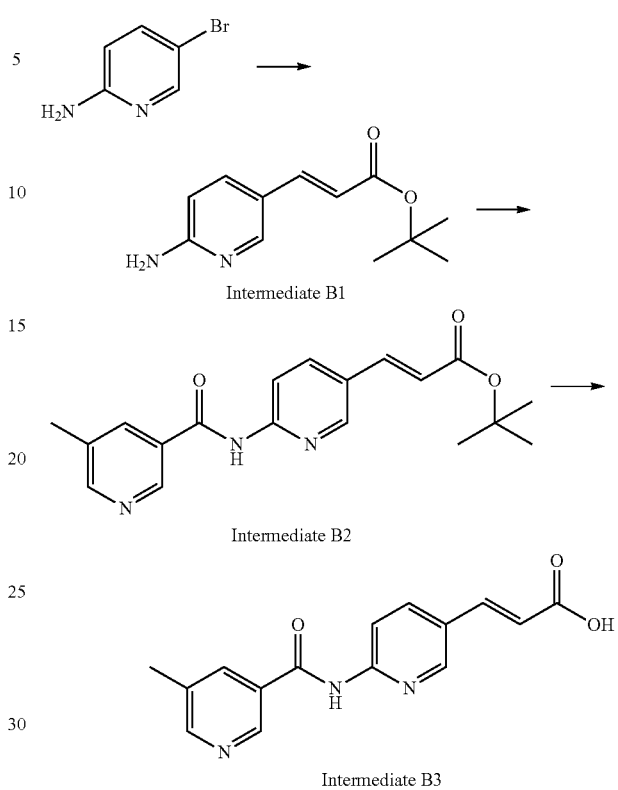

Preparation of Intermediate B1

A solution of 2-amino-5-bromopyridine (4 g, 23.12 mmol), tert-Butyl-acrylate (13.42 mL, 92.48 mmol) and N,N-diisopropylethylamine (7.64 mL, 46.24 mmol) in DMF (60 mL) and ACN (20 mL) was stirred and degassed with N$_2$ for 10 minutes. Palladium acetate (0.52 g, 2.32 mmol) and Tri-O-tolylphosphine (1.41 g, 4.63 mmol) were added and the solution was heated at 180° C. using one multimode cavity microwave CEM MARS system with a power output ranging (50%) from 0 to 800 W for 30 min. The reaction mixture was filtered through a short pad of Celite® and washed with EtOAc. The organic layer was washed with water, dried over MgSO$_4$, filtered and evaporated to dryness. The residue was purified by column chromatography over silica gel (SiOH 20-45 μm, 450 g, eluent: 0.1% NH$_4$OH, 97% DCM, 3% MeOH). Yielding: Intermediate B1 a pale yellow powder 3.55 g (70%)

Preparation of Intermediate B2

A solution of Intermediate B1 (0.8 g, 3.63 mmol), 5-methylnicotinic acid (0.9 g, 6.54 mmol), O-(7-Azabenzotriazol-1-yl)-N,N,N',N'-tetramethyluronium hexafluoro-phosphate CAS [148893-10-1] (2.49 g, 6.54 mmol) and N,N-diisopropylethylamine (1.4 mL, 7.99 mmol) in DMF dry (16 mL) was stirred overnight at 70° C. The mixture was poured out into water. The organic layer was extracted with CH$_2$Cl$_2$. The combined organic layers were washed with brine, dried over MgSO$_4$, filtered and concentrated. The residue was crystallized from EtOH to obtain a pale beige powder, Yielding: Intermediate B2 0.86 g (70%).

Preparation of Intermediate B3

Trifluoroacetic acid (4.9 mL, 63.35 mmol) was added to a solution of Intermediate B2 (0.86 g, 2.53 mmol) in CH$_2$Cl$_2$ (9 mL). The reaction mixture was stirred at room temperature for 4 hours, concentrated under reduce pressure and then triturated with Et₂O, filtered off and dried under vacuum. The residue was then triturated overnight in hydrogen chloride 4M in dioxane (8.2 mL, 32.94 mmol), the solid was filtered off, washed with Et₂O and dried under vacuum (70° C.). Yielding: Intermediate B3—white powder, 0.878 g, (99%).

Preparation of Intermediate B5

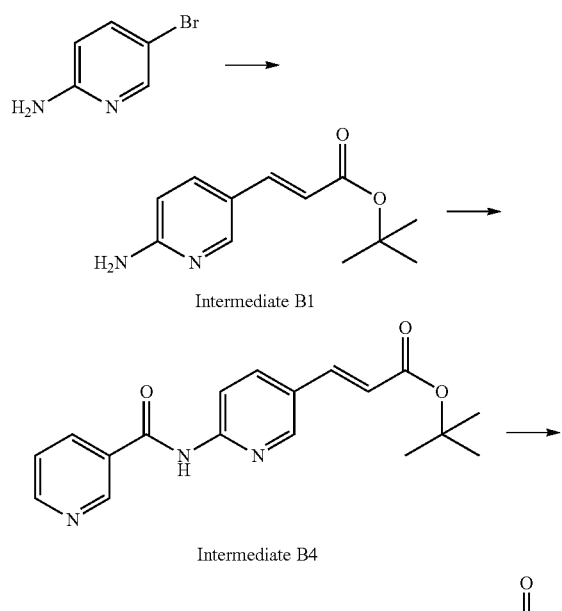

Preparation of Intermediate B4

Intermediate B4 was prepared in the same way as Intermediate B2, starting from Intermediate B1 and nicotinic acid CAS [59-67-6]. Yielding: 0.35 g, 29%.

Preparation of Intermediate B5

Intermediate B5 was prepared in the same way as Intermediate B3, starting from Intermediate B4. Yielding: 0.99 g, 99%.

Preparation of Intermediate B7

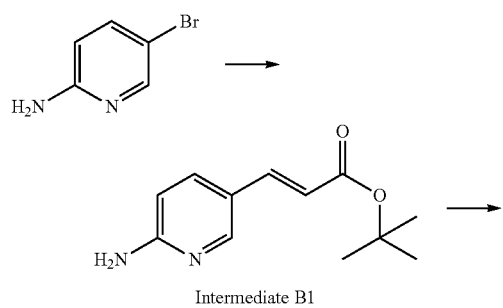

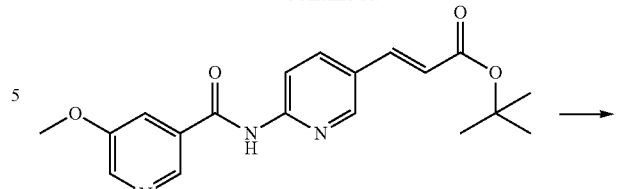

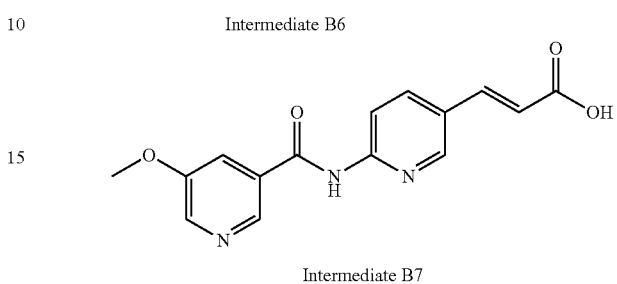

Preparation of Intermediate B6

Intermediate B6 was prepared in the same way as Intermediate B2, starting from Intermediate B1 and 5-methoxynicotinic acid CAS [1044919-31-4]. Yielding: 0.74 g, 92%.

Preparation of Intermediate B7

Intermediate B7 was prepared in accordance with the procedures to prepare Intermediate B3, starting from Intermediate B6. Yielding: 0.75 g, 97%.

Preparation of Intermediate B9

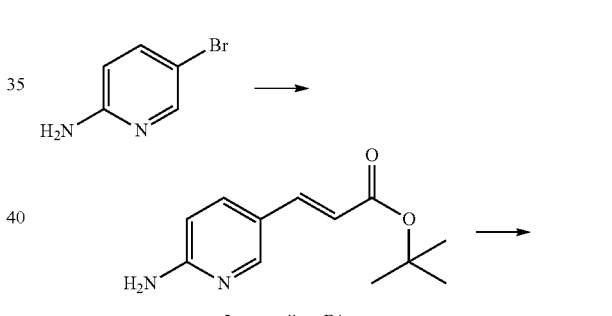

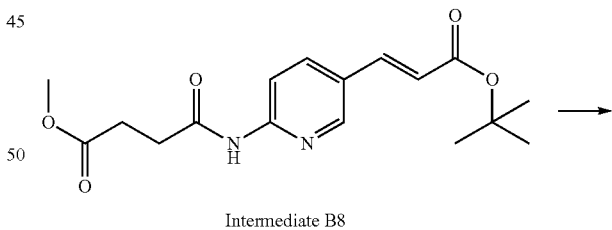

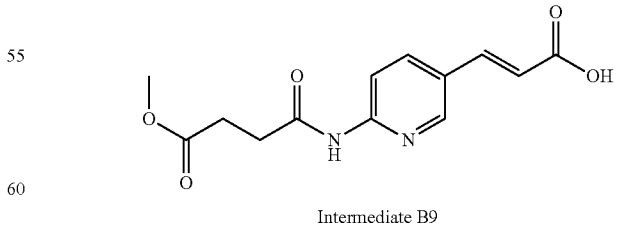

Preparation of Intermediate B8

Intermediate B8 was prepared in the same way as Intermediate B2, starting from Intermediate B1 and mono-methyl succinate CAS [3878-55-5]. Yielding: 0.76 g, 65%.

Preparation of Intermediate B9

Intermediate B9 was prepared in the same way as Intermediate B3, starting from Intermediate B8. Yielding: 0.40 g, 99%.

Preparation of Intermediate B11

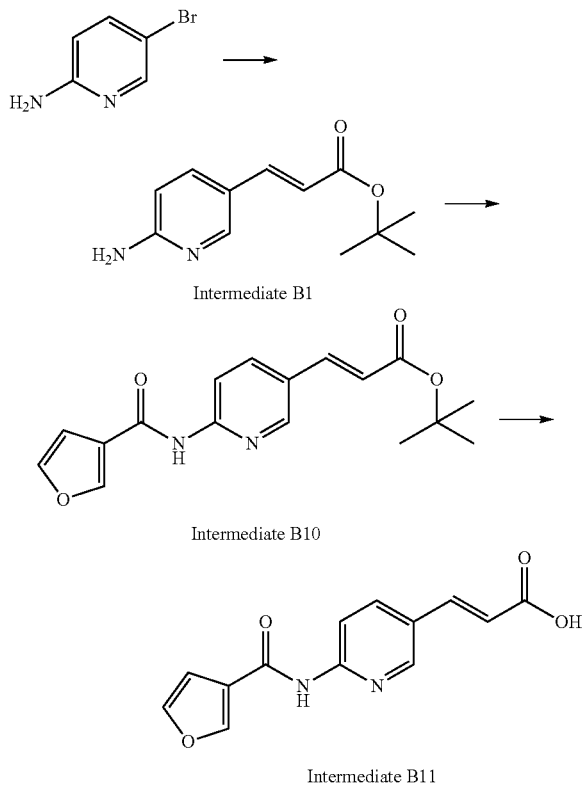

Preparation of Intermediate B10

Intermediate B10 was prepared in the same way as Intermediate B2, starting from Intermediate B1 and 3-furoic acid CAS [488-93-7]. Yielding: 0.35 g, 49%.

Preparation of Intermediate B11

Intermediate B11 was prepared in the same way as Intermediate B3, starting from Intermediate B10. Yielding: 0.38 g, 91%.

Example C

Final Compounds

Synthesis of Final Compounds (Compound C)

Preparation of Compound C1

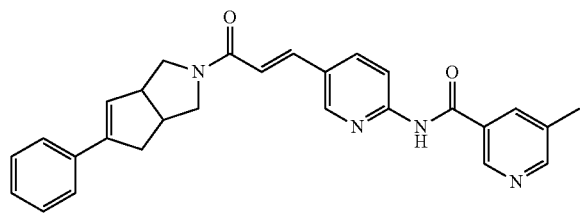 [SMILES: Cc1cncc(C(=O)Nc2ccc(/C=C/C(=O)N3CC4C=C(c5ccccc5)CC4C3)cn2)c1]

A solution of Intermediate A5 (0.09 g, 0.49 mmol), Intermediate B3 (0.17 g, 0.49 mmol), 1-hydroxybenzotriazole (0.079 g, 0.58 mmol), 1-(3-dimethylaminpropyl)-3-ethylcarbodiimide hydrochloride (0.11 g, 0.58 mmol) and triethylamine (0.24 mL, 1.7 mmol) in $CH_2Cl_2$ (4 mL) and THF (4 mL) was stirred overnight at room temperature. The mixture was poured out into water. The organic layer was extracted with $CH_2Cl_2$. The combined organic layers were washed with brine, dried over $MgSO_4$, filtered and concentrated. The residue was crystallized from EtOH, filtered off and dried under vacuum at 60° C. Yielding: Compound C1 as a beige powder 0.102 g, (47%). m.p. 214° C.

$^1$H NMR (500 MHz, DMSO-$d_6$) δ (ppm) 11.19 (s, 1H), 8.94 (d, J=3.15 Hz, 1H), 8.71-8.68 (m, 1H), 8.60 (br. s., 1H), 8.17-8.29 (m, 3H), 7.51-7.45 (m, 3H), 7.34 (t, J=7.57 Hz, 2H), 7.23-7.29 (m, 1H), 7.05-7.14 (m, 1H), 6.21 (br. s., 1H), 3.35-4.07 (m, 5H), 2.89-3.28 (m, 2H), 2.61-2.67 (m, 1H), 2.36-2.40 (m, 3H).

Preparation of Compound C2

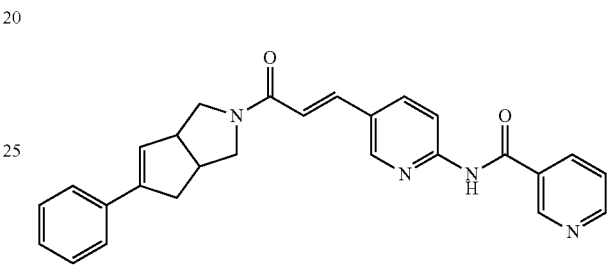

Compound C2 was prepared in the same way as Compound C1, starting from Intermediate A5 and Intermediate B5. Yielding: Compound C2 as a white powder 0.060 g, (35%). m.p. 238° C.

$^1$H NMR (500 MHz, DMSO-$d_6$) δ (ppm) 11.27 (br. s., 1H), 9.13 (d, J=3.15 Hz, 1H), 8.72-8.68 (m, 1H), 8.68 (d, J=9.77 Hz, 1H), 8.32-8.38 (m, 1H), 8.19-8.30 (m, 2H), 7.55 (dt, J=4.18, 8.04 Hz, 1H), 7.44-7.51 (m, 3H), 7.34 (t, J=7.57 Hz, 2H), 7.22-7.29 (m, 1H), 7.05-7.15 (m, 1H), 6.21 (br. s., 1H), 3.41-4.08 (m, 5H), 2.88-3.23 (m, 2H), 2.67-2.61 (m, 1H).

Preparation of Compound C3

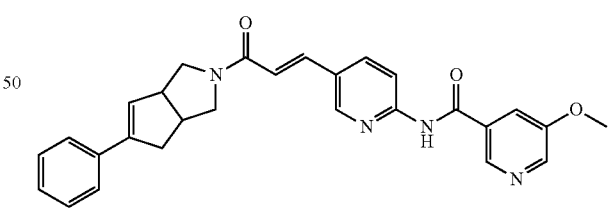

Compound C3 was prepared in the same way as Compound C1, starting from Intermediate A5 and Intermediate B7. Yielding: Compound C3 as a white powder 0.083 g, (49%). m.p. 205° C.

$^1$H NMR (500 MHz, DMSO-$d_6$) δ (ppm) 11.26 (s, 1H), 8.72-8.76 (m, 1H), 8.66-8.71 (m, 1H), 8.70-8.66 (m, 1H), 8.20-8.30 (m, 2H), 7.96 (m, 1H), 7.44-7.51 (m, 3H), 7.34 (t, J=7.57 Hz, 2H), 7.23-7.29 (m, 1H), 7.06-7.14 (m, 1H), 6.20 (br.s., 1H), 3.89-4.07 (m, 4H), 3.41-3.86 (m, 3H), 2.88-3.22 (m, 3H), 2.61-2.67 (m, 1H).

Preparation of Compound C4

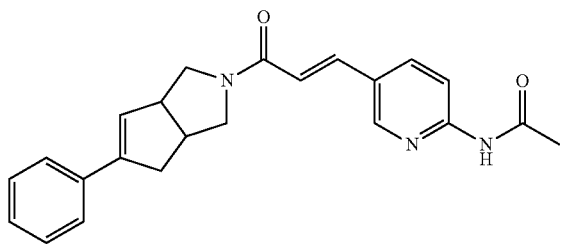 [SMILES: CC(=O)Nc1ccc(/C=C/C(=O)N2CC3C=C(c4ccccc4)CC3C2)cn1]

Compound C4 was prepared in the same way as Compound C1, starting from Intermediate A5 and (2E)-3-[6-(acetylamino)-3-pyridinyl]-2-propenoic acid CAS [160648-18-0]. Yielding: Compound C4 as a white powder 0.076 g, (38%). m.p. 251° C.

$^1$H NMR (500 MHz, DMSO-d$_6$) δ (ppm) 10.68-10.58 (m, 1H), 8.61-8.56 (m, 1H), 8.04-8.20 (m, 2H), 7.48 (d, J=7.57 Hz, 2H), 7.45-7.38 (m, 1H), 7.34 (t, J=7.57 Hz, 2H), 7.23-7.29 (m, 1H), 6.98-7.08 (m, 1H), 6.20 (br. s., 1H), 3.38-4.07 (m, 5H), 2.87-3.25 (m, 2H), 2.63-2.60 (m, 1H), 2.12-2.09 (m, 3H).

Preparation of Compound C5

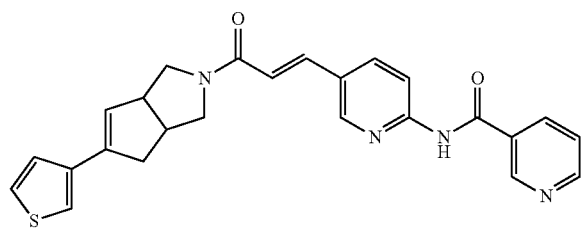 [SMILES: O=C(Nc1ccc(/C=C/C(=O)N2CC3C=C(c4ccsc4)CC3C2)cn1)c1cccnc1]

Compound C5 was prepared in the same way as Compound C1, starting from Intermediate A9 and Intermediate B5. Yielding: Compound C5 as a white powder 0.107 g, (54%). m.p. 236° C.

$^1$H NMR (500 MHz, DMSO-d$_6$) δ (ppm) 11.27 (br. s., 1H), 9.12-9.15 (m, 1H), 8.76 (dt, J=2.13, 4.57 Hz, 1H), 8.66-8.70 (m, 1H), 8.33-8.37 (m, 1H), 8.20-8.29 (m, 2H), 7.51-7.57 (m, 2H), 7.47 (m, 1H), 7.42 (d, J=2.21 Hz, 1H), 7.34-7.37 (m, 1H), 7.12-7.05 (m, 1H), 6.02 (br. s., 1H), 3.40-4.05 (m, 5H), 2.85-3.21 (m, 3H).

Preparation of Compound C6

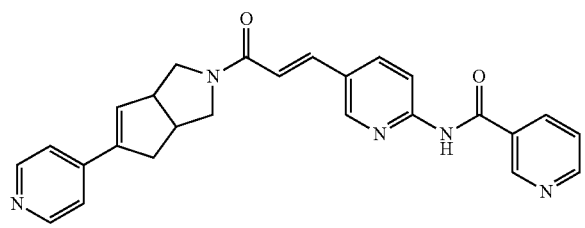 [SMILES: O=C(Nc1ccc(/C=C/C(=O)N2CC3C=C(c4ccncc4)CC3C2)cn1)c1cccnc1]

Compound C6 was prepared in the same way as Compound C1, starting from Intermediate A13 and Intermediate B5. Yielding: Compound C6 as a white powder 0.048 g, (19%). m.p. 196° C.

$^1$H NMR (500 MHz, DMSO-d$_6$) δ (ppm) 11.30-11.26 (m, 1H), 9.13 (br. s., 1H), 8.76 (br. s., 1H), 8.68 (d, J=9.46 Hz, 1H), 8.52 (d, J=5.04 Hz, 2H), 8.35 (br. s., 1H), 8.20-8.30 (m, 2H), 7.52-7.58 (m, 1H), 7.41-7.50 (m, 3H), 7.12-7.03 (m, 1H), 6.54 (d, J=7.25 Hz, 1H), 3.40-4.09 (m, 4H), 2.87-3.24 (m, 3H), 2.69-2.62 (m, 1H).

Preparation of Compound C7

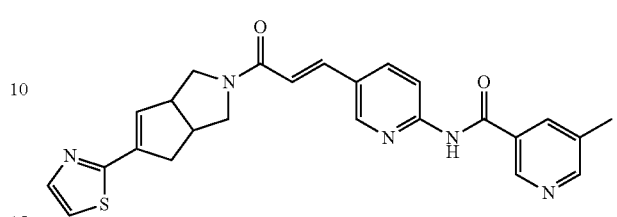

Compound C7 was prepared in the same way as Compound C1, starting from Intermediate A19 and Intermediate B3. Yielding: Compound C7 as a white powder 0.107 g, (54%). m.p. 231° C.

$^1$H NMR (500 MHz, DMSO-d$_6$) δ (ppm) 11.21-11.18 (m, 1H), 8.94 (br. s., 1H), 8.68 (d, J=6.31 Hz, 1H), 8.60 (s, 1H), 8.16-8.28 (m, 3H), 7.79-7.84 (m, 1H), 7.67-7.71 (m, 1H), 7.45-7.42 (m, 1H), 7.15-7.08 (m, 1H), 6.44 (s, 1H), 3.44-4.08 (m, 5H), 2.60-3.27 (m, 3H), 2.34-2.41 (m, 3H).

Preparation of Compound C8

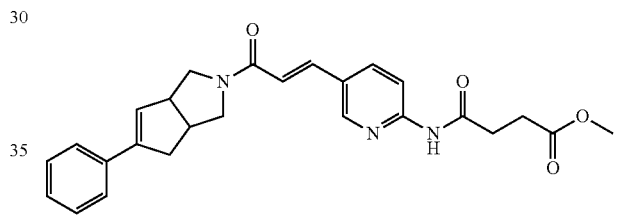

Compound C8 was prepared in the same way as Compound C1, starting from Intermediate A5 and Intermediate B9. Yielding: Compound C8 as a pale yellow powder 0.151 g, (51%). m.p. 216° C.

$^1$H NMR (500 MHz, DMSO-d$_6$) δ (ppm) 10.71-10.76 (m, 1H), 8.54-8.60 (m, 1H), 8.10-8.19 (m, 1H), 8.03-8.10 (m, 1H), 7.48 (d, J=7.57 Hz, 2H), 7.38-7.45 (m, 1H), 7.34 (t, J=7.57 Hz, 2H), 7.22-7.28 (m, 1H), 6.99-7.08 (m, 1H), 6.18-6.22 (m, 1H), 3.39-4.05 (m, 8H), 2.87-3.21 (m, 3H), 2.55-2.74 (m, 4H).

The remaining compounds of the table in which there are compounds in which ring is (i) were prepared in accordance with the procedures described herein, using commercially available starting materials where applicable.

Preparation of Final Compounds in which the Ring R$^x$ is Ring (ii):

Synthesis of Final Compounds F

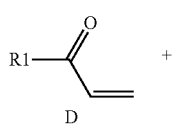

Preparation of Intermediate D
Preparation of Intermediate D1

A solution of acryloyl chloride (0.88 mL, 10.82 mmol) in CH$_2$Cl$_2$ (5 mL) was added dropwise at 5° C. to a solution of Intermediate A5 (2.0 g, 9.02 mmol) and triethylamine (1.5 mL, 10.82 mmol) in CH$_2$Cl$_2$ (15 mL) then the mixture was stirred for 4 hours at room temperature. Water and CH$_2$Cl$_2$ were added, the organic layer was separated, washed with water, dried (MgSO$_4$) and evaporated till dryness. The residue was purified by flash chromatography over silica gel (15-40 µm, 40 g, mobile phase gradient: 100% CH$_2$Cl$_2$ to 98% CH$_2$Cl$_2$, 2%/MeOH). The pure fractions were collected and evaporated to dryness to give 1.12 g (52%) of Intermediate D1 as a white solid.

Preparation of Intermediate D2

Intermediate D2 was prepared in the same way as Intermediate D1, starting from Intermediate A7. Yielding: 1.4 g, quantitative.

Preparation of Intermediate D3

Intermediate D3 was prepared in the same way as Intermediate D1, starting from Intermediate A9. Yielding: 0.72 g, 98%.

Preparation of Intermediate D4

Intermediate D4 was prepared in the same way as Intermediate D1, starting from Intermediate A13. Yielding: 0.28 g, 78%.

Preparation of Intermediate D5

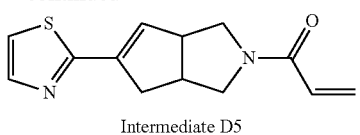

Intermediate D5

Intermediate D5 was prepared in the same way as Intermediate D1, starting from Intermediate A19. Yielding: 0.32 g, 88%.

Preparation of Intermediate D7

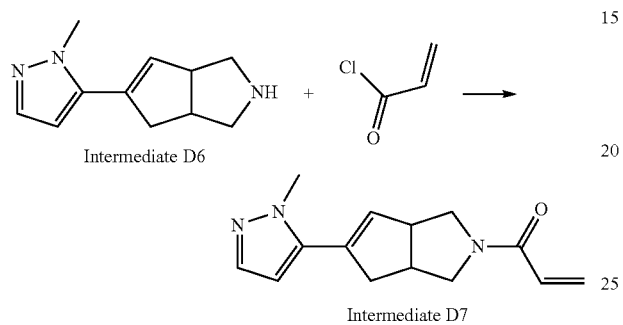

Intermediate D7

Intermediate D7 was prepared in the same way as Intermediate D1, starting from Intermediate D6 (in which D6 is prepared in accordance with the procedures described hereinbefore for the preparation of Intermediate A4). Yielding: 0.3 g, 88%.

Preparation of Intermediate E

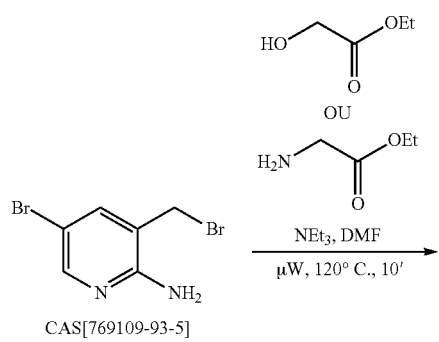

X: O, NH

Preparation of Intermediate E2

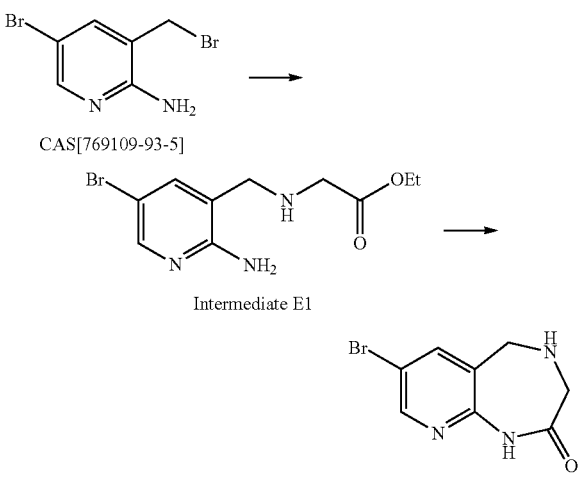

Intermediate E2

Preparation of Intermediate E1

A mixture of glycine methyl ester hydrochloride (4.93 g, 39.3 mmol), 2-amino-5-bromo-3-bromoethylpyridine (10 g, 19.7 mmol) and triethylamine (13.7 mL, 98.3 mmol) in DMF (100 mL), in a sealed tube, was heated at 120° C. using one single mode microwave (Biotage Initiator EXP 60) with a power output ranging from 0 to 400 W for 10 min. CH$_2$Cl$_2$ and the minimum of water were added, the organic layer was separated, dried (MgSO$_4$) and evaporated till dryness The residue (6 g) was purified by flash chromatography over silica gel (120 g, 15-40 µm, mobile phase 100% CH$_2$Cl$_2$). The pure fractions were collected and concentrated to afford 3 g of Intermediate E1.

Preparation of Intermediate E2

Under N$_2$ flow, NaH (0.8 g, 20.1 mmol) was added portionwise to a solution of Intermediate E1 (4.6 g, 16.8 mmol) in DMF (50 mL) at 5° C. then the mixture was stirred for 2 hours at room temperature. EtOAc and the minimum of water were added, the organic layer was separated, the aqueous layer was saturated with NaCl and extracted with EtOAc. The combined organic layers were dried (MgSO$_4$) and evaporated until dryness. The residue was crystallized from EtOH, the precipitate was filtered off and dried under vacuum to give 1.5 g (37%) of Intermediate E2.

Preparation of Intermediate E4

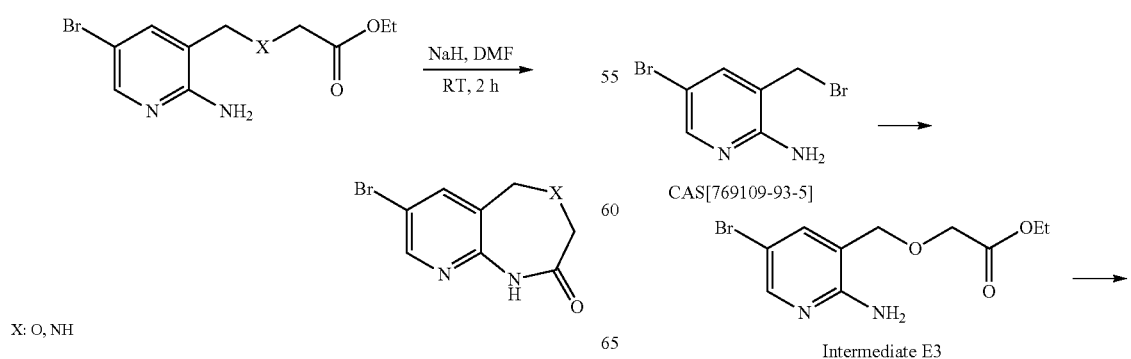

Intermediate E3

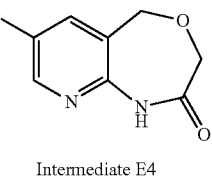

Intermediate E4

Preparation of Intermediate E3

Intermediate E3 was prepared in the same way as Intermediate E1, starting from 2-amino-5-bromo-3-bromoethylpyridine and ethyl glycolate. Yielding: 1.2 g, 22%.

Preparation of Intermediate E4

Intermediate E4 was prepared in the same way as Intermediate E2, starting from Compound 4. Yielding: 1.2 g, 27%.

Synthesis of Final Compound F

Preparation of Compound F1

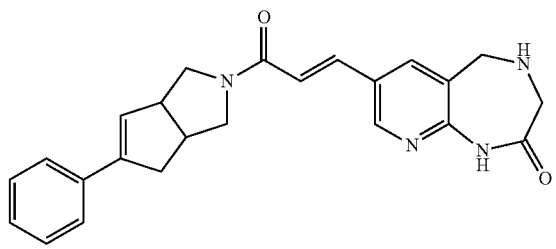 [SMILES: O=C1CNCc2cc(/C=C/C(=O)N3CC4C=C(c5ccccc5)CC4C3)cnc2N1]

A solution of Intermediate D1 (0.59 g, 2.48 mmol), Intermediate E2 (0.4 g, 1.65 mmol) and N,N-diisopropylamine (0.55 mL, 3.3 mmol) in ACN (10 mL) and DMF (2 ml) was stirred and degassed with $N_2$ for 10 minutes. Palladium acetate (37.1 mg, 165.2 µmol) and Tri-O-tolylphosphine (0.1 g, 0.33 mmol) were added in a sealed tube. The solution was heated at 180° C. using one single mode microwave (Biotage Initiator EXP 60) with a power output ranging from 0 to 400 W for 30 min. The reaction mixture was evaporated till dryness, taken up in a mixture of $CH_2Cl_2$/MeOH 9/1, filtered through a short pad of Celite® and washed with $CH_2Cl_2$. The organic layer was washed with water, dried over $MgSO_4$, filtered and evaporated. The residue was purified by flash chromatography over silica gel (80 g, 15-40 µm, mobile phase 95% $CH_2Cl_2$, 5% MeOH, 0.5% $NH_4OH$). The pure fractions were collected and concentrated. The crude product was crystallized from EtOH, the precipitate was filtered off and dried to give 0.1 g (16%) of Compound F1. m.p.>260° C.

$^1$H NMR (500 MHz, DMSO-$d_6$) δ 10.04-10.08 (m, 1H), 8.38-8.43 (m, 1H), 7.95-8.01 (m, 1H), 7.48 (d, J=7.57 Hz, 2H), 7.37-7.44 (m, 1H), 7.34 (t, J=7.57 Hz, 2H), 7.23-7.29 (m, 1H), 6.98-7.06 (m, 1H), 6.18-6.23 (m, 1H), 3.38-4.04 (m, 8H), 2.88-3.22 (m, 4H), 2.60-2.67 (m, 1H).

Preparation of Compound F2

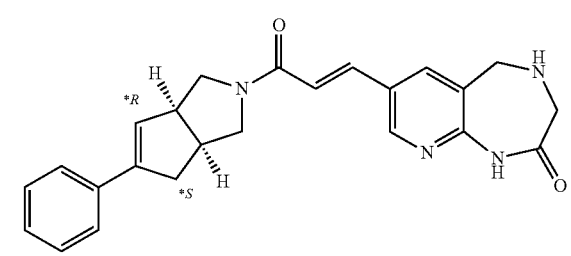 [SMILES: O=C1CNCc2cc(/C=C/C(=O)N3C[C@H]4CC(c5ccccc5)=C[C@H]4C3)cnc2N1]

The compound F2 was prepared in the same way as compound F1, starting from Intermediate D2 and Intermediate E2. Yielding: Compound F2 as a white powder 0.104 g, (21%). m.p.>260° C.

$^1$H NMR (500 MHz, DMSO-$d_6$) δ 10.05-10.09 (m, 1H), 8.38-8.44 (m, 1H), 7.94-8.02 (m, 1H), 7.48 (d, J=7.57 Hz, 2H), 7.37-7.45 (m, 1H), 7.34 (t, J=7.57 Hz, 2H), 7.23-7.29 (m, 1H), 6.97-7.07 (m, 1H), 6.22-6.18 (m, 1H), 3.38-4.05 (m, 8H), 2.87-3.23 (m, 4H), 2.59-2.67 (m, 1H).

Preparation of Compound F3

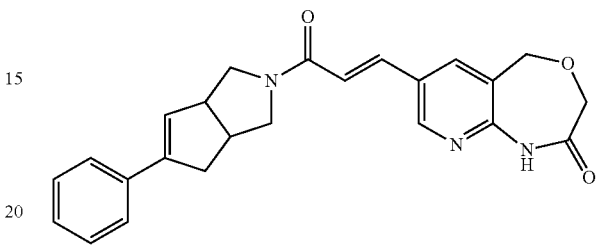

Compound F3 was prepared in the same way as Compound F1, starting from Intermediate D1 and Intermediate E4. Yielding: Compound F3 as a white powder 0.084 g, (50%). m.p. 266.6° C.

$^1$H NMR (500 MHz, DMSO-$d_6$) δ 10.55-10.60 (m, 1H), 8.45-8.51 (m, 1H), 7.99-8.08 (m, 1H), 7.48 (d, J=7.57 Hz, 2H), 7.38-7.45 (m, 1H), 7.34 (t, J=7.41 Hz, 2H), 7.23-7.29 (m, 1H), 6.98-7.08 (m, 1H), 6.22-6.18 (m, 1H), 4.75 (d, J=12.3 Hz, 2H), 4.53-4.49 (m, 2H), 3.37-4.05 (m, 5H), 2.88-3.22 (m, 2H), 2.64-2.60 (m, 1H).

Preparation of Compound F4

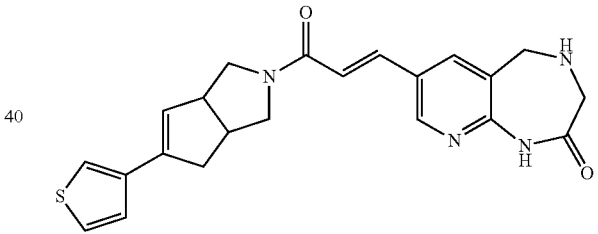

Compound F4 was prepared in the same way as Compound F1, starting from Intermediate E2 and Intermediate D3. Yielding: Compound F4 as a white powder 0.028 g, (7%). m.p. 240° C.

$^1$H NMR (500 MHz, DMSO-$d_6$) δ 10.05-10.08 (m, 1H), 8.38-8.44 (m, 1H), 7.94-8.02 (m, 1H), 7.50-7.54 (m, 1H), 7.33-7.45 (m, 3H), 6.97-7.07 (m, 1H), 6.04-6.01 (m, 1H), 3.36-4.03 (m, 8H), 2.83-3.20 (m, 4H), 2.56-2.64 (m, 1H).

Preparation of Compound F5

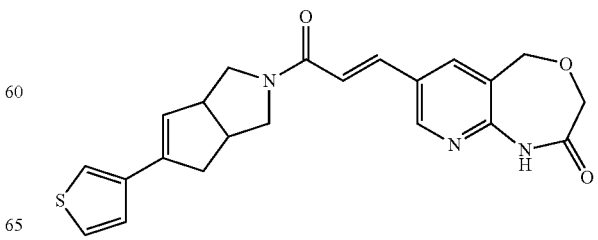

Compound F5 was prepared in the same way as Compound F1, starting from Intermediate E4 and Intermediate D3. Yielding: Compound F5—0.056 g, (14%). m.p. 152° C.

¹H NMR (400 MHz, DMSO-d₆) δ 10.52 (br. s., 1H), 8.43-8.52 (m, 1H), 7.98-8.07 (m, 1H), 7.31-7.55 (m, 4H), 6.95-7.08 (m, 1H), 6.01 (br. s., 1H), 4.76-4.80 (m, 2H), 4.52-4.50 (m, 2H), 3.35-4.04 (m, 4H), 2.83-3.22 (m, 3H), 2.54-2.70 (m, 1H).

Preparation of Compound F6

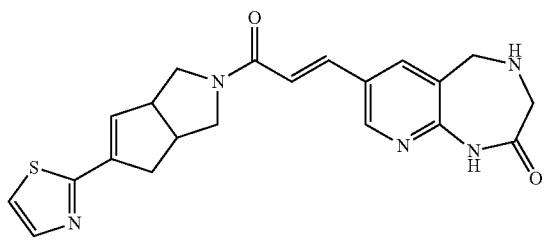 [SMILES: O=C1CNCc2cc(/C=C/C(=O)N3CC4C=C(c5nccs5)CC4C3)cnc2N1]

Compound F6 was prepared in the same way as Compound F1, starting from Intermediate E2 and Intermediate D5. Yielding: Compound F6—0.123 g, (24%). m.p. 240° C.

¹H NMR (500 MHz, DMSO-d₆) δ 10.04-10.09 (m, 1H), 8.38-8.43 (m, 1H), 7.95-8.01 (m, 1H), 7.79-7.83 (m, 1H), 7.67-7.71 (m, 1H), 7.38-7.44 (m, 3H), 6.98-7.05 (m, 1H), 6.43 (br. s., 1H), 3.42-4.03 (m, 9H), 2.97-3.24 (m, 3H), 2.68-2.78 (m, 1H).

Preparation of Compound F7

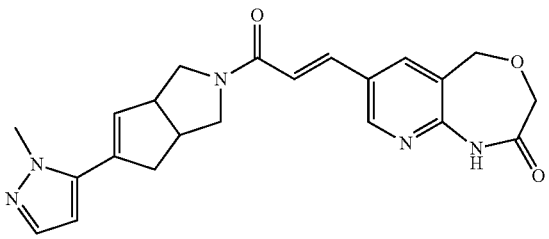 [SMILES: Cn1nccc1C1=CC2CN(C(=O)/C=C/c3cnc4c(c3)COCC(=O)N4)CC2C1]

Compound F7 was prepared in the same way as Compound F1, starting from Intermediate E4 and Intermediate D7. Yielding: Compound F7—0.136 g, (41%). m.p. 149° C.

¹H NMR (500 MHz, DMSO-d₆) δ 10.58 (s, 1H), 8.46-8.51 (m, 1H), 8.01-8.07 (m, 1H), 7.39-7.46 (m, 1H), 7.35 (d, J=2.52 Hz, 1H), 6.98-7.08 (m, 1H), 6.29 (m, 1H), 6.08-6.04 (m, 1H), 4.80-4.76 (m, 2H), 4.55-4.52 (m, 2H), 3.38-4.04 (m, 7H), 2.91-3.24 (m, 3H), 2.54-2.63 (m, 1H).

Preparation of Compound F8

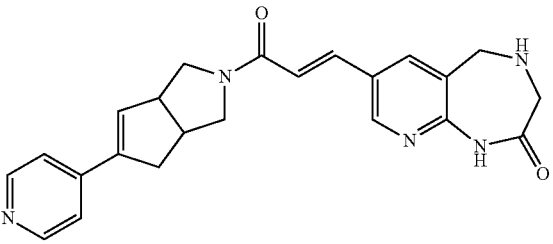 [SMILES: O=C1CNCc2cc(/C=C/C(=O)N3CC4C=C(c5ccncc5)CC4C3)cnc2N1]

Compound F8 was prepared in the same way as Compound F1, starting from Intermediate E2 and Intermediate D4. Yielding: Compound F8—0.104 g, (31%). m.p.>260° C.

¹H NMR (500 MHz, DMSO-d₆) δ 10.05-10.09 (m, 1H), 8.50-8.54 (d, J=5.99 Hz, 2H), 8.38-8.43 (m, 1H), 7.93-8.01 (m, 1H), 7.37-7.46 (m, 3H), 6.96-7.07 (m, 1H), 6.55-6.51 (m, 1H), 3.38-4.05 (m, 9H), 2.89-3.22 (m, 3H), 2.63 (m, 1H).

Preparation of Compound F9

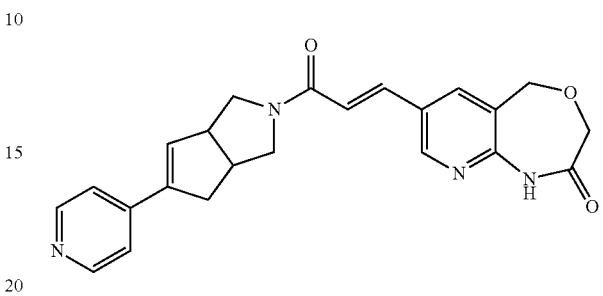

Compound F9 was prepared in the same way as Compound F1, starting from Intermediate E4 and Intermediate D4. Yielding: Compound F9—0.144 g (44%). m.p. 154° C.

¹H NMR (500 MHz, DMSO-d₆) δ 10.55-10.61 (m, 1H), 8.45-8.55 (m, 3H), 8.00-8.08 (m, 1H), 7.38-7.47 (m, 3H), 6.97-7.06 (m, 1H), 6.50-6.57 (m, 1H), 4.80-4.76 (m, 2H), 4.53-4.50 (m, 2H), 3.38-4.05 (m, 4H), 2.87-3.21 (m, 3H), 2.59-2.69 (m, 1H).

Example G

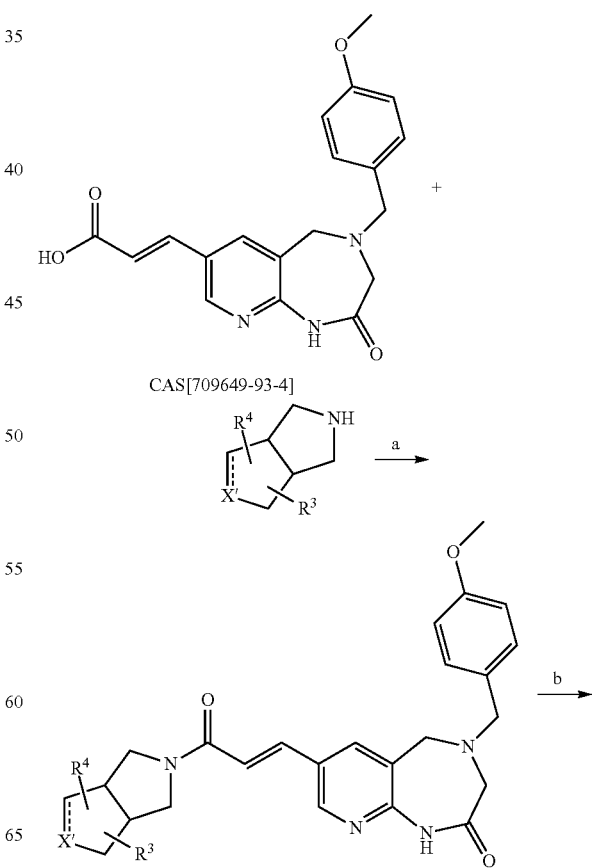

-continued

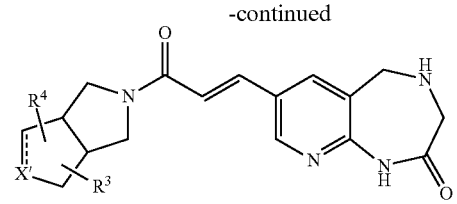

R1: 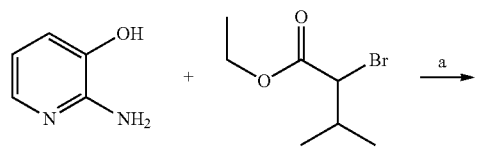

a) HOBT, EDCI, NEt₃, DCM, THF, RT, 18 h; b) chloroethyl chloroformate, DCE, MeOH, 50° C., 1 h; c) NaH, DMF, RT, 3 h.

Intermediate Examples H and Final Examples I

Preparation of Compound I1

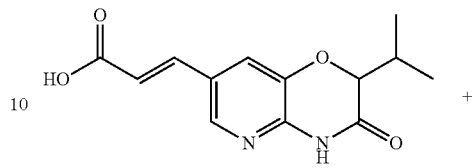

Intermediate H4

Intermediate A13

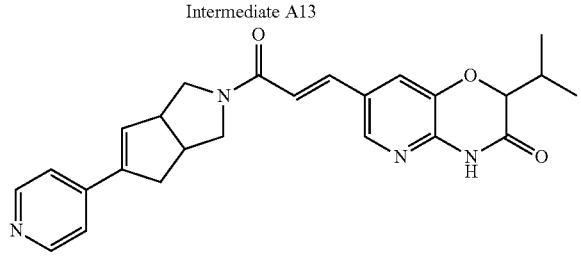

Compound I1

Preparation of Intermediate H4

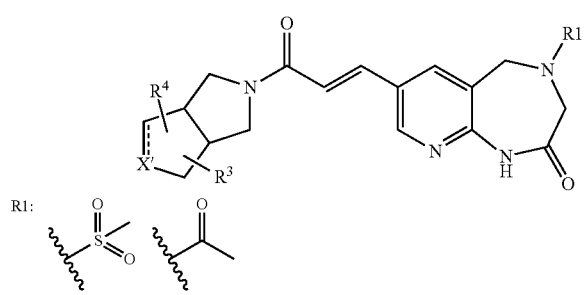

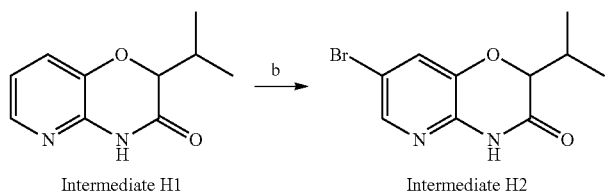

Intermediate H1 → Intermediate H2

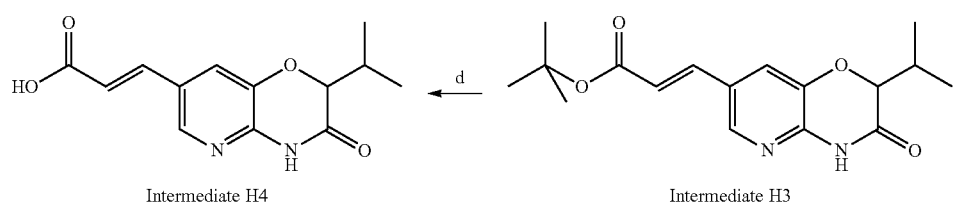

Intermediate H4 ← Intermediate H3 a) NaH, DMF, 80° C.; b) Br₂, DMF, RT; c) DIPEA, Pd(OAc)₂, tri-O-tolylphosphine, DMF, ACN μW; d) TFA, HCl in dioxane, DCM, RT Preparation of Intermediate H1

To a suspension of NaH (0.77 g, 19.23 mmol) in DMF (15 mL) was added dropwise a solution of 2-amino-3-hydroxy-pyridine (3 g, 27.24 mmol) in DMF (15 mL) at room temperature over a period of 10 minutes and the mixture was stirred at room temperature for 20 minutes. To the mixture was added dropwise ethyl-2-bromo-isovalerate CAS [609-12-1] (2.63 mL, 16.03 mmol) over a period of 20 minutes, the reaction mixture was stirred at room temperature for 1 hour and at 80° C. for 2 hours. After cooling, cold water was added, and the mixture was extracted with EtOAc. The organic layer was successively washed with water and brine, dried over $MgSO_4$ and concentrated under reduced pressure. The residue was purified by flash chromatography over silica gel (80 g, mobile phase gradient Heptane/EtOAc from 85/15 to 70/30). Pure fractions were collected and the solvent was removed. Yielding: Intermediate H1 as a white powder, 1.14 g, (37%).

Preparation of Intermediate H2

To a solution of Intermediate H1 (1.14 g, 3.26 mmol) in DMF (24 mL) was added dropwise bromine (0.23 mL, 4.57 mmol). The reaction mixture was stirred overnight at room temperature. The reaction mixture was poured out into water under vigorous stirring. EtOAc was added, the organic layer was separated, dried over $MgSO_4$, filtered off and evaporated. The residue was crystallized from EtOH and dried. Yielding: Intermediate H2, 0.66 g, (75%).

Preparation of Intermediate H3

Intermediate H3 was prepared in accordance with the procedures to prepare Intermediate B1 (described hereinbefore), starting from Intermediate H2 and tert-Butyl-acrylate. Yielding: a white powder 0.31 g (40%).

Preparation of Intermediate H4

Intermediate H4 was prepared in accordance with the procedures to prepare Intermediate B3 (as hereinbefore described), starting from Intermediate H3. Yielding: a white powder 0.29 g (89%).

Preparation of Compound I1

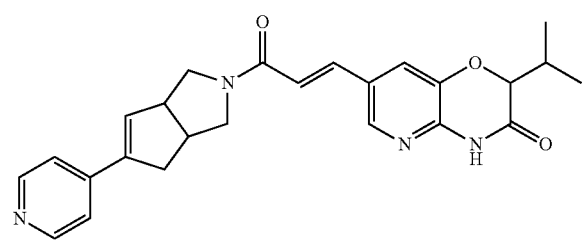 [SMILES: CC(C)C1Oc2cc(/C=C/C(=O)N3CC4C=C(c5ccncc5)CC4C3)cnc2NC1=O]

A mixture of Intermediate A13 (as hereinbefore described) (0.1 g, 4.0 mmol), Intermediate H4 (0.11 g, 4.0 mmol), N'(ethylcarbonimidoyl)-N,N-dimethyl-1,3-propanediamine (0.093 g, 0.48 mmol), 1-hydroxybenzotriazole (0.065 g, 0.48 mmol) and triethylamine (0.23 mL, 1.61 mmol) in $CH_2Cl_2$ (4 mL) and THF (4 mL) was stirred for 18 hours at room temperature. Water and $CH_2Cl_2$ were added, the organic layer was separated, washed with water, dried ($MgSO_4$) and evaporated until dryness. The residue was taken up in EtOH, filtered off and dried (vacuum, 60° C.) to give 0.113 g (65%) of 53487174-AAA. m.p. 113° C.

$^1$H NMR (500 MHz, DMSO-$d_6$) δ 11.43 (br. s., 1H), 8.52 (d, J=5.99 Hz, 2H), 8.09-8.12 (m, 1H), 7.84-7.92 (m, 1H), 7.43 (d, J=5.99 Hz, 2H), 7.35-7.41 (m, 1H), 7.00-7.09 (m, 1H), 6.50-6.56 (m, 1H), 4.49-4.57 (m, 1H), 3.40-4.05 (m, 4H), 2.88-3.23 (m, 2H), 2.59-2.67 (m, 1H), 2.18-2.28 (m, 2H), 1.02-1.08 (m, 3H), 0.89-0.98 (m, 3H).

The remaining compounds of Table (ii) in which the ring is ring (ii) were prepared in accordance with the procedures described herein.

Intermediate Examples J and Final Examples K

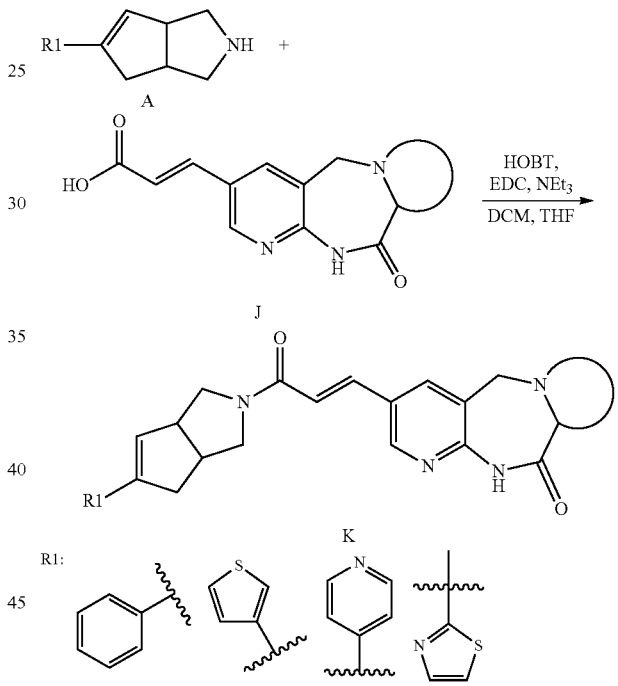

Preparation of Intermediate A

Intermediates A5, A9, A13 and A19 were Prepared as Hereinbefore Described.

Preparation of Intermediate J

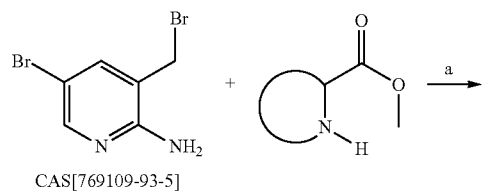

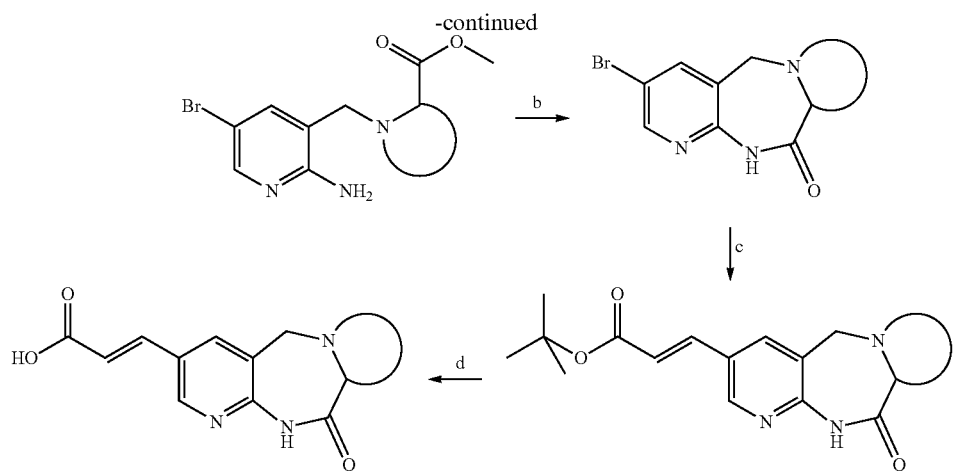

a) Et3N, DMF, μW; b) NaH, DMF, RT; c) DIPEA, Pd(OAc)2, tri-O-tolylphosphine, DMF, ACN, μW; d) TFA, HCl, DCM, RT Preparation of Intermediate J4

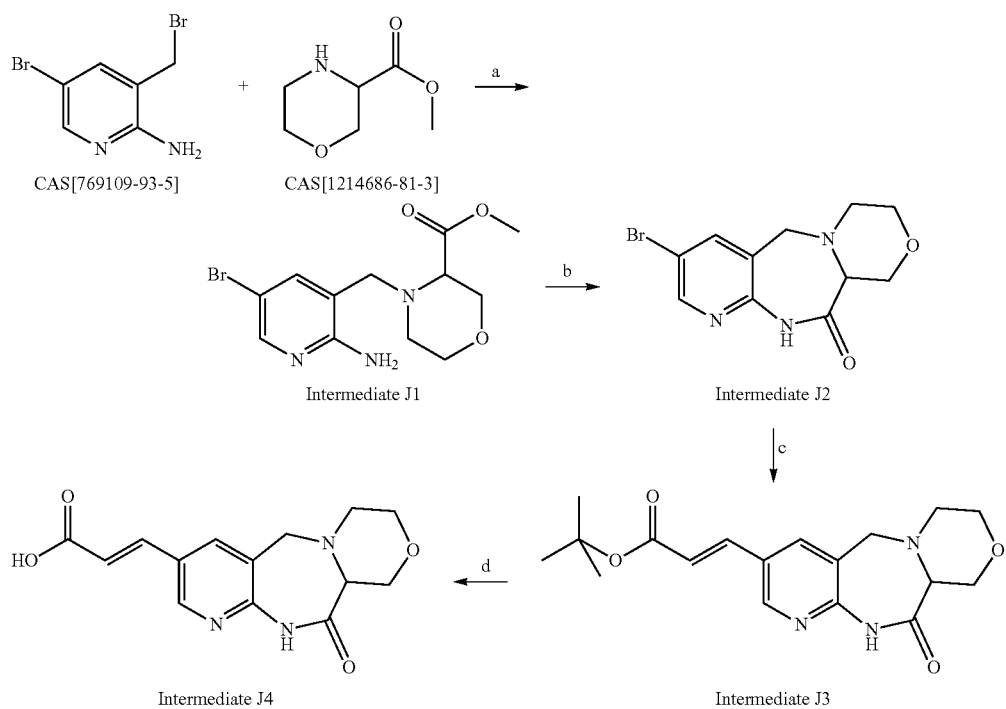

Preparation of Intermediate J1

A solution of 2-Amino-5-bromo-3-(bromomethyl)pyridine (15.2 g, 30.3 mmol), 3-morpholinecarboxylic acid methyl ester hydrochloride (5.5 g, 30.3 mmol) and triethylamine (21 mL, 151 mmol) in DMF (150 mL) and the solution was heated at 120° C. using one multimode cavity microwave CEM MARS system with a power output ranging (50%) from 0 to 400 W for 10 min in open vessel. Water and EtOAc were added, the organic layer was washed with water, brine, dried over MgSO$_4$, filtered and evaporated to dryness, Yielding: Intermediate J1—11.2 g (quantitative).

Preparation of Intermediate J2

NaH was added portionwise to a solution of Intermediate J1 (13.3 g, 40.3 mmol) in DMF (100 mL) at room temperature then the mixture was stirred for 5 hours. Water and EtOAc were added, the precipitate was filtered off. The organic layer was separated, washed with water then brine, dried (MgSO$_4$) and evaporated till dryness. The residue and the precipitate were gathered and crystallized from EtOH. Yielding: Intermediate J2—5 g (42%).

Preparation of Intermediate J3

A solution of Intermediate J2 (4 g, 13.42 mmol), tert-Butyl-acrylate (7.8 mL, 53.7 mmol) and N,N-diisopropylethylamine (4.4 mL, 26.83 mmol) in DMF (30 mL) and ACN (80 mL) was stirred and degassed with $N_2$ for 10 minutes. Palladium acetate (0.3 g, 1.34 mmol) and Tri-O-tolylphosphine (0.82 g, 2.68 mmol) were added and the solution was heated at 180° C. using one multimode cavity microwave CEM MARS system with a power output ranging (50%) from 0 to 800 W for 30 min. The reaction mixture was filtered through a short pad of Celite® and washed with EtOAc. The organic layer was washed with water, dried over $MgSO_4$, filtered and evaporated to dryness. The residue was taken up EtOH, filtered and dried vacuum, Yielding: Intermediate J3—3.1 g (67%)

Preparation of Intermediate J4

Trifluoroacetic acid (17.5 mL, 227.25 mmol) was added to a solution of Intermediate J3 (3.1 g, 8.97 mmol) in $CH_2Cl_2$ (30 mL). The reaction mixture was stirred at room temperature for 30 minutes, concentrated under reduce pressure and then triturated with $Et_2O$, filtered off and dried under vacuum. Yielding: Intermediate J4—3.6 g (99%).

Preparation of Intermediate J8

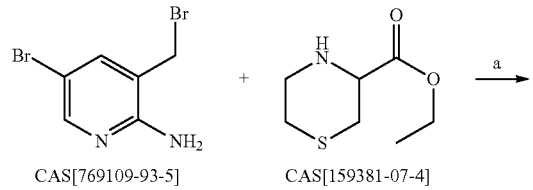

CAS[769109-93-5]    CAS[159381-07-4]

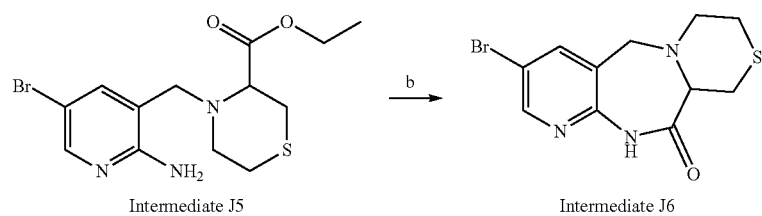

Intermediate J5    Intermediate J6

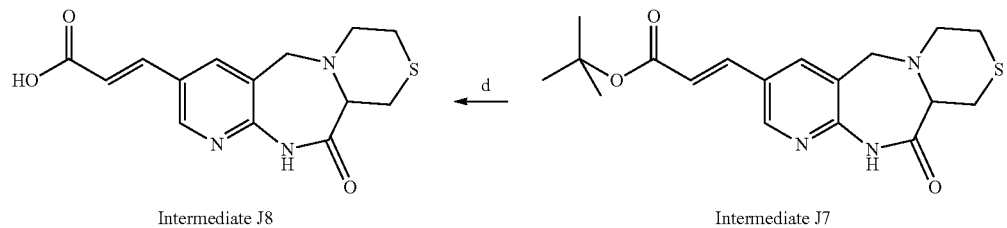

Intermediate J8    Intermediate J7

Preparation of Intermediate J5

Intermediate J5 was prepared in the same way as Intermediate J1, starting from 2-Amino-5-bromo-3-(bromomethyl)pyridine CAS [769109-93-5] and ethyl thiomorpholine-3-carboxylate hydrochloride[159381-07-4]. Yielding: 2 g, quantitative.

Preparation of Intermediate J6

Intermediate J6 was prepared in the same way as Intermediate J2, starting from Intermediate J5. Yielding: 0.65 g, 46%.

Preparation of Intermediate J7

Intermediate J7 was prepared in the same way as Intermediate J3, starting from Intermediate J6. Yielding: 0.57 g, 76%.

Preparation of Intermediate J8

Intermediate J8 was prepared in the same way as Intermediate J4, starting from Intermediate J7. Yielding: 0.66 g, 99%.

Preparation of Intermediate J14

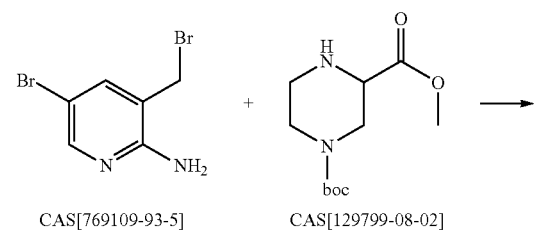

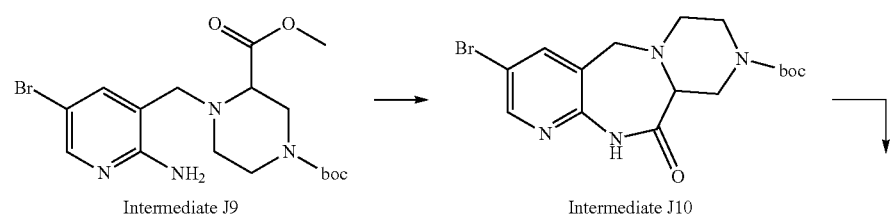

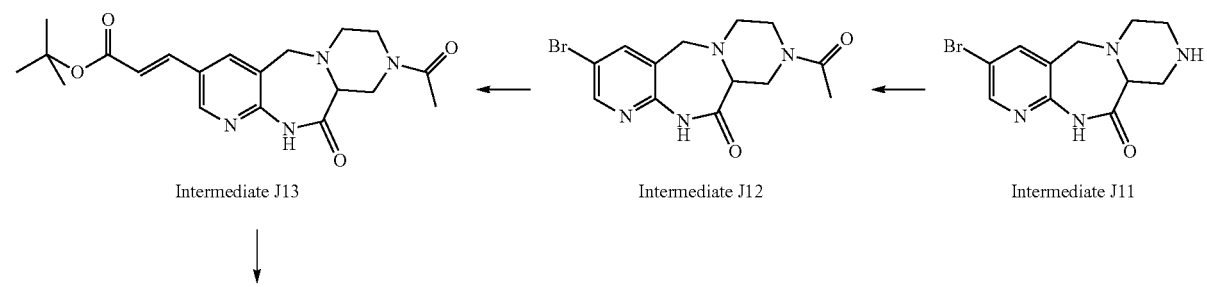

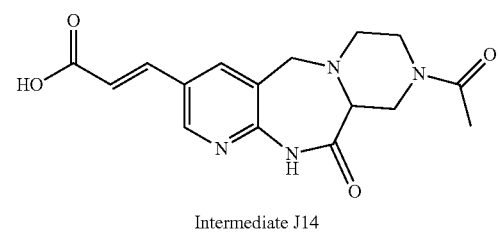

Preparation of Intermediate J9

Intermediate J9 was prepared in the same way as Intermediate J1, starting from 2-Amino-5-bromo-3-(bromomethyl)pyridine CAS [769109-93-5] and 1-(1,1-dimethyl-ethyl)-3-methylester-1,3-piperazine dicarboxylic acid [129799-08-2]. Yielding: as brown gum 36 g, quantitative.

Preparation of Intermediate J14

Intermediate J14 was prepared in the same way as Intermediate J4, starting from Intermediate J13. Yielding: as a white product 1 g, 94%.

Preparation of Intermediate J16

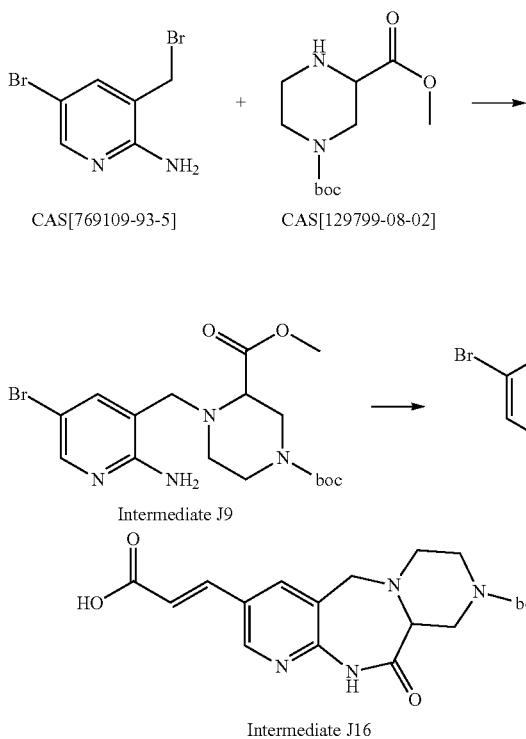

Preparation of Intermediate J10

Intermediate J10 was prepared in the same way as Intermediate J2, starting from Intermediate J9. Yielding: as white powder 13.8 g, 60%.

Preparation of Intermediate J11

Triflioroacetic acid (15.5 mL, 201 mmol) was added to a suspension of Intermediate J10 (8.00 g, 20.1 mmol) in DCM (90 mL). The mixture was stirred at room temperature for 20 hours and concentrated under reduced pressure. The residue was dissolved in dichloromethane (200 mL) and washed with saturated aqueous $NaHCO_3$ solution (200 mL). The aqueous layer was extracted with dichloromethane (20×50 mL). The combined organic layers were dried ($Na_2SO_4$), filtered and concentrated under reduced pressure. Yielding: as yellow solid 6 g, 100%.

Preparation of Intermediate J12

Acetyl chloride (1.86 mL, 26.0 mmol) was added to a solution of Intermediate J11 (5.95 g, 20.0 mmol) and triethylamine (3.91 mL, 28.0 mmol) in DCM (100 mL) at 0° C. The mixture was allowed to reach room temperature and was stirred for 3 days. The reaction mixture was diluted with dichloromethane (150 mL) and washed with water (250 mL). The organic layer was dried ($Na_2SO_4$), filtered and concentrated under reduced pressure. The residue was triturated in ethanol (30 mL) and vacuum-dried. Yielding: as a white solid 1.41 g, 21%.

Preparation of Intermediate J13

Intermediate J13 was prepared in the same way as Intermediate J3, starting from Intermediate J12. Yielding: as an orange foam 1.38 g, 86%.

Preparation of Intermediate J15

Intermediate J10 (4.30 g, 10.8 mmol) was suspended in a mixture of DMF (20 mL) and acetonitrile (60 mL). Methyl acrylate (2.92 mL, 32.5 mmol), diisopropylethylamine (3.96 mL, 22.7 mmol), and tri-o-tolylphosphine (0.659 g, 2.16 mmol) were added. The resulting mixture was purged with argon and palladium acetate (0.243 g, 1.08 mmol) was added. The mixture was purged with argon again and stirred under reflux (oil bath 110° C.) for 19 hours. The reaction mixture was concentrated under reduced pressure. The residue was dissolved in ethyl acetate (500 mL) and washed with saturated aqueous $NaHCO_3$ solution (300 mL), then with brine (300 mL). The organic layer was dried ($Na_2SO_4$), filtered and concentrated. The residue (6.15 g) was purified by column chromatography over silica gel (mobile phase gradient ethyl acetate/methanol 100/0 to 95/5). The product fractions were collected and the solvent was evaporated. The residue was triturated in ethanol (30 ml) and vacuum-dried (40° C., 1 h). Yielding: Intermediate J15 as a white solid 3.37 g, (77%).

Preparation of Intermediate J16

Sodium hydroxide (0.670 g, 16.7 mmol) and water (8 mL) were added to a solution of Intermediate J15 (3.37 g, 8.38 mmol) in THF (32 mL). The mixture was stirred at room temperature for 20 hours and then was concentrated under reduced pressure. The residue was dissolved in water (30 mL) and conc. HCl (~1.4 mL) was added until pH~5-6. The precipitate was filtered off on a glass frit, washed with water (15 mL) and vacuum-dried. Yielding: as a white solid 2.45 g, (75%).

Preparation of Intermediate J20

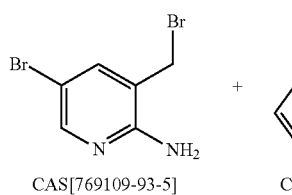

CAS[769109-93-5]    CAS[17325-26-7]

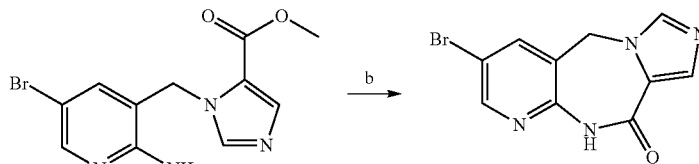

Intermediate J17                Intermediate J18

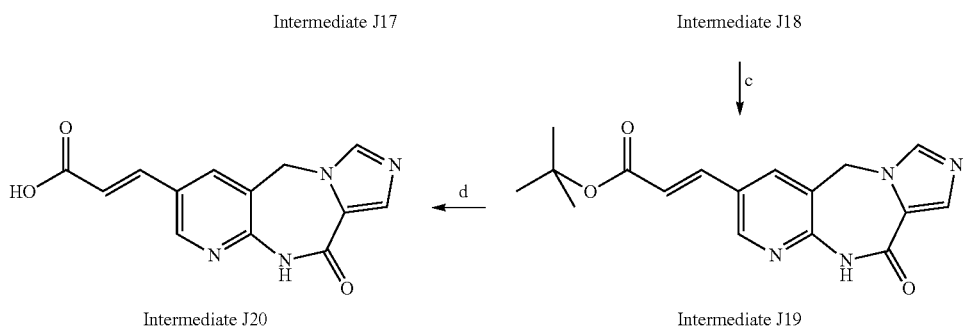

Intermediate J20                Intermediate J19

Intermediate J17
Intermediate J17 was prepared in the same way as Intermediate J1, starting from 2-Amino-5-bromo-3-(bromomethyl)pyridine CAS [769109-93-5] and 1H-Imidazole-5-carboxylic acid, methyl ester [17325-26-7]. Yielding: 1.42 g, 11%.

Intermediate J18
Intermediate J18 was prepared in the same way as Intermediate J2, starting from Intermediate J17. Yielding: 0.54 g, 49%.

Intermediate J19
Intermediate J19 was prepared in the same way as Intermediate J3, starting from Intermediate J18. Yielding: 0.17 g, 29%.

Intermediate J20
Intermediate J20 was prepared in the same way as Intermediate J4, starting from Intermediate J19. Yielding: 0.23 g, 66%.

Synthesis of Final Compounds K

Preparation of Compound K1

A solution of Intermediate A5 (0.22 g, 1.19 mmol), Intermediate J4 (0.4 g, 0.99 mmol), 1-hydroxybenzotriazole (0.16 g, 1.19 mmol), 1-(3-dimethylaminopropyl)-3-ethylcarbodiimide hydrochloride (0.23 g, 1.19 mmol) and triethylamine (0.42 mL, 2.98 mmol) in $CH_2Cl_2$ (8 mL) and THF (8 mL) was stirred overnight at room temperature. The mixture was poured out into water. The organic layer was extracted with $CH_2Cl_2$. The combined organic layers were washed with brine, dried over $MgSO_4$, filtered and concentrated. The residue was crystallized from EtOH, filtered off and dried under vacuum at 60° C. Yielding: Compound K1 0.14 g, (31%). m.p. 260° C.

$^1$H NMR (500 MHz, DMSO-$d_6$) δ 10.49-10.56 (m, 1H), 8.49-8.57 (m, 1H), 8.10-8.19 (m, 1H), 7.40-7.52 (m, 3H), 7.34 (t, J=7.57 Hz, 2H), 7.22-7.29 (m, 1H), 7.02-7.13 (m, 1H), 6.18-6.23 (m, 1H), 3.38-4.08 (m, 11H), 2.88-3.23 (m, 4H), 2.63-2.67 (m, 2H).

Preparation of Compound K2

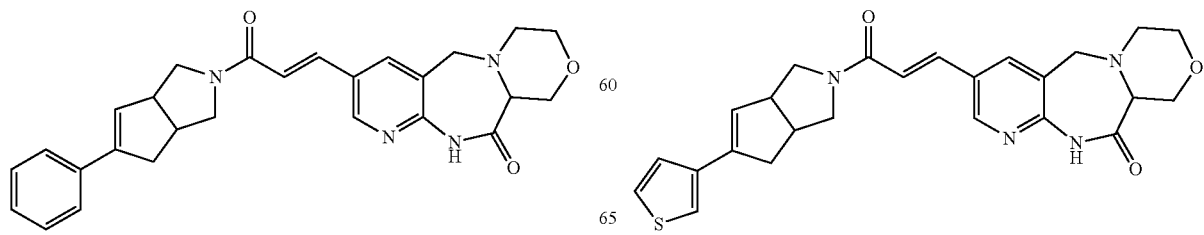

Compound K2 was prepared in the same way as Compound K1, starting from Intermediate A9 and Intermediate J4. Yielding: Compound K2 as a white powder 0.074 g, (43%). m.p.>250° C.

¹H NMR (400 MHz, DMSO-d₆) δ 10.51 (br. s., 1H), 8.47-8.58 (m, 1H), 8.08-8.19 (m, 1H), 7.31-7.58 (m, 4H), 6.99-7.12 (m, 1H), 6.01 (br. s., 1H), 3.36-4.08 (m, 11H), 2.81-3.23 (m, 4H), 2.58-2.53 (m, 2H).

Preparation of Compound K3

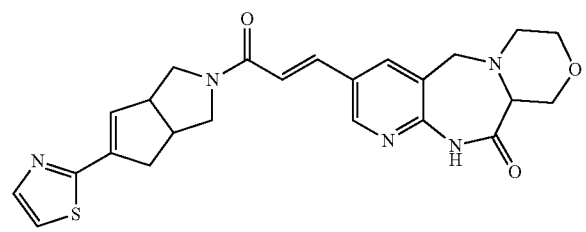 [SMILES: O=C1Nc2ncc(/C=C/C(=O)N3CC4C=C(c5nccs5)CC4C3)cc2CN2CCOCC12]

Compound K3 was prepared in the same way as Compound K1, starting from Intermediate A19 and Intermediate J4. Yielding: Compound K3 as a white powder 0.105 g, (61%). m.p.>260° C.

¹H NMR (500 MHz, DMSO-d₆) δ 10.50-10.58 (m, 1H), 8.50-8.58 (m, 1H), 8.10-8.19 (m, 1H), 7.81-7.83 (m, 1H), 7.69 (br. s., 1H), 7.42-7.49 (m, 1H), 7.02-7.11 (m, 1H), 6.43 (br. s., 1H), 3.42-4.07 (m, 11H), 2.96-3.25 (m, 4H), 2.58-2.79 (m, 2H).

Preparation of Compound K4

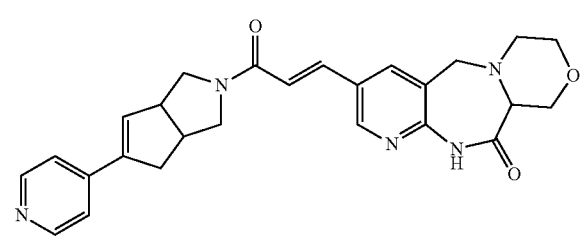 [SMILES: O=C1Nc2ncc(/C=C/C(=O)N3CC4C=C(c5ccncc5)CC4C3)cc2CN2CCOCC12]

Compound K4 was prepared in the same way as Compound K1, starting from Intermediate A13 and Intermediate J4. Yielding: Compound K4 as a white powder 0.093 g, (55%). m.p. 212° C.

¹H NMR (400 MHz, DMSO-d₆) δ 10.51 (br. s., 1H), 8.47-8.58 (m, 3H), 8.08-8.19 (m, 1H), 7.31-7.58 (m, 3H), 6.99-7.12 (m, 1H), 6.51 (br. s., 1H), 3.36-4.08 (m, 11H), 2.81-3.23 (m, 4H), 2.58 (m, 2H).

Preparation of Compound K5

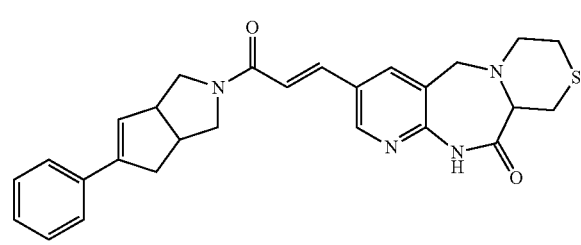 [SMILES: O=C1Nc2ncc(/C=C/C(=O)N3CC4C=C(c5ccccc5)CC4C3)cc2CN2CCSCC12]

Compound K5 was prepared in the same way as Compound K1, starting from Intermediate A5 and Intermediate J8. Yielding: Compound K5 as a white powder 0.119 g, (59%). m.p. 214° C.

¹H NMR (400 MHz, DMSO-d₆) δ 10.56 (br. s., 1H), 8.53-8.61 (m, 1H), 8.09-8.17 (m, 1H), 7.41-7.55 (m, 3H), 7.34 (t, J=7.6 Hz, 2H), 7.21-7.28 (m, 1H), 7.01-7.12 (m, 1H), 6.21 (br.s., 1H), 3.39-4.11 (m, 7H), 2.81-3.25 (m, 5H), 2.52-2.75 (m, 5H).

Preparation of Compound K6

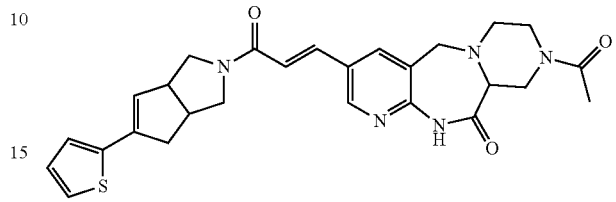

Compound K6 was prepared in the same way as Compound K1, starting from Intermediate J14 and Intermediate A20. Yielding: Compound K6 as a white powder 0.102 g, (37%). m.p. 215-230° C.

Preparation of Compound K7

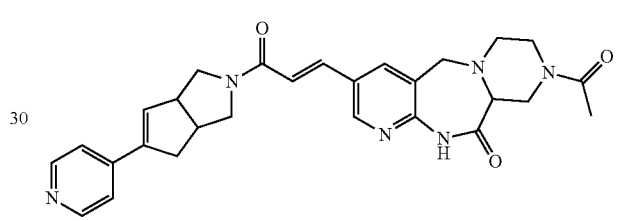

The compound K7 was prepared in the same way as Compound K1, starting from Intermediate J14 and Intermediate A13. Yielding: Compound K7 as a white powder 0.160 g, (60%). m.p. 142-246° C.

Preparation of Compound K8

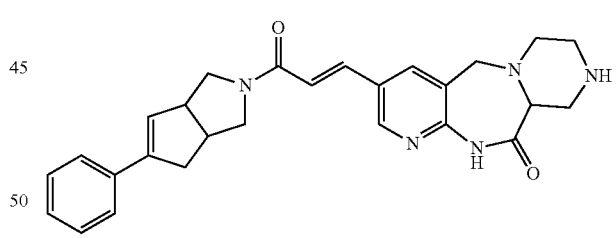

Trifluoroacetic acid (0.69 mL, 9.00 mmol) was added to a solution of Compound K9 (0.500 g, 0.900 mmol; see below) in DCM (6 mL). The reaction mixture was stirred at room temperature for 18 hours. The residue was dissolved in dichloromethane (100 mL) and washed with saturated aqueous NaHCO₃ solution (100 mL). The aqueous layer was extracted with dichloromethane (3×20 mL). The combined organic layers were dried (Na₂SO₄), filtered and concentrated. The residue (0.42 g) was triturated in EtOH (2×~5 mL) and vacuum-dried (50° C., 6 h). Yielding: Compound K8 as a white solid 0.285 g (70%). m.p: 191-216° C.

Preparation of Compound K9

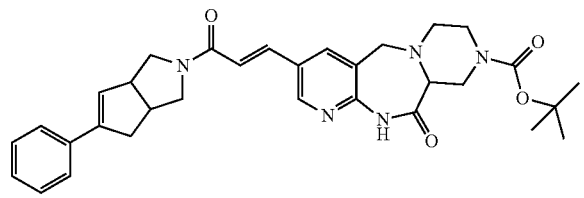 [SMILES: CC(C)(C)OC(=O)N1CCN2Cc3cc(/C=C/C(=O)N4CC5C=C(c6ccccc6)CC5C4)cnc3NC(=O)C2C1]

The Compound K9 was prepared in the same way as compound K1, starting from Intermediate J16 and Intermediate A5. Yielding: Compound K9q as a white powder 1.7 g, (76%).

Preparation of Compound K10

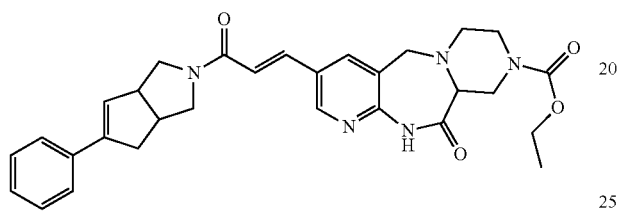

Ethyl chloroformate (0.046 mL, 0.483 mmol) was added to a solution of Compound K8 (0.200 g, 0.439 mmol) and triethylamine (0.122 mL, 0.878 ml) in DCM (2 mL) at 0° C. The reaction mixture was stirred at room temperature for 20 hours. The reaction mixture was diluted with dichloromethane (50 mL) and washed with water (50 mL), then with aqueous NaHCO₃ saturated solution (50 mL). The organic layer was dried (Na₂SO₄), filtered and concentrated to dryness. The residue (0.207 g) was purified by column chromatography over silica gel (eluent: dichloromethane/methanol, 98/2 to 95/5). The product fractions were collected and the solvent was evaporated. The residue was triturated in ethanol (2×5 mL) and vacuum-dried (50° C., 20 h). Yielding: Compound K10 as a white solid 0.055 g (24%). m.p: 242-267° C.

Preparation of Compound K11

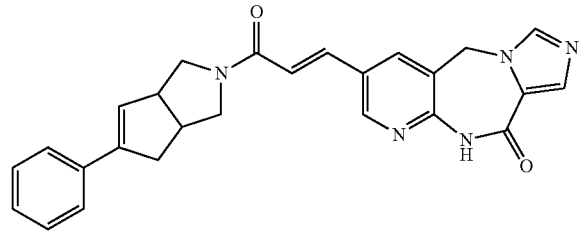 [SMILES: O=C1Nc2ncc(/C=C/C(=O)N3CC4C=C(c5ccccc5)CC4C3)cc2Cn2cncc21]

The Compound K11 was prepared in the same way as compound K1, starting from Intermediate J20 and Intermediate A5. Yielding: Compound K11 as a white powder 0.035 g, (25%). m.p: 220-270° C.

Preparation of Compound K12

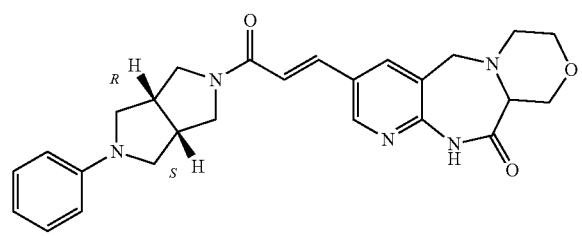

Compound K12 was prepared in the same way as Compound K1, starting from Intermediate J21 (see below) and (Intermediate J4). Yielding: Compound K12 as a white powder 0.161 g, (55%). m.p.>250° C.

$^1$H NMR (500 MHz, DMSO-$d_6$) δ 10.54 (s, 1H), 8.55 (s, 1H), 8.14 (s, 1H), 7.48 (d, J=15.4 Hz 1H), 7.16 (t, J=7.88 Hz, 2H), 7.06 (d, J=15.4 Hz, 1H), 6.61 (t, J=7.88 Hz, 1H), 6.55 (d, J=7.88 Hz, 2H), 3.38-4.02 (m, 13H), 2.98-3.21 (m, 5H), 2.61-2.67 (m, 1H).

Preparation of Intermediate J21

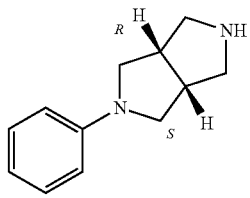

Trifluoroacetic acid (0.57 mL, 7.42 mmol) was added to a solution of Intermediate J22 (0.214 g, 0.74 mmol; see below) in DCM (2.2 mL). The reaction mixture was stirred at room temperature for 3 hours, water and DCM were added, K₂CO₃ 10% was added to basify and the organic layer was separated, washed with water, dried (MgSO₄) and evaporated till dryness. Yielding: Intermediate J21 as an oil 120 mg (86%).

Preparation of Intermediate J22

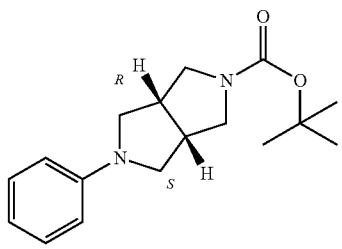

A solution of bromobenzene (108-86-1, 0.11 mL, 1.09 mmol), cis-2-boc-hexa-hydropyrrolo[3.4]pyrrole (141449-85-6, 0.3 g, 1.41 mmol) and sodium tert butoxide (865-48-5, 0.31 g, 3.26 mmol) in toluene extra dry with molecular sieves (10 mL) was stirred and degassed with N₂ for 10 minutes. Pd₂(dba)₃ (52409-22-0, 0.1 g, 0.11 mmol) and 2-(di-t-butylphosphino)biphenyl (224311-51-7, 0.032 g, 0.11 mmol) were added and the resulting mixture was heated at 140° C. using a single mode microwave (Biotage Initiator EXP 60) with a power output ranging from 0 to 400 W for 25 minutes. Water and EtOAc were added, the organic layer was separated and then dried over MgSO₄, filtered off and concentrated. The residue was purified by chromatography over silica gel (15-40 µm, 30 g, mobile phase: Heptane/EtOAc 80/20). The Pure fractions were collected and concentrated. Yielding: Intermediate J22—0.214 g (68%).

Example L

Preparation of compounds in which R$^x$=(iii) and the Z²-containing ring is 8-membered

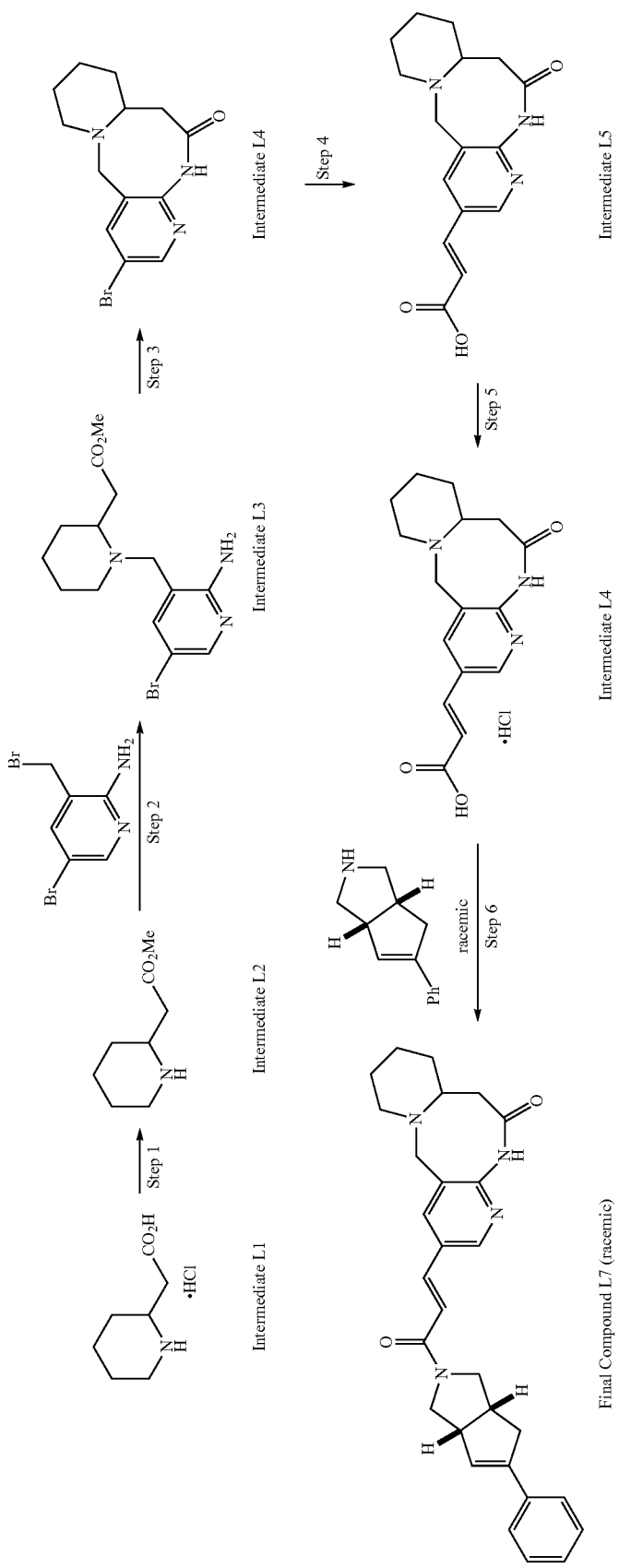

General:

All experiments for the synthesis of Final Compound L7 were carried out under argon atmosphere using anhydrous solvents.

Step 1:

The preparation of Intermediate L2 was performed by reaction in the presence of Intermediate L1, $SOCl_2$ (e.g. 4 equivs) and MeOH (e.g. at reflux).

Step 2: Preparation of Intermediate L3

A mixture of Intermediate L2 (1.47 g, 9.35 mmol), the HBr salt of 3-bromo-5-bromomethyl-6-amino-pyridine (3.24 g, 9.35 mmol) and N-ethyldiisopropylamine (6.50 ml, 37.3 mmol) in acetonitrile (40 ml) was stirred at reflux for 3 h, then concentrated under reduced pressure. The residue was taken up in aqueous saturated sodium bicarbonate (70 ml) and extracted with dichloromethane (3×70 ml). The combined organic layers were washed with aqueous saturated sodium bicarbonate (2×100 ml), dried over sodium sulfate, filtered and then concentrated under reduced pressure. The crude compound was purified by column chromatography over silica gel (eluent: chloroform) and vacuum-dried to yield Intermediate L3 (2.67 g, 83%) as a yellowish oil.

Step 3: Preparation of Intermediate L4

Sodium hydride (60% dispersion in mineral oil, 0.437 g, 10.9 mmol) was added to a solution of Intermediate L3 (2.67 g, 7.80 mmol) in DMF (85 ml). The resulting mixture was stirred at room temperature for 3 h, then quenched by addition of water (10 ml) and concentrated under reduced pressure. The residue was taken up in water (80 ml) and extracted with dichloromethane/methanol (9/1, 5×80 ml). The combined organic layers were concentrated under reduced pressure. The residue was taken up in dichloromethane (100 ml), washed with saturated brine (5×80 ml), dried over sodium sulfate and concentrated under reduced pressure. The obtained product was triturated with diethyl ether (10 ml), collected by filtration on a glass frit, rinsed with diethyl ether (10 ml) and vacuum-dried to yield Intermediate L4 (1.25 g, 52%) as a yellowish solid.

Melting point: 216.1-225.6° C. under decomposition (Buchi M-560, 1° C./min).

Step 4: Preparation of Intermediate L5:

Intermediate L4 (0.270 g, 0.870 mmol) was suspended in a mixture of DMF (3 ml) and acetonitrile (10 ml). Tert-butyl acrylate (0.510 ml, 3.48 mmol), N-ethyldiisopropylamine (0.320 ml, 1.84 mmol) and tri(o-tolyl)phosphine (0.0530 g, 0.174 mmol) were added. The resulting mixture was purged with argon and palladium acetate (0.0195 g, 0.0870 mmol) was added. The mixture was purged again with argon, stirred under reflux overnight and at room temperature for 2 days, then concentrated under reduced pressure. The residue was taken up in aqueous saturated sodium bicarbonate (20 ml) and extracted with dichloromethane (3×20 ml). The combined organic layers were dried over sodium sulfate, filtered and concentrated under reduced pressure. The crude residue was purified by column chromatography over silica gel (eluent: dichloromethane/methanol 98/2). The obtained product was taken up in dichloromethane (10 ml), washed with brine (3×20 ml), dried over sodium sulfate, filtered and concentrated under reduced pressure to yield Intermediate L5 (0.253 g, 81%) as a yellowish gum.

Step 5: Preparation of Intermediate L6:

A mixture of Intermediate L5 (0.253 g, 0.708 mmol) and 4M hydrogen chloride in 1,4-dioxane (7.00 ml, 28.0 mmol) was stirred at room temperature overnight and at 40° C. for 25 h. The precipitate was filtered on a glass frit, washed with dioxane (2×2 ml) and diethyl ether (3×2 ml) and dried under vacuum to yield Intermediate L6 (0.174 g, 67%) as a yellowish solid hydrochloride salt (1.8 eq. HCl according to chloride titration).

Step 6: Preparation of Final Compound L7:

1-(3-Dimethylaminopropyl)-3-ethylcarbodiimide hydrochloride (0.110 g, 0.574 mmol) was added to a mixture of (HCl salt of) Intermediate L7 (1.8 eq HCl) (0.140 g, 0.381 mmol), the relevant bicycle (Intermediate A5; 0.099 g, 0.534 mmol), 1-hydroxybenzotriazole monohydrate (0.070 g, 0.457 mmol) and N-ethyldiisopropylamine (0.400 ml, 2.29 mmol) in DMF/DMSO (1.2 ml/1.2 ml). The mixture was stirred at room temperature overnight, then diluted with dichloromethane (120 ml), washed with water (5×25 ml), dried over sodium sulfate, filtered and concentrated under reduced pressure. The residue was purified by column chromatography over silica gel (eluent: chloroform/methanol 100/0 to 98/2). The obtained compound was triturated with diethyl ether (2 ml), collected by filtration on a glass frit, washed with diethyl ether (2 ml) and vacuum-dried to yield Final Compound L7 (0.0773 g, 43%) as an off-white solid.

Melting point: 214.9-232.7° C. under decomposition (Buchi M-560, 1° C./min).

Example M

Synthesis of Intermediates in which $X^x$ Represents N

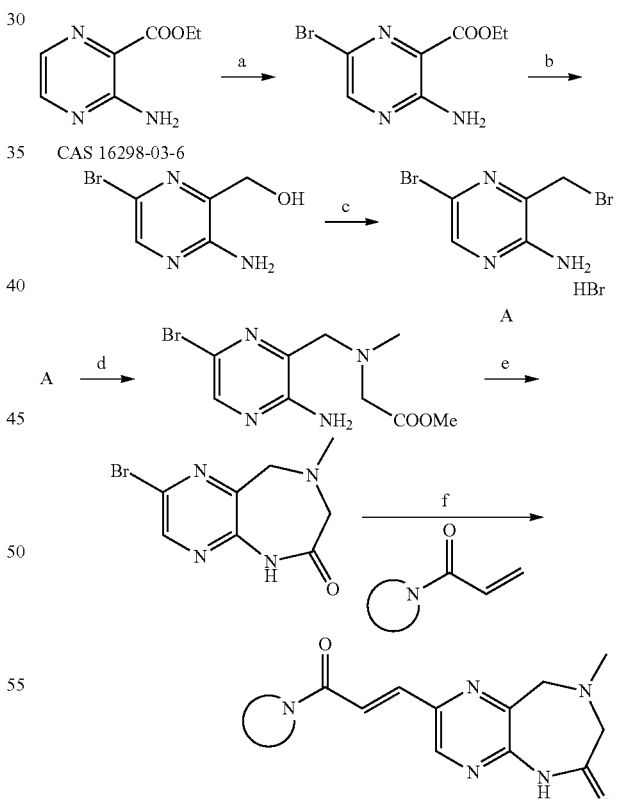

Conditions:
a) NBS, ACN, reflux, 3 h, 70%; b) LiAlH$_4$ 1M in THF, THF, 5° C. to RT, o.n., 20%; c) PBr$_3$, DCM, RT, o.n., 90%; d) sarcosine ethyl ester, Et$_3$N, DMF, μw, 120° C., 20 min, 53%; e) NaH, DMF, RT, 3 h, 25%; f) DIEA, Pd(OAc)$_2$, tri-O-tolylphosphine, ACN, DMF, μw, 180° C., 25 min.

Hence, intermediate compounds (and therefore final compounds) in which the $R^x$ ring represents a monocyclic, bicyclic or tricyclic ring in which $X^x$ represents N may be prepared in accordance with the procedure described in this Example M.

X. Compound Identification

X1. LCMS

For LCMS-characterization of the compounds of the present invention, the following methods were used.

General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

General Procedure B

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters. Nitrogen was used as the nebulizer gas. Data acquisition was performed with a Waters-Micromass MassLynx-Openlynx data system.

Method 1

In addition to the general procedure A: reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

Method 2

In addition to the general procedure A: reversed phase UPLC was carried out on a Waters Acquity BEH (bridged ethylsiloxane/silica hybrid) C18 column (1.7 µm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 µl was used. Cone voltage was 20V for positive and negative ionization mode. Mass spectra were acquired by scanning from 100 to 1000 in 0.2 seconds using an interscan delay of 0.1 seconds.

Method 3

In addition to the general procedure B: reversed phase HPLC was carried out on a Waters X-bridge C18 column (3.5 µm, 4.6×100 mm) with a flow rate of 0.8 ml/min. Two mobile phases (mobile phase A: 100% 7 mM ammonium acetate; mobile phase B: 100% acetonitrile) were employed to run a gradient condition from 80% A and 20% B (hold for 0.5 minute) to 90% B in 4.5 minutes, 90% B for 4 minutes and reequilibrated with initial conditions for 3 minutes. An injection volume of 5 µl was used. Cone voltage was 20 V for positive and negative ionization mode. Mass spectra were acquired by scanning from 100 to 1000 in 0.4 seconds using an interscan delay of 0.3 seconds.

Method 4

In addition to the general procedure B: reversed phase HPLC was carried out on a Waters Atlantis C18 column (5 µm, 3.9×100 mm) with a flow rate of 0.8 ml/min. Three mobile phases (mobile phase A: 100% 7 mM ammonium acetate; mobile phase B: 100% acetonitrile; mobile phase C: 0.2% formic acid+99.8% ultra-pure water) were employed to run a gradient condition from 50% A and 50% C (hold for 1.5 minute) to 10% A, 80% B and 10% C in 4.5 minutes, hold for 4 minutes and reequilibrated with initial conditions for 3 minutes. An injection volume of 5 µl was used. Cone voltage was 20 V for positive and negative ionization mode. Mass spectra were acquired by scanning from 100 to 1000 in 0.4 seconds using an interscan delay of 0.3 seconds.

Method 5

The HPLC measurement was performed using an HPLC 1100/1200 (Agilent) system comprising a quaternary pump with degasser, an autosampler, a diode-array detector (DAD) and a column as specified in the respective methods below, the column is hold at room temperature. The MS detector (MS-Agilent simple quadripole) was configured with an electrospray-APCI ionization source. Nitrogen was used as the nebulizer gas. Data acquisition was performed with a Chemstation data system.

Reversed phase HPLC was carried out on a Nucleosil C18 column (3 µm, 3×150 mm) with a flow rate of 0.42 ml/min. Two mobile phases (mobile phase A: water/TFA (0.1%); mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 µl was used. The capillary voltage was 2 kV, the corona discharge was held at 1 µA and the source temperature was maintained at 250° C. A variable voltage was used for the fragmentor. Mass spectra were acquired in electrospray ionization and APCI in positive mode, by scanning from 100 to 1100 amu.

Method 6

This method employs the following parameters:
Agilent 1200 LC 6100 MS
Column: HALO C18(4.6*50 mm 2.7 µm)
Flow: 1.8 ml/min
A: $H_2O$ (0.05% FA) B: CH3CN(0.05% FA)

| Time (min) | Conc: (B %) |
|---|---|
| 0 | 5 |
| 1 | 95 |
| 2 | 95 |
| 2.01 | 5 |
| 2.5 | 5 |

X2. Melting Points

For a number of compounds, melting points were obtained with a Kofler hot bench, consisting of a heated plate with linear temperature gradient, a sliding pointer and a temperature scale in degrees Celsius.

For a number of compounds, melting points were determined using differential scanning calorimetry (DSC). Melting points were measured with a temperature gradient of 10° C./minute starting at 25° C. Maximum temperature was 350° C.

For a number of compounds, melting points were obtained with a Büchi melting point apparatus B-560. The heating medium was a metal block. The melting of the sample was visually observed by a magnifying lense and a big light contrast. Melting points were measured with a temperature gradient of either 3 or 10° C./minute. Maximum temperature was 300° C.

The remaining melting points were determined using open capillary tubes.

TABLE X

LC/MS data and melting points

| Cpd. No. | Rt | MH+ | LCMS Method | Melting Point (method) |
|---|---|---|---|---|
| 1 | 2.92 | 451 | 2 | 214° C. (Kofler) |
| 2 | 3.02 | 426 | 2 | 202° C. (Kofler) |
| 3 | 2.8 | 437 | 2 | 238° C. (Kofler) |
| 4 | 2.71 | 443 | 2 | 236.37° C./−61.44 Jg-1 (DSC) |
| 5 | 2.84 | 457 | 2 | 208.43° C./−41.55 Jg-1 (DSC) |
| 6 | 2.38 | 458 | 2 | 230.99° C./−66.52 Jg-1 (DSC) |
| 7 | 2.91 | 467 | 2 | 218.79° C./−68.97 Jg-1 (DSC) |
| 8 | 2.28 | 452 | 2 | 202.82° C./−74.76 Jg-1 (DSC) |
| 9 | 2.15 | 438 | 2 | 196° C. (Kofler) |
| 10 | 2.69 | 374 | 2 | 251.61° C./−93.37 Jg-1 (DSC) |
| 11 | 3.2 | 440 | 2 | 140° C. (Kofler) |
| 12 | 2.81 | 437 | 2 | 184° C. (Kofler) |
| 13 | 3.21 | 436 | 2 | 120° C. (Kofler) |
| 14 | 2.7 | 451 | 2 | 239.70° C./−77.87 Jg-1 (DSC) |
| 15 | 2.6 | 332 | 2 | 236° C. (Kofler) |
| 16 | 2.31 | 455 | 2 | 173.34° C./−52.37 Jg-1 (DSC) |
| 17 | 2.09 | 452 | 2 | >250° C. (Kofler) |
| 18 | 2.86 | 446 | 2 | 216.42° C./−74.09 Jg-1 (DSC) |
| 19 | 3.34 | 454 | 2 | 184.41° C./−52.25 Jg-1 (DSC) |
| 30 | 2.28 | 468 | 2 | 142° C. (Kofler) |
| 31 | 2.31 | 471 | 2 | 89.36° C./−102.39 Jg-1 (DSC) |
| 32 | 2.39 | 474 | 2 | 207° C. (Kofler) |
| 33 | 2.83 | 473 | 2 | 205° C. (Kofler) |

Table of compounds in which R$^x$ is (ii) i.e. a bicycle

| Cpd. No. | Rt | MH+ | LMSC Method | Melting Point (method) |
|---|---|---|---|---|
| 35 | 2.5 | 394 | 2 | >250° C. (Kofler) |
| 36 | 2.04 | 389 | 2 | >260° C. (Kofler) |
| 37 | 2.73 | 388 | 2 | >260° C. (Kofler) |
| 38 | 2.45 | 401 | 2 | >260° C. (Kofler) |
| 39 | 2.69 | 402 | 2 | 266.57° C./−85.58 J/g (DSC) |
| 40 | 2.37 | 407 | 2 | 228° C. (Kofler) |
| 41 | 2.6 | 408 | 2 | 152° C. (Kofler) |
| 46 | 2.45 | 401 | 2 | >260° C. (Kofler) |
| 47 | 2.43 | 401 | 2 | >260° C. (Kofler) |
| 48 | 1.89 | 408 | 2 | 240° C. (Kofler) |
| 49 | 2.11 | 409 | 2 | 260.34° C./−76.98 J/g (DSC) |
| 50 | 2.52 | 415 | 2 | 202° C. (Kofler) |
| 51 | 2.63 | 388 | 2 | >250° C. (Kofler) |
| 52 | 1.81 | 402 | 2 | >260° C. (Kofler) |
| 53 | 2.69 | 402 | 2 | 272.58° C./−109.87 J/g (DSC) |
| 54 | 2.01 | 403 | 2 | 154° C. (Kofler) |
| 55 | 1.92 | 389 | 2 | 156° C. (Kofler) |
| 56 | 2.04 | 406 | 2 | 149° C. (Kofler) |
| 57 | 1.83 | 405 | 2 | 228° C. (Kofler) |
| 58 | 1.38 | 418 | 6 | 178.9-179.8 degree C (X-4B) |
| 59 | 2.37 | 448 | 2 | 114° C. (Kofler) |
| 60 | 2.41 | 418 | 2 | 178° C. (Kofler) |
| 63 | 3.11 | 430 | 2 | 224.90° C./−45.96 Jg-1 (DSC) |
| 64 | 2.56 | 437 | 2 | 223.55° C./−56.069 Jg-1 (DSC) |
| 65 | 2.44 | 431 | 2 | 113.11° C./−42.09 Jg-1 (DCS) |
| 66 | 2.43 | 415 | 2 | 226° C. (Kofler) |
| 67 | 2.32 | 471 | 2 | |
| 68 | 2.61 | 443 | 2 | 196° C. (Kofler) |

Table of compounds in which R$^x$ is (iii) i.e. a tricycle

| Cpd. No. | Rt | MH+ | LCMS Method | Melting Point (method) |
|---|---|---|---|---|
| 69 | 2.54 | 457 | 2 | 242° C. (Kofler) |
| 70 | 2.49 | 463 | 2 | |
| 71 | 13.04 | 438 | 5 | |
| 72 | 14.7 | 438 | 5 | |
| 73 | 14.01 | 439 | 5 | |
| 74 | 2.01 | 464 | 2 | >260° C. (Kofler) |
| 75 | 13.33 | 504 | 5 | |
| 76 | 2.54 | 471 | 2 | 278.12° C. (DSC) |
| 77 | 2.76 | 473 | 2 | |
| 78 | 2.54 | 457 | 2 | 242° C. (Kofler) |
| 79 | 12.78 | 456 | 5 | |
| 80 | 1.92 | 458 | 2 | |
| 81 | 2.36 | 470 | 2 | 230-232° C. (Kofler) |
| 82 | 2.52 | 484 | 2 | >270° C. (Kofler) |
| 83 | 2.41 | 512 | 2 | 262-264° C. (Kofler) |
| 84 | 10.25 | 499 | 5 | |
| 85 | 1.94 | 461 | 2 | 226° C. (Kofler) |
| 87 | 2.43 | 460 | 2 | >250° C. (Kofler) |
| 88 | 14.13 | 528 | 5 | |
| 90 | | | | 214.9-232.7° C. (Buchi) |

Y. Pharmacological Examples

Y.1 FabI Enzyme Inhibition: *Staphylococcus aureus* FabI Enzyme Inhibition Assay FabI enzyme inhibition assays were carried out in half-area, 384-well microtitre plates. Compounds were evaluated in 40-µl assay mixtures containing 100 mM NaADA, pH 6.5 (ADA=N-[2-acetamido]-2iminodiacetic acid), 250 µM crotonoyl-CoA, 625 µM NADH and 50 µg/ml *S. aureus* ATCC 29213 FabI. Inhibitors were typically varied over the range of 50 to 0.39 µM. The reaction mixtures were incubated for 30 minutes at room temperature and the reaction was stopped by adding 200 mM Tris buffer (pH 9.0) to create a pH-shift. The consumption of NADH was monitored by measuring the change in absorbance at 340. By comparing sample readings to those of negative (absence of compound) and positive (absence of enzyme) controls, the percent inhibition of enzymatic activity of the compounds was determined A best-fit curve is fitted by a minimum of squares method. From this an $IC_{50}$-value (expressed in µg/ml), resulting in 50% inhibition of enzymatic activity, was obtained.

The results are depicted in the table(s) below (FabI activity).

Y.2 In Vitro Method for Testing Compounds for Antibacterial Activity Against Various Bacterial Strains Preparation of Bacterial Suspensions for Susceptibility Testing The following bacteria were used: *Staphylococcus aureus* ATCC 29213, methicillin-resistant *Staphylococcus aureus* (MRSA) ATCC 700788 and *Escherichia coli* ATCC 35218. The bacteria used in this study were grown overnight in flasks containing 100 ml Mueller-Hinton broth (Difco cat. nr. 0757-17) in sterile de-ionized water, with shaking, at 37° C. Stocks were store at −70° C. until use.

Bacteria were incubated on a tryptic soy agar plate containing 5% sheep blood (Becton Dickinson cat. nr. 254053) for 18-24 hours at 35° C. in aerobic conditions (first passage). For the second passage, fresh Mueller-Hinton broth is inoculated with 5-10 colonies and grown overnight at 35° C. until turbidity (reaching log-phase) in aerobic conditions is reached. The bacterial suspension is then adjusted to 0.5 McFarland density and further diluted 1:100 in Mueller Hinton broth medium. This is used as inoculum.

The result(s) are depicted the table below (for STA ATCC 29213).

Antibacterial Susceptibility Testing: $IC_{90}$ Determination

MIC assays were performed by the broth microdilution method in a 96-well format (flat-bottom microtitre plates) with a final volume of 0.1 ml Mueller Hinton broth containing two-fold serial dilutions of compounds and inoculated with $5 \times 10^5$ CFU/ml of bacteria (standard inoculum size according to CLSI guidelines). Inhibitors are typically varied over the range of 63 to 0.49 µM. The final DMSO concentration in the assay was 1.25% (maximum tolerable DMSO concentration=6%). In the assays where the effect of human serum on the activity of the compounds against *S. aureus* was tested, human serum was added at a final concentration of 10%. The plates were incubated at 35° C. for 16-20 hours. At the end of incubation the bacterial growth was quantified fluorometrically. For this, resazurin was added to all wells and the plates were re-incubated. The incubation time is dependent on the type of bacteria. A change in color from blue to pink indicated the growth of bacteria. The fluorescence was read in computer-controlled fluorometer (Fluoroskan Ascent FL, Labsystems) at an excitation wavelength 540 nm and an emission wavelength of 590 nm. The % growth inhibition achieved by the compounds was calculated according to standard methods. The $IC_{90}$ (expressed in µg/ml) was defined as the 90% inhibitory concentration for bacterial growth. A panel of reference compounds were simultaneously tested for QC approval.

The results are depicted in the table(s) below (STA+10% HS).

Cytotoxicity Assays

Cytotoxicity of the compounds was evaluated using the MTT assay. Human HelaM cells grown in 96-well plates were exposed to serial dilutions of the tested compounds (final volume of 0.2 ml) and incubated for 72 hours at 37° C. and 5% $CO_2$. Inhibitors are typically varied over the range of 25 to 0.8 µM. The final DMSO concentration in the assay is 0.5%. MTT (3-(4,5-Dimethylthiazol-2-yl)-2,5-diphenyltetrazolium bromide, a tetrazole) was added and reduced to purple formazan only in living cells. Solubilization of the formazan crystals was achieved by adding 100 µl 2-propanol. Cell viability was determined by measuring the absorbance of the reduced formazan, giving a purple color, at 540 nm and 690 nm. The absorbance measured at 690 nm was automatically subtracted from the absorbance at 540 nm, to eliminate the effects of non-specific absorption. The percent cytotoxicity achieved by the compounds was calculated according to standard methods. Cytotoxicity is reported as $CC_{50}$, the concentration that causes a 50% reduction in cell viability.

The results are depicted in the table(s) below (HELAM).

Biological Testing

Compounds of the invention/examples were tested in assays described above and were found to exhibit a certain inhibition as depicted in the tables below.

Table of compounds in which $R^x$ is (i) i.e. a monocycle

| Example | Cpd No. | STA (361.159) IC90 µg/mL | STA + 10% HS (361.169) IC90 µg/mL | HELAM (222.125) CC50 µg/mL | FabI (300.235) IC50 µg/mL |
|---|---|---|---|---|---|
| 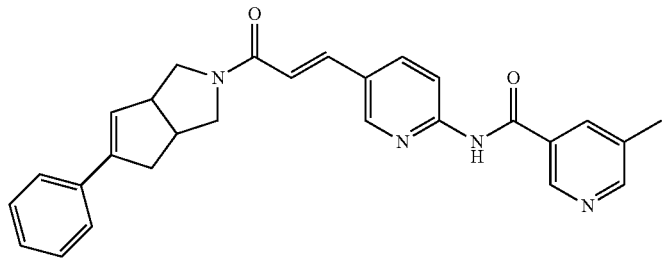 [SMILES: Cc1cncc(C(=O)Nc2ccc(/C=C/C(=O)N3CC4C=C(c5ccccc5)CC4C3)cn2)c1] | 1 | 0.17 | 0.67 | >4.50 | 0.82 |

-continued

Table of compounds in which R^x is (i) i.e. a monocycle

| Example | Cpd No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| (structure) | 2 | 0.21 | 1.66 | 7.57 | 3.23 |
| (structure) | 3 | 0.21 | 0.79 | 1.23 | 0.79 |
| (structure) | 4 | <0.21 | 0.28 | 0.97 | |
| (structure) | 5 | <0.22 | 0.36 | 10.10 | 0.79 |
| (structure) | 6 | <0.22 | <0.22 | >11.49 | |

Table of compounds in which R^x is (i) i.e. a monocycle
| Example | Cpd No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| 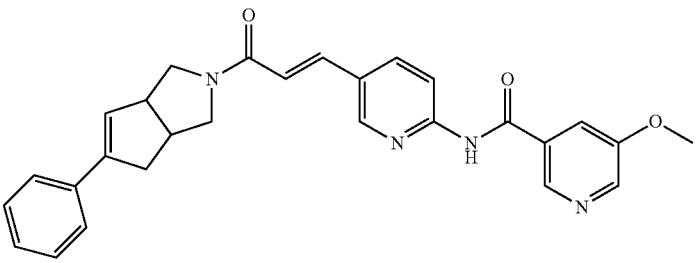 [SMILES: COc1cncc(C(=O)Nc2ccc(/C=C/C(=O)N3CC4C=C(c5ccccc5)CC4C3)cn2)c1] | 7 | <0.22 | 0.42 | >11.72 | 1.12 |
| 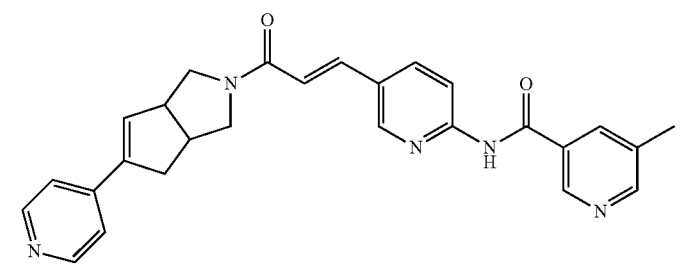 [SMILES: Cc1cncc(C(=O)Nc2ccc(/C=C/C(=O)N3CC4C=C(c5ccncc5)CC4C3)cn2)c1] | 8 | 0.316 | 0.39782 | >11.34 | 0.56 |
| 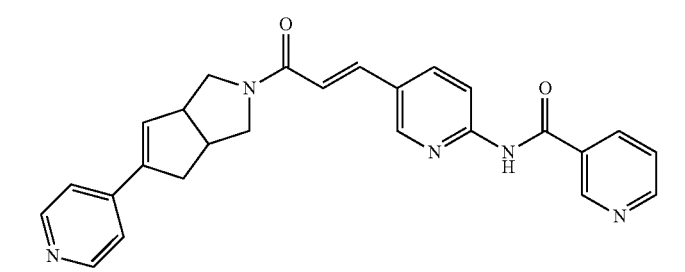 [SMILES: O=C(Nc1ccc(/C=C/C(=O)N2CC3C=C(c4ccncc4)CC3C2)cn1)c1cccnc1] | 9 | 0.34 | 0.39 | >10.99 | |
| 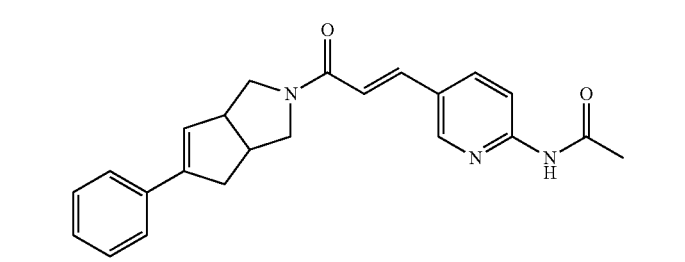 [SMILES: CC(=O)Nc1ccc(/C=C/C(=O)N2CC3C=C(c4ccccc4)CC3C2)cn1] | 10 | 0.34 | 0.50 | >9.38 | 0.40 |
| 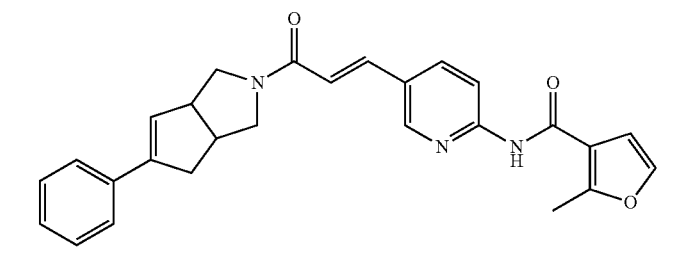 [SMILES: Cc1occc1C(=O)Nc1ccc(/C=C/C(=O)N2CC3C=C(c4ccccc4)CC3C2)cn1] | 11 | 0.47 | 3.33 | 5.16 | 1.42 |

-continued

Table of compounds in which R^x is (i) i.e. a monocycle

| Example | Cpd No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| *(structure)* | 12 | 0.50 | 1.58 | >10.96 | 0.89 |
| *(structure)* | 13 | 0.76 | 5.36 | >10.94 | 1.55 |
| *(structure)* | 14 | 0.86 | 2.65 | >11.32 | 0.78 |
| *(structure)* | 15 | 1.23 | 2.43 | >8.32 | 0.78 |
| *(structure)* | 16 | 1.25 | 1.63 | >11.42 | 0.60 |

-continued
Table of compounds in which R^x is (i) i.e. a monocycle
| Example | Cpd No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| 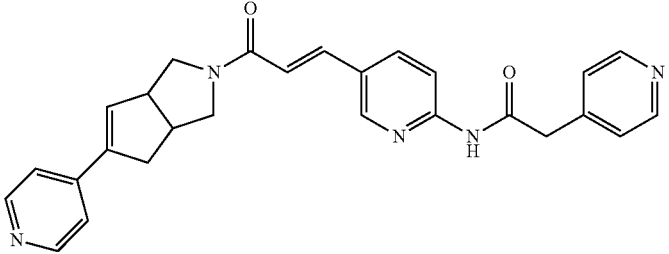 [SMILES: O=C(Cc1ccncc1)Nc1ccc(/C=C/C(=O)N2CC3C=C(c4ccccc4)CC3C2)cn1] | 17 | 1.33 | 1.40 | >4.51 | 0.65 |
| 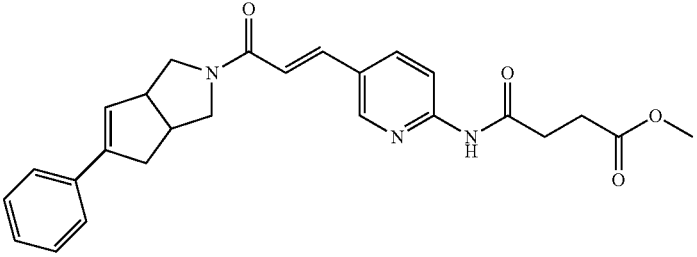 [SMILES: COC(=O)CCC(=O)Nc1ccc(/C=C/C(=O)N2CC3C=C(c4ccccc4)CC3C2)cn1] | 18 | 1.60 | 3.05 | >11.19 | 1.14 |
| 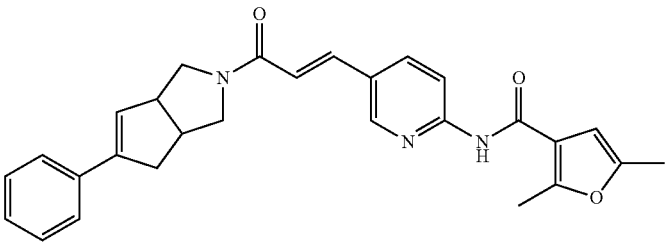 [SMILES: Cc1cc(C(=O)Nc2ccc(/C=C/C(=O)N3CC4C=C(c5ccccc5)CC4C3)cn2)c(C)o1] | 19 | 1.61 | 16.09 | 10.76 | 2.12 |
| 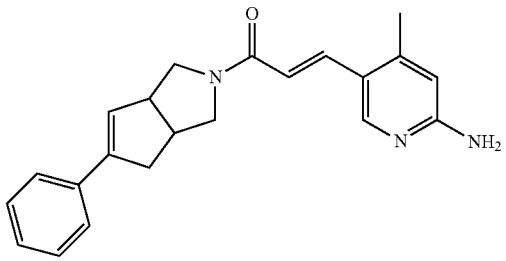 [SMILES: Cc1cc(N)ncc1/C=C/C(=O)N1CC2C=C(c3ccccc3)CC2C1] | 20 | >21.7964 | >21.7964 | 4.55 | 2.87 |
| 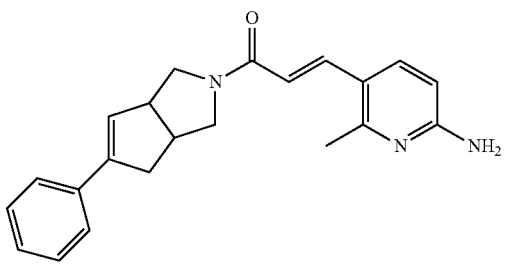 [SMILES: Cc1nc(N)ccc1/C=C/C(=O)N1CC2C=C(c3ccccc3)CC2C1] | 21 | >21.7964 | >21.7964 | 3.11 | 2.34 |

-continued
Table of compounds in which R^x is (i) i.e. a monocycle
| Example | Cpd No. | STA (361.159) IC90 µg/mL | STA + 10% HS (361.169) IC90 µg/mL | HELAM (222.125) CC50 µg/mL | FabI (300.235) IC50 µg/mL |
|---|---|---|---|---|---|
| 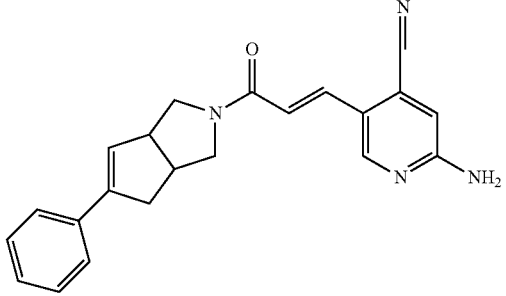 [SMILES: N=Cc1cc(N)ncc1/C=C/C(=O)N1CC2C=C(c3ccccc3)CC2C1] | 22 | >22.4892 | >22.4892 | >8.95312 | ~12.0774 |
| 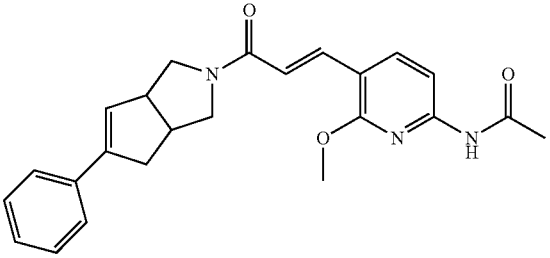 [SMILES: COc1nc(NC(C)=O)ccc1/C=C/C(=O)N1CC2C=C(c3ccccc3)CC2C1] | 23 | >25.4585 | >25.4585 | >10.1352 | 6.25 |
| 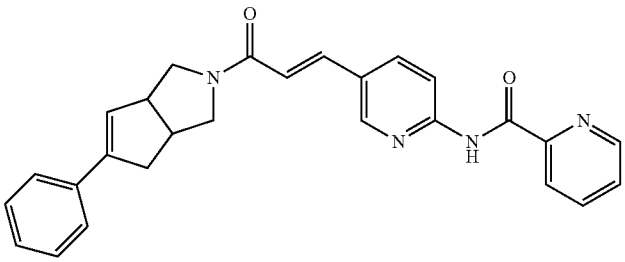 [SMILES: O=C(Nc1ccc(/C=C/C(=O)N2CC3C=C(c4ccccc4)CC3C2)cn1)c1ccccn1] | 24 | >27.5426 | >27.5426 | 7.76 | 1.51 |
| 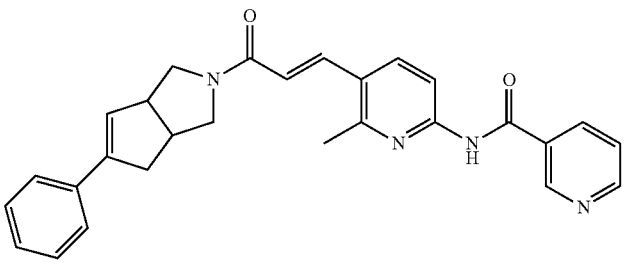 [SMILES: Cc1nc(NC(=O)c2cccnc2)ccc1/C=C/C(=O)N1CC2C=C(c3ccccc3)CC2C1] | 25 | >28.4278 | >28.4278 | >11.3173 | 6.51 |
| 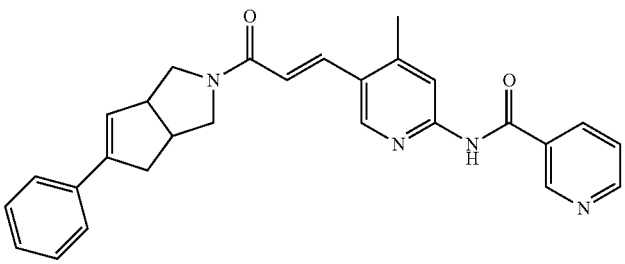 [SMILES: Cc1cc(NC(=O)c2cccnc2)ncc1/C=C/C(=O)N1CC2C=C(c3ccccc3)CC2C1] | 26 | >28.4278 | >28.4278 | >11.3173 | 4.61 |

-continued

Table of compounds in which R$^x$ is (i) i.e. a monocycle

| Example | Cpd No. | STA (361.159) IC90 μg/mL | STA + 10% HS (361.169) IC90 μg/mL | HELAM (222.125) CC50 μg/mL | FabI (300.235) IC50 μg/mL |
|---------|---------|--------------------------|-----------------------------------|----------------------------|---------------------------|
| | 27 | >29.1206 | >29.1206 | >11.5931 | 9.64 |
| | 28 | >31.3315 | >31.3315 | 2.99 | 7.34 |
| | 29 | >33.0243 | >33.0243 | 2.34 | 4.88 |
| | 30 | <0.23 | <0.23 | >11.74 | 0.65 |
| | 31 | 0.72 | 0.86 | >11.81 | 0.31 |

Table of compounds in which R^x is (i) i.e. a monocycle

| Example | Cpd No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| (structure) | 32 | <0.23 | <0.23 | >11.89 | 0.34 |
| (structure) | 33 | <0.23 | <0.23 | >11.87 | 0.61 |
| (structure) | 34 | >33.78 | >33.80 | 12.56 | 1.58 |

TABLE of compounds in which R^x is (ii) i.e. a bicycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| (structure) | 35 | 0.16 | 0.37 | >3.93 | 0.33 |

TABLE of compounds in which R$^x$ is (ii) i.e. a bicycle
| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| 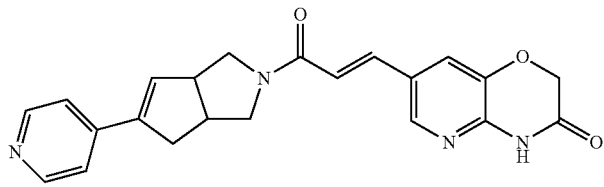 [SMILES: O=C1COc2cc(/C=C/C(=O)N3CC4C=C(c5ccncc5)CC4C3)cnc2N1] | 36 | 0.16 | <0.08 | >3.88 | 0.44 |
| 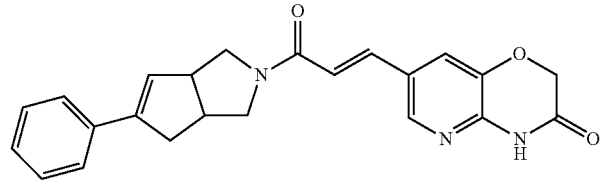 [SMILES: O=C1COc2cc(/C=C/C(=O)N3CC4C=C(c5ccccc5)CC4C3)cnc2N1] | 37 | <0.19 | 0.25 | >9.73 | ~0.45 |
| 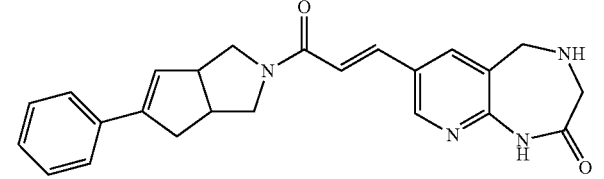 [SMILES: O=C1CNCc2cc(/C=C/C(=O)N3CC4C=C(c5ccccc5)CC4C3)cnc2N1] | 38 | <0.19 | 0.24 | >10.06 | 0.42 |
| 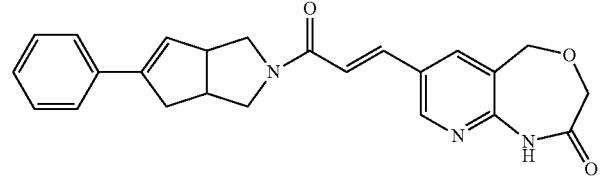 [SMILES: O=C1COCc2cc(/C=C/C(=O)N3CC4C=C(c5ccccc5)CC4C3)cnc2N1] | 39 | <0.19 | 0.35 | >10.08 | ~0.65 |
| 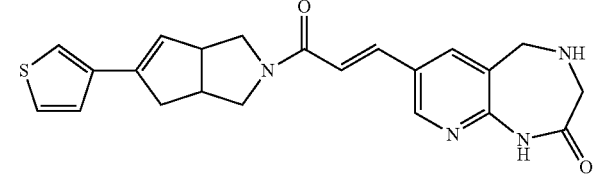 [SMILES: O=C1CNCc2cc(/C=C/C(=O)N3CC4C=C(c5ccsc5)CC4C3)cnc2N1] | 40 | <0.19 | <0.19 | >10.21 | 0.39 |
| 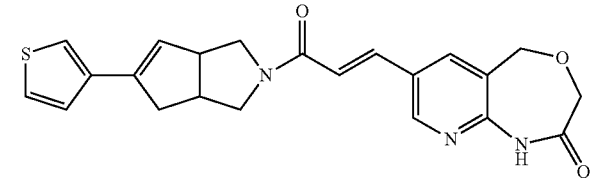 [SMILES: O=C1COCc2cc(/C=C/C(=O)N3CC4C=C(c5ccsc5)CC4C3)cnc2N1] | 41 | <0.20 | 0.23 | >10.24 | 0.42 |

TABLE of compounds in which R^x is (ii) i.e. a bicycle

| Example | Cpd. No. | STA (361.159) IC90 µg/mL | STA + 10% HS (361.169) IC90 µg/mL | HELAM (222.125) CC50 µg/mL | FabI (300.235) IC50 µg/mL |
|---|---|---|---|---|---|
| | 42 | <0.20 | <0.20 | | |
| | 43 | <0.20 | <0.20 | | |
| | 44 | <0.20 | <0.20 | | |
| | 45 | <0.20 | <0.20 | | |
| | 46 | 0.23 | 0.27 | >4.05 | 0.37 |

-continued
TABLE of compounds in which R^x is (ii) i.e. a bicycle
| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| 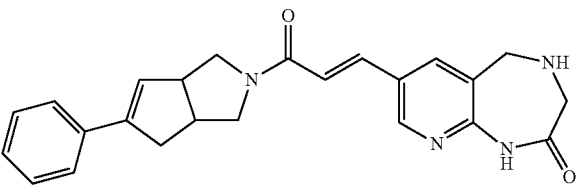 [SMILES: O=C1CNCc2cc(/C=C/C(=O)N3CC4C=C(c5ccccc5)CC4C3)cnc2N1] | 47 | 0.24 | 0.26 | >10.06 | 0.35 |
| 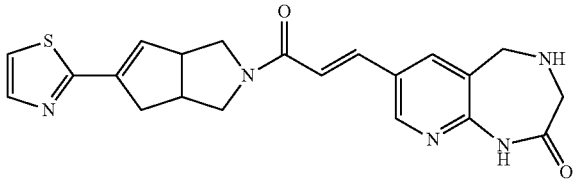 [SMILES: O=C1CNCc2cc(/C=C/C(=O)N3CC4C=C(c5nccs5)CC4C3)cnc2N1] | 48 | 0.24 | 0.21 | >10.24 | ~0.27 |
| 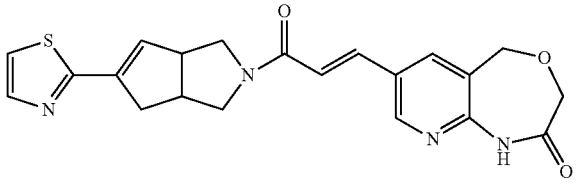 [SMILES: O=C1COCc2cc(/C=C/C(=O)N3CC4C=C(c5nccs5)CC4C3)cnc2N1] | 49 | 0.25 | 0.24 | >10.26 | ~0.38 |
| 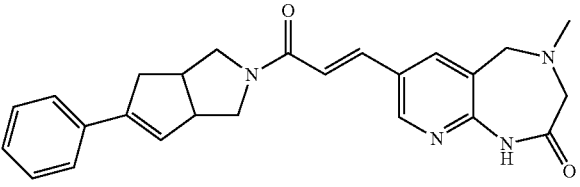 [SMILES: CN1CC(=O)Nc2ncc(/C=C/C(=O)N3CC4C=C(c5ccccc5)CC4C3)cc2C1] | 50 | 0.35 | 0.40 | >20.77 | 0.40 |
| 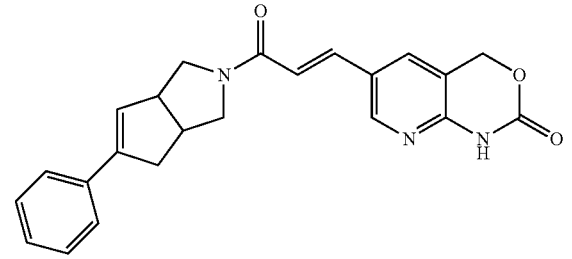 [SMILES: O=C1Nc2ncc(/C=C/C(=O)N3CC4C=C(c5ccccc5)CC4C3)cc2CO1] | 51 | 0.35 | 0.71 | >9.73 | 0.35 |
| 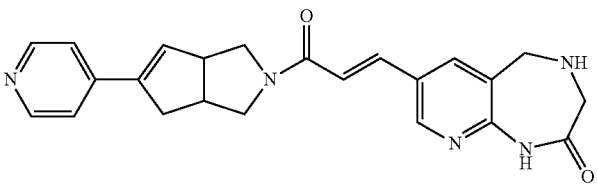 [SMILES: O=C1CNCc2cc(/C=C/C(=O)N3CC4C=C(c5ccncc5)CC4C3)cnc2N1] | 52 | 0.37 | 0.35 | >10.08 | 0.39 |

TABLE of compounds in which R^x is (ii) i.e. a bicycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| *structure* | 53 | 0.37 | 0.70 | >10.08 | 0.59 |
| *structure* | 54 | 0.38 | 0.35 | >10.11 | 0.41 |
| *structure* | 55 | 0.76 | 0.71 | >9.76 | 0.36 |
| *structure* | 56 | 1.51 | 1.44 | >10.18 | 0.48 |
| *structure* | 57 | 1.54 | 1.52 | >10.16 | 0.38 |
| *structure* | 58 | 3.39 | 3.13 | >10.49 | 0.71 |

-continued

TABLE of compounds in which R<sup>x</sup> is (ii) i.e. a bicycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
| --- | --- | --- | --- | --- | --- |
| | 59 | 3.39 | 3.17 | >11.24 | 1.00 |
| | 60 | 5.50 | 3.85 | >10.49 | 0.91 |
| | 61 | >24.07 | >24.07 | >9.58 | >19.12 |
| | 62 | >26.40 | >26.40 | >10.51 | 3.10 |
| | 63 | <0.21 | 0.36 | >10.78 | 0.61 |

-continued

TABLE of compounds in which R<sup>x</sup> is (ii) i.e. a bicycle

| Example | Cpd. No. | STA (361.159) IC90 µg/mL | STA + 10% HS (361.169) IC90 µg/mL | HELAM (222.125) CC50 µg/mL | FabI (300.235) IC50 µg/mL |
| --- | --- | --- | --- | --- | --- |
| | 64 | <0.21 | <0.21 | >10.96 | 0.36 |
| | 65 | <0.21 | <0.21 | >10.81 | 0.37 |
| | 66 | 0.76 | 0.79 | >10.41 | 0.27 |
| | 67 | <0.21 | <0.21 | >11.11 | 0.65 |
| | 68 | 0.42 | 0.43 | >12.67 | 0.43 |

TABLE of compounds in which R^x is (iii) i.e. a tricycle

| Example | Cpd. No. | STA (361.159) IC90 µg/mL | STA + 10% HS (361.169) IC90 µg/mL | HELAM (222.125) CC50 µg/mL | FabI (300.235) IC50 µg/mL |
|---|---|---|---|---|---|
| | 69 | 0.15 | 0.22 | 8.31 | 0.47 |
| | 70 | 0.17 | 0.20 | >11.62 | 0.67 |
| | 71 | <0.21 | <0.21 | 6.78 | 0.48 |
| | 72 | <0.21 | <0.21 | | |
| | 73 | <0.21 | <0.21 | 4.4 | 0.39 |
| | 74 | <0.23 | <0.23 | >11.17 | 0.46 |

-continued

TABLE of compounds in which R$^x$ is (iii) i.e. a tricycle

| Example | Cpd. No. | STA (361.159) IC90 µg/mL | STA + 10% HS (361.169) IC90 µg/mL | HELAM (222.125) CC50 µg/mL | FabI (300.235) IC50 µg/mL |
|---|---|---|---|---|---|
| | 75 | <0.25 | <0.25 | >12.65 | 0.65 |
| | 76 | 0.25 | 0.41 | >11.8 | 0.58 |
| | 77 | 0.26 | 0.59 | 1.20 | 0.56 |
| | 78 | 0.31 | <0.22 | >11.47 | 0.49 |
| | 79 | 0.36 | <0.22 | >11.44 | 0.60 |
| | 80 | 0.42 | 0.38 | >11.49 | 0.34 |

TABLE of compounds in which R^x is (iii) i.e. a tricycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
| --- | --- | --- | --- | --- | --- |
| *(structure)* | 81 | 0.45 | 0.43 | | |
| *(structure)* | 82 | 0.45 | 0.43 | >12.1 | 0.48 |
| *(structure)* | 83 | 0.48 | 0.47 | >12.9 | 0.63 |
| *(structure)* | 84 | 0.92 | 0.87 | >12.52 | 0.67 |
| *(structure)* | 85 | 1.67 | 1.62 | >11.57 | 0.44 |

-continued

TABLE of compounds in which R^x is (iii) i.e. a tricycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| | 86 | 3.47 | 3.81 | | 0.80 |
| | 87 | | | | |
| | 88 | | | | |
| | 89 | | | | |
| | 90 | <0.21 | <0.21 | 4.4 | 0.39 |

Example Z

Z.1 Thermodynamic Solubility

The pH solubility profiling was carried out at ambient temperature for a period of 4 days. A saturation solubility study was carried out in order to determine maximum solubility in a particular buffer solution. The compound was added to respective buffer solution until saturation point is reached. This was followed by shaking the flask for 4 days at ambient temperature. After 4 days, the solutions were filtered and injected on UPLC and the concentration was determined using a generic HPLC method.
Results

|  | Cpd. No. 74 | Cpd. No. 79 | Cpd. No. 48 | Cpd. No. 9 | Cpd. No. 68 |
|---|---|---|---|---|---|
| 0.01N HCl | 0.67 | >1.163 | >2.556 | >1.251 | 0.04 |
| 20% HP-β-CD 0.01N HCl | >2.356 | >4.494 | NT | >4.928 | NT |
| 10% HP-β-CD buffer pH 2 | NT | NT | NT | NT | NT |
| 20% HP-β-CD buffer pH 2 | NT | NT | NT | NT | NT |
| Buffer pH 4 | 0.04 | 0.15 | 0.44 | 0.12 | <0.01 |
| 10% HP-β-CD buffer pH 4 | >1.276 | >5.33 | >2.466 | 0.83 | 1.11 |
| 20% HP-β-CD buffer pH 4 | >2.358 | >4.454 | >4.72 | >5.226 | >2.54 |
| Buffer pH 7.4 | 0.03 | 0.01 | >1.225 | <0.01 | <0.01 |
| 10% HP-β-CD buffer pH 7.4 | >1.213 | >5.11 | >1.379 | >1.125 | 0.48 |
| 20% HP-β-CD buffer pH 7.4 | >1.327 | >4.878 | >2.41 | >4.936 | 0.90 |

NT = not tested

Z.2 Antimicrobial Spectrum of Activity

Minimum Inhibitory Concentrations (MICs) are determined in accordance with the Clinical and Laboratory Standards Institute (CLSI) methodology against aerobic bacteria (CLSI M07-A8) (see Clinical and Laboratory Standards Institute. 2009. Methods for dilution antimicrobial susceptibility tests for bacteria that grow aerobically. CLSI document M07-A8, Vol. 29, No. 2.) by the broth microdilution method with cation-adjusted Mueller-Hinton broth (CA-MHB) medium for the majority of organisms, except for *Haemophilus influenza*, where Haemophilis test medium (HTM) broth is used. Descriptions of the individual organisms can be found in the table. Where possible, ATCC standard strains are tested.

The inoculum density for the susceptibility testing is standardized to give a final inoculum of approximately $5 \times 10^5$ CFU/mL. The broth MIC is determined as the lowest concentration of drug that prevented visible growth after 16-24 hours (species dependent) of incubation at 35° C.-37° C.

TABLE

| Description of individual organisms tested | | |
|---|---|---|
| Organism | Characteristics | MIC test medium |
| *Staphylococcus aureus* | ATCC 29213; reference strain MSSA | MHB |
| *Staphylococcus aureus* | ATCC 43300; reference strain MRSA | MHB |
| *Staphylococcus aureus* | NRS119; LZD-R; SCCmec IV; origin: US | MHB |
| *Staphylococcus aureus* | NRS120; LZD-R; SCCmec IV; origin: US | MHB |
| *Staphylococcus aureus* | NRS121; LZD-R; SCCmec IV; origin: US | MHB |
| *Escherichia coli* | ATCC 25922; reference strain | MHB |
| *Escherichia coli* | Tol C mutant | MHB |
| *Haemophilus influenzae* | ATCC 49247; reference strain | HTM broth |
| *Moraxella catarrhalis* | ATCC 8176; b-lactamase negative | MHB |

Stock solutions of the compounds are prepared in DMSO at concentrations of 1 mg/mL. Linezolid is prepared in DMSO at a concentration of 2 mg/mL. Stock solutions of all compounds are diluted into CA-MHB to give a range of two-fold dilutions, depending upon the sensitivity of the organism being tested.

Results

Compounds of the invention/examples are found to exhibit a broader spectrum of antibacterial activity, for instance compounds may be found to be active against a number of bacterial strains e.g. *S. aureus* ATCC 29213, *S. aureus* NRS119, *S. aureus* NRS120, *S. aureus* NRS121, *E. coli* tolC mutant, *E. coli* ATCC 25922, *H. influenza* ATCC 49247, *M. catarrhalis* ATCC 8176.

Z.3 In Vivo Pharmacokinetic and Oral Bioavailability

The in vivo pharmacokinetics and oral bioavailability of the compound of the examples were/are investigated in male Swiss mice (fed) following single intravenous (i.v.) bolus and oral (p.o.) administration. For the i.v. and p.o. solution formulations, the compound was/is dissolved in a 20% HP-β-CD solution. The pH of the formulations was/is around pH 4. All i.v. formulations were isotonic.

Results

| Pharmacokinetic parameters in mouse following i.v. and p.o. administration (20% HP-β-cyclodextrin) | | | |
|---|---|---|---|
|  | Cpd. No. 38 | Cpd. No. 48 | Cpd. No. 37 |
| i.v. | | | |
| Dose (mg/kg) | 2.5 | 2.5 | 2.5 |
| n | 3 | 3 | 3 |
| $C_0$ (ng/mL) | n.d. | 4561 | 3932 |
| Plasma clearance Cl (L/h/kg) | 1.3 | 1.6 | 0.32 |
| $Vd_z$ (L/kg) | 3.1 | 2.8 | 1.5 |
| $AUC_{0-inf}$ (ng·h/mL) | 2003 | 1601 | 7889 |
| Half life ($t_{1/2}$) (h) | 1.7 | 1.2 | 3.33 |
| p.o | | | |
| Dose (mg/kg) | 10 | 10 | 5 |
| n | 3 | 3 | 3 |
| $C_{max}$ (ng/mL) | 665 | 483 | 2333 |
| $T_{max}$ (h) | 1.7 | 1.3 | 1.0 |

-continued

Pharmacokinetic parameters in mouse following
i.v. and p.o. administration (20% HP-β-cyclodextrin)

|  | Cpd. No. 38 | Cpd. No. 48 | Cpd. No. 37 |
|---|---|---|---|
| $AUC_{0\text{-}inf}$ (ng.h/mL) | 2858 | 2046 | 15608 |
| Half life ($t_{1/2}$) (h) | 2.2 | n.d. | 3.5 |
| Oral bioavailability (%) | 36 | 32 | 98 |

Z.4 In Vivo Efficacy

The concept of studying the in vivo effect of an antibacterial compound by treating intraperitoneally infected mice was introduced in 1911 for optochin against pneumococci (Morgenroth and Levy, 1911). The popularity of the model comes from the ease of its use with short-duration experiments, reproducible infections and simple end-points.

Method

Methicillin-sensitive *S. aureus* strain ATCC 29213 was used to infect female Swiss albino mice. A Brain Heart Infusion (BHI) broth bacterial culture was inoculated the day before infection, incubated at 37° C. overnight and diluted in fresh BHI broth to the desired concentration. Intraperitoneal (i.p.) injection of ~5×10⁹ colony forming units (CFU) was performed in either of the lateral lower quadrants of the abdomen. After inoculation, mice were kept in their cages under daily observation for development of signs of infection or death. For the treatment of mice, the p.o. route was used and each mouse was treated individually by gavage. Example of Cpd No. 48 was formulated as a 20% HP-β-cyclodextrin and example of Cpd No. 38 was formulated as a water/Tween-20 suspension. The parameter used for monitoring the course of infection and the effect of treatment was death or survival of the animals over 3 days post-infection. As death could also be due to toxic side effects, a non-infected control group of 3 mice, treated with the highest dose of the compound tested, was included.

Results

In vivo antibacterial activity in peritonitis model of *S. aureus* infection (ATCC 29213) after oral dosing using solutions

| Compound | Infection Route | Inoculum (log10) | Formulation | Treatment Route | Treatment Dose (mpk) | % Survival |
|---|---|---|---|---|---|---|
| 48 | IP | 8.9 | Sol 20% CD + 1HCl | PO, QD | 1; 5 | 57; 100 |
| 38 | IP | 8.7 | 20% CD + 2H2T | IV, QD | 2.5; 5 | 75; 100 |

The invention claimed is:

1. A compound of formula (I)

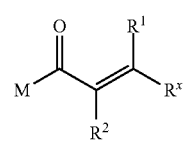

(I)

wherein
M is moiety of formula

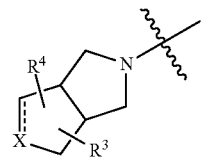

the ⚌ bond is a single bond or a double bond,
wherein when ⚌ is a double bond, then X is C(R⁴);
and when ⚌ is a single bond, then X is N(R⁴) or C(R³)(R⁴);

$R^1$ is hydrogen, $C_{1\text{-}4}$alkyl or halo;
$R^2$ is hydrogen, $C_{1\text{-}4}$alkyl or halo;
$R^x$ is selected from the group of moieties of formulae (i), (ii) and (iii),

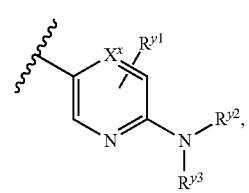

(i)

wherein $X^x$ is C(H), C($R^{yy}$) or N;
- $R^{yy}$ is selected from the group consisting of hydrogen, halo, —CN, A1 and B1;
  - wherein each of said A1 and B1 is optionally and independently substituted by one or more fluoro atoms, and said A1 is —O—$C_{1-6}$ alkyl, and said B1 is $C_{1-6}$ alkyl;
- $R^{y1}$ is one to three optional substituents each independently selected from hydrogen, halo, —CN, A1 or B1;
- each $R^{y2}$ and $R^{y3}$ independently is hydrogen or -$Q^1$-$R^5$;
  - each $Q^1$ independently is a direct bond or —C(O)—;
  - each $R^5$ is hydrogen, A2, B2, A3 or B3; wherein each of said A2 and B2 is optionally and independently substituted by at least one of =O and $Q^2$, said A2 is $C_{1-6}$ alkyl, said B2 is heterocycloalkyl, and wherein each of said A3 and B3 is optionally and independently substituted by at least one of $Q^3$ substituents, said A3 is aryl and said B3 is heteroaryl;
  - $Q^2$ is selected from the group consisting of halo, —CN, A4, B4 and B5;
    - wherein said A4 is optionally substituted by at least one fluoro, said A4 is —$OC_{1-6}$ alkyl, and each of said B4 and B5 is optionally and independently substituted by one or more substituents selected from the group consisting of halo, —CN, optionally fluoro-substituted $C_{1-3}$ alkyl and optionally fluoro-substituted —$OC_{1-3}$ alkyl, said B4 is aryl, and said B5 is heteroaryl;
  - $Q^3$ is selected from the group consisting of halo, —CN, A5 and B6; wherein each of said A5 and B6 is optionally and independently substituted by at least one fluoro, and said A5 is —O—$C_{1-6}$ alkyl and said B6 is $C_{1-6}$ alkyl;

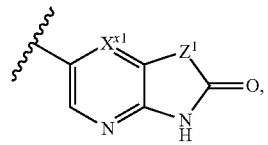
(ii)

wherein $X^{x1}$ is C(H) or N;
$Z^1$ is —$X^1$—O—$X^{1a}$—, —$X^2$—N($R^{z3}$)—$X^{2a}$—, or —$X^3$—S—$X^{3a}$—;
- each of $X^1$, $X^2$ and $X^3$ independently is a direct bond, —C(O)—, or —C($R^{z4}$)($R^{z5}$)—;
- each of $X^{1a}$, $X^{2a}$ and $X^{3a}$ independently is a direct bond or —$V^1$—C($R^{z1}$)($R^{z2}$)—;
- $V^1$ is a direct bond or —C(O)—;
- each of $R^{z1}$, $R^{z2}$, $R^{z3}$, $R^{z4}$ and $R^{z5}$ independently is selected from the group consisting of hydrogen, A6- and B7, wherein said A6 is optionally substituted by at least one of =O and halo, said A6 is $C_{1-6}$ alkyl, said B7 is optionally substituted by at least one of =O, halo and $C_{1-3}$ alkyl, and said B7 is heterocycloalkyl;

and

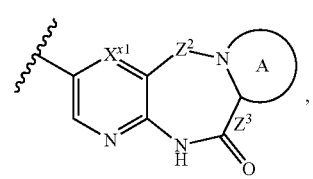
(iii)

wherein
$X^{x1}$ is C(H) or N;
$Z^2$ is —C($R^{z6}$)($R^{z7}$)— or —C(O)—;
$Z^3$ is —$CH_2$ and moiety (iii) is moiety (iii.1)

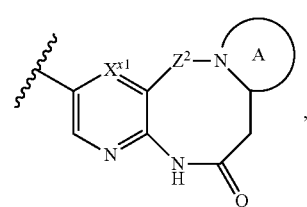
(iii.1)

or a bond and moiety (iii) is moiety (iii.2)

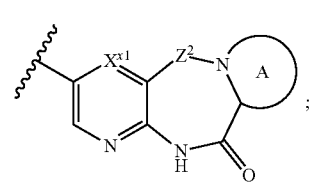
(iii.2)

A is a 5- or 6-membered ring optionally containing one, two or three double bonds and optionally containing an additional one to three heteroatoms, wherein each one of said heteroatoms is N or O, wherein said A is optionally substituted by one or more substituents each independently selected from =O and $R^{z8}$;
each $R^{z6}$, $R^{z7}$ and $R^{z8}$ independently is hydrogen or A7, wherein said A7 is optionally substituted by at least one substituent selected from the group consisting of =O, —$OC_{1-4}$ alkyl and halo and said A7 is $C_{1-6}$ alkyl;
each $R^3$ independently is hydrogen, halo, —$OR^{10}$ or A8 wherein said A8 is optionally substituted by at least one halo and said A8 is $C_{1-6}$ alkyl;
each $R^4$ independently is hydrogen, halo or -$T^1$-$R^{20}$;
  wherein each $T^1$ independently is a bond, —O—, —C(O)—, —C(O)—O—, —O—C(O)—, —C(O)—N($R^{21}$)— or —S(O)$_{n1}$— wherein n1 is 0, 1 or 2, and $R^{21}$ is hydrogen or $C_{1-6}$ alkyl;
each $R^{10}$ and each $R^{20}$ independently is A9, B8 or B9, wherein said A9 is optionally and independently substituted by at least one substituent selected from the group consisting of =O and $Y^1$, and said A9 is $C_{1-6}$ alkyl, each of said B8 and B9 is optionally substituted by one or more substituents independently selected from $Y^2$, said B8 is aryl and said B9 is heteroaryl;
each $Y^1$ independently is halo, —O—$R^{30}$, —CN, B10 or B11 wherein each of said B10 and B11 is optionally substituted by at least one substituent selected from the group consisting of halo, —O—$C_{1-3}$alkyl and $C_{1-3}$ alkyl and said B10 is aryl, and said B11 is heteroaryl;

each $Y^2$ independently is halo, A10 or A11; wherein each of said A10 and A11 is optionally substituted by at least one fluoro, said A10 is —$OC_{1-6}$alkyl, and said A11 is $C_{1-6}$ alkyl;

each $R^{30}$ independently is hydrogen, A12, B12 or B13, wherein said A12 is optionally substituted by at least one fluoro, said A12 is $C_{1-6}$ alkyl, each of said B12 and B13 is independently and optionally substituted by at least one substitutent selected from the group consisting of halo, —O—$C_{1-3}$alkyl and $C_{1-3}$ alkyl, said B12 is aryl, and said B13 is heteroaryl;

or a pharmaceutically acceptable salt thereof.

2. The compound as claimed in claim 1, wherein moiety M is selected from the group consisting of:

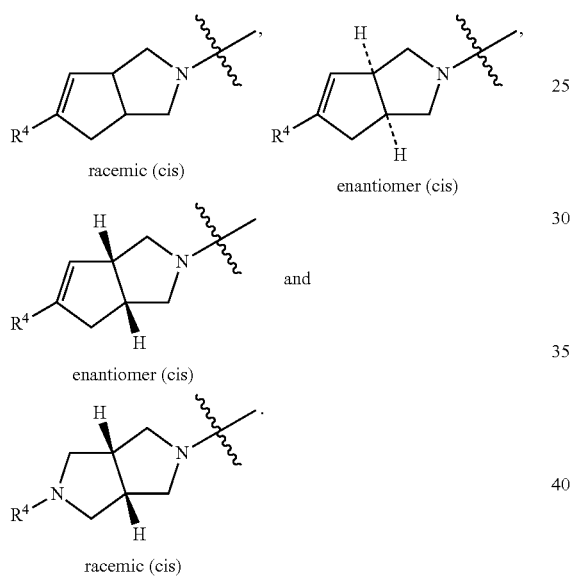

3. The compound as claimed in claim 1 wherein $R^4$ is selected from the group consisting of:

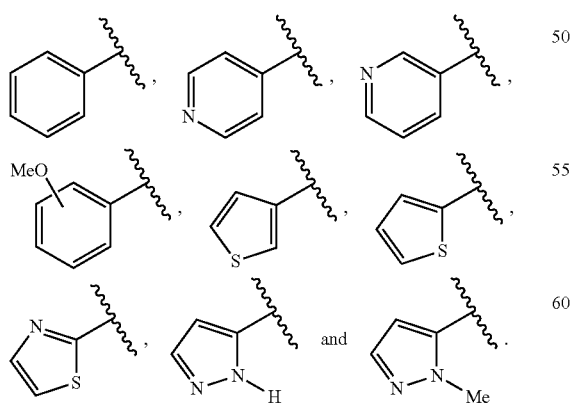

4. The compound as claimed in claim 1, wherein each of $R^{y1}$ and $R^{yy}$ is hydrogen, and $R^{y2}$ is -$Q^1$-$R^5$.

5. The compound as claimed in claim 1, wherein $Q^1$ is —C(O)—, and $R^5$ is selected from the group consisting of:

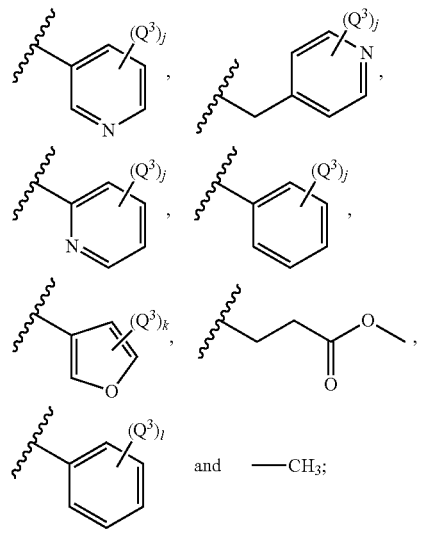

and —$CH_3$;

wherein
j is 0, 1, 2, 3 or 4;
k is 0, 1, 2 or 3;
l is 0, 1, 2, 3, 4 or 5;
and wherein each of $(Q^3)_j$, $(Q^3)_k$ and $(Q^3)_l$ is independently selected from any other $Q^3$ assignment.

6. The compound as claimed in claim 1, wherein when $R^x$ is moiety (ii), said $R^x$ is selected from the group consisting of:

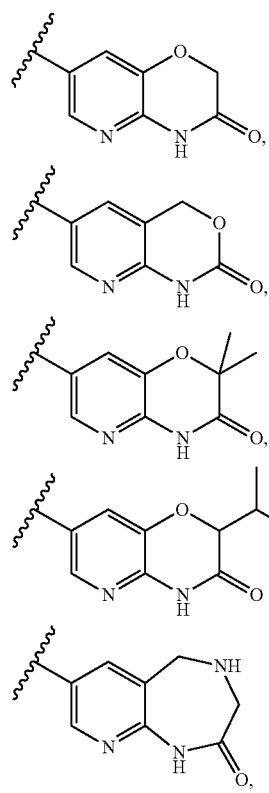

121

-continued

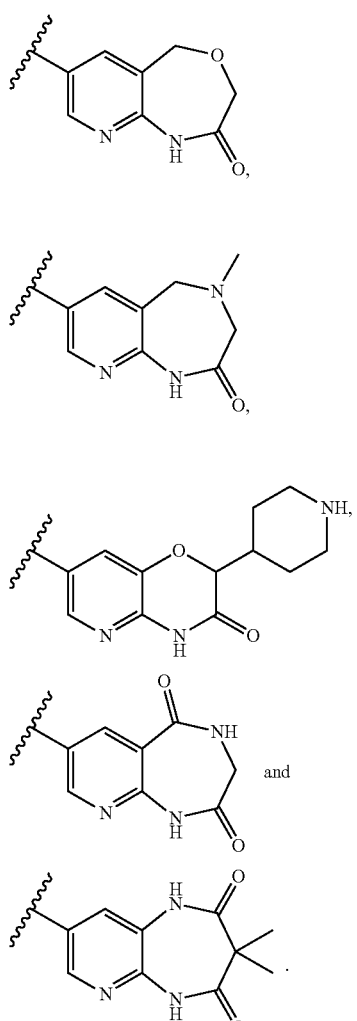

7. The compound as claimed in claim 1, wherein when $R^x$ is moiety (iii), said $R^x$ is selected from the group consisting of:

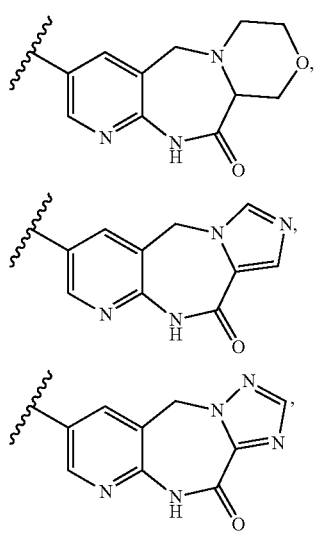

122

-continued

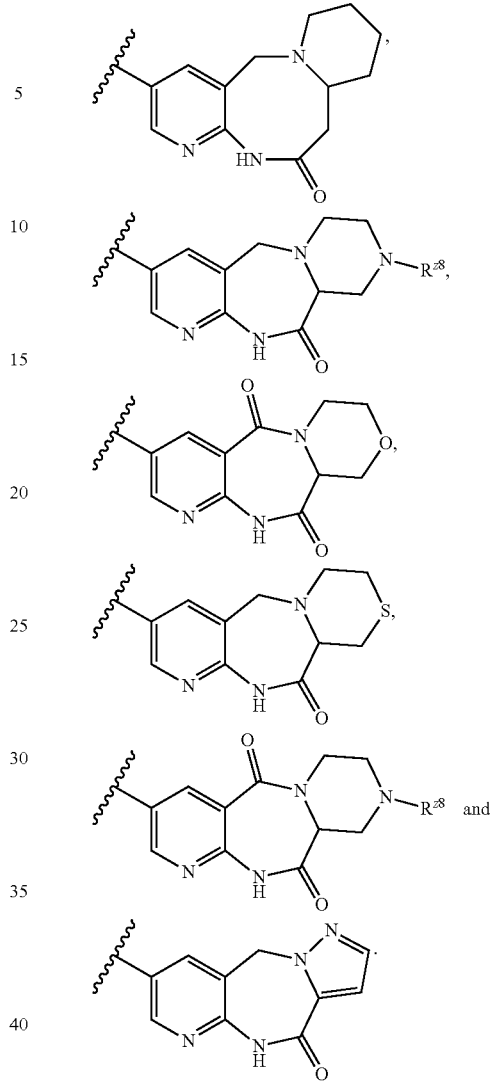

8. A pharmaceutical composition comprising a pharmaceutically acceptable carrier and a therapeutically active amount of a compound as claimed in claim 1.

9. A process for preparing a pharmaceutical composition wherein a therapeutically active amount of a compound as claimed in claim 1 is intimately mixed with a pharmaceutically acceptable carrier.

10. A method of treating a bacterial infection, comprising the administration of a therapeutically effective amount of at least one compound as claimed in claim 1.

11. A method of treating a bacterial infection as claimed in claim 10 wherein said bacterial infection is caused by a bacterium that expresses a FabI enzyme.

12. A process for preparing a compound as claimed in claim 1, comprising:
(i) reacting a compound of formula (II),

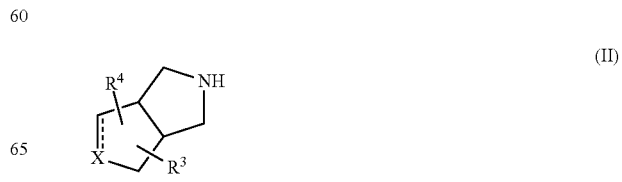

with a compound of formula (III),
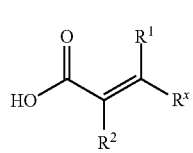
(III)
to yield a compound of formula (IV); and
(ii) coupling a compound of formula (IV),
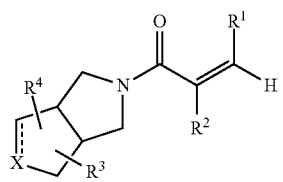
(IV)
with moiety $R^x$, to yield a compound of formula (I).
* * * * *